(12) United States Patent
Spaete et al.

(10) Patent No.: US 6,291,236 B1
(45) Date of Patent: Sep. 18, 2001

(54) HUMAN CYTOMEGALOVIRUS DNA SEQUENCES

(75) Inventors: Richard Spaete, Belmont; Tai-An Cha, San Ramon, both of CA (US)

(73) Assignee: Aviron, Mountain View, CA (US)

( * ) Notice: Subject to any disclaimer, the term of this patent is extended or adjusted under 35 U.S.C. 154(b) by 0 days.

(21) Appl. No.: 09/527,657

(22) Filed: Mar. 17, 2000

Related U.S. Application Data

(62) Division of application No. 09/253,682, filed on Feb. 18, 1999, now Pat. No. 6,040,170, which is a division of application No. 08/926,922, filed on Sep. 10, 1997, now Pat. No. 5,925,751, which is a division of application No. 08/414,926, filed on Mar. 31, 1995, now Pat. No. 5,721,354.

(51) Int. Cl.[7] ............................ C12N 15/00; C12N 15/09; C12Q 1/70; C07H 21/04; A61K 39/245
(52) U.S. Cl. ........................ 435/320.1; 435/5; 435/69.3; 435/172.3; 435/252.3; 536/23.72; 424/230.1
(58) Field of Search ..................... 435/252.3, 5, 172.3, 435/320.1, 69.3; 536/23.72; 424/230.1

(56) References Cited

U.S. PATENT DOCUMENTS

| | | | |
|---|---|---|---|
| 5,075,213 | 12/1991 | Pande et al. | 435/5 |
| 5,194,256 | 3/1993 | Rasmussen et al. | 424/8 |
| 5,721,354 | * 2/1998 | Spaete et al. | 536/23.72 |
| 5,925,751 | * 7/1999 | Spaete et al. | 536/23.72 |

OTHER PUBLICATIONS

Zaia, Comparative Analysis of Human Cytomegalivirus a–Sequence in Multiple Clinical Isolates etc., J. Clin. Microbio. 28 (1990) 2602–07.

Pande, Human Cytomegalovirus Strain Towne pp65 Gene: Nucleotide Sequence and Expression in *Escherichia coli*, Virology 182 (1991) 220–28.

Pande, Human Cytomegalovirus Strain pp28 Gene: Comparison to pp28 of HCMV AD169 etc. Virology 194 (1991) 762–67.

Chou, Analysis of Interstain Variation in Cytomegalovirus Glycoprotein B etc., J Inf Diseases 163 (1991) 1229–34.

Robson, Primate Cytomegalovirus Assembly Protein: Genome Location and Necleotide Sequence, J Virol 63 (1989) 669–76.

Lehner, Comparative Sequence Analysis of Human Cytomegalovirus Strains, J Clin Microbiol 29 (1991) 2494–2502.

Fries, Frequency Distribution of Cytomegalovirus Envelop Glycoprotein Geneotypes etc, J Inf Diseases 169 (1994) 478–83.

Quinnan, Comparative Virulence and Immunogenicityt of the Towne Strain etc, Annals of Int Med 101 (1984) 478–83.

Plotkin, Lancet 1 (1984) 528–30.

Plotkin, Protective Effects of Towne Cytomegalovirus Vaccine etc, J Inf Disease 159 (1989) 860–65.

Huang, Detection of Human Cytomegalovirus and Analysis of Strain Variation, Yale J Biol and Med 49 (1976) 29–43.

Kilpatrick, Analysis of Cytomegalovirus Genomes with Restriction Endonucleases etc, J virol 18 (1976) 1095–1105.

LaFemina, Structural Organization of the DNA Molecules from Human Cytomegalovirus, in "Animal Virus Genetics", Field, BN and R Joenish, eds., Academic Press, NY 1980, pp. 39–53.

Chandler, Comparison of Restriction Site Polymorphisms Among Clinical Isolates and Laboratory Strains of Hukman Cytomegalovirus, J. Gen Virol 67 (1986) 2179–92.

Spaete, Human Cytomegalovirus Strain Towne Glycoprotein B etc, Virology 167 (1988) 207–25.

Marshall, Cytomegalovirus Vaccines, in "The Human Herpesviruses," RJ Whitley, B Roizman and C Lopez, eds., Raven Press, NY, pp 381–395, (1993).

Alford, Cytomegalovirus, in "The Human Herpesviruses," RJ Whitley, B Roizman and C Lopez, eds., Raven Press, NY, pp 227–255, (1993).

Chou, Differentiation of Cyutomegalovirus Strains by Restriction Analysis etc, J Inf Diseases 162 (1990) 738–42.

Pritchett, DNA Nucleotide Sequence Heterogeneity Between the Towne and AD 169 Strains of Cytomegalovirus, J. Virol 36 (1980) 152–61.

* cited by examiner

*Primary Examiner*—Hankyel T. Park
(74) *Attorney, Agent, or Firm*—Luann Cserr; Tracy Dunn

(57) ABSTRACT

Provided are novel Toledo and Towne Human cytomegalovirus DNA sequences (HCMV) and proteins encoded thereby. The sequences are useful in methods and compositions for detecting HCMV infections and in immunogenic compositions for preventing HCMV infections.

8 Claims, 53 Drawing Sheets

```
                                                        UL133
         10         20         30         40         50  ▼     60
CGCTGTAGGG ATAAATAGTG CGATGGCGTT TGTGGGAGAA CGCAGTAGCG ATGGGTTGCG
GCGACATCCC TATTTATCAC GCTACCGCAA ACACCCTCTT GCGTCATCGC TACCCAACGC 70         80         90        100        110        120
ACGTGCACGA TCCTTCGTGG CAATGCCAAT GGGGCGTTCC CACGATTATC GTGGCCTGGA
TGCACGTGCT AGGAAGCACC GTTACGGTTA CCCCGCAAGG GTGCTAATAG CACCGGACCT 130        140        150        160        170        180
TAACATGCGC GGCTTTAGGA ATTTGGTGTT TGGCGGGATC GTCGGGCGAT GTCTCTTCGG
ATTGTACGCG CCGAAATCCT TAAACCACAA ACCGCCCTAG CAGCCGCCTA CAGAGAAGCC 190        200        210        220        230        240
GACCCGGCAT CGCAGCCGTA GTCGGCTGTT CTGTTTTCAT GATTTTCCTC TGCGCGTATC
CTGGGCCGTA GCGTCGGCAT CAGCCGACAA GACAAAAGTA CTAAAAGGAG ACGCGCATAG 250        260        270        280        290        300
TCATCCGTTA CCGGGAATTC TTCAAAGACT CCGTAATCGA CCTCCTTACC TGCCGATGGG
AGTAGGCAAT GGCCCTTAAG AAGTTTCTGA GGCATTAGCT GGAGGAATGG ACGGCTACCC 310        320        330        340        350        360
TTCGCTACTG CAGCTGCAGC TGTAAGTGCA GCTGCAAATG CATCTCGGGC CCCTGTAGCC
AAGCGATGAC GTCGACGTCG ACATTCACGT CGACGTTTAC GTAGAGCCCG GGGACATCGG 370        380        390        400        410        420
GCTGCTGTTC AGCGTGTTAC AAGGAGACGA TGATTTACGA CATGGTCCAA TACGGTCATC
CGACGACAAG TCGCACAATG TTCCTCTGCT ACTAAATGCT GTACCAGGTT ATGCCAGTAG 430        440        450        460        470        480
GACGGGCGTCC CGGACACGGC GACGATCCCG ACAGGGTGAT CTGCGAGATA GTCGAGAGTC
CTGCCGCAGG GCCTGTGCCG CTGCTAGGGC TGTCCCACTA GACGCTCTAT CAGCTCTCAG
```

FIG._1A-1

```
         490        500        510        520        530        540
CCCCGGTTTC GGCGCCGACG GTGTCCGTCC CCCCGCCGTC GGAGGAGTCC CACCAGCCCG
GGGGCCAAAG CCGCGGCTGC CACAGGCAGG GGGGCGGCAG CCTCCTCAGG GTGGTCGGGC
UL134
         550        560        570        580        590        600
TCATCCCACC GCAGCCGCCA GCACCGACAT CGGAACCCAA ACCGAAGAAA GGTAGGGCGA
AGTAGGGTGG CGTCGGCGGT CGTGGCTGTA GCCTTGGGTT TGGCTTCTTT CCATCCCGCT
         610        620        630        640        650        660
AAGATAAACC GAAGGGTAGA CCGAAAGACA AACCTCCGTG CGAACCGACG GTGAGTTCAC
TTCTATTTGG CTTCCCATCT GGCTTTCTGT TTGGAGGCAC GCTTGGCTGC CACTCAAGTG
         670        680        690        700        710        720
AACCACCGTC GCAGCCGACG GCAATGCCCG GCGGTCCGCC CGACGCGCCT CCCCCCGCCA
TTGGTGGCAG CGTCGGCTGC CGTTACGGGC CGCCAGGCGG GCTGCGCGGA GGGGGCGGT
         730        740        750        760        770        780
TGCCGCAGAT GCCACCCGGC GTGGCCGAGG CGGTACAAGC TGCCGTGCAG GCGGCCGTGG
ACGGGCGTCTA CGGTGGGCCG CACCGGCTCC GCCATGTTCG ACGGCACGTC CGCCGGCACC
         790        800        810        820        830        840
CCGCGGCTCT ACAACAACAG CAGCAGCATC AGACCGGAAC CCCGGTGCGA
GGGCCGAGA TGTTGTTGTC GTCGTCGTAG TCTGGCCTTG GGCCGG GGGCCACGCT
                                         UL133  GTAA CCCGCC
                                                CATT GGGGCGG
         850        860        870        880        890        900
 TAAGGAATT TCCGACTTGG CGCACATCTC CTTCCTCAAT GTTTGGACAA TAAACACATT
 ATTCCTTAAA AGGCTGAACC GCGTGTAGAG GAAGGAGTTA CAAACCTGTT ATTTGTGTAA
                                                UL135
         910        920        930        940        950        960
CCTTGCCAAA AAATGACGTT TCCAGAAATC CAAGGCATAA ATGTCCGTAC ACCGGCCCTT
GGAACGGTTT TTTACTGCAA AGGTCTTTAG GTTCCGTATT TACAGGCATG TGGCCGGGAA
```

*FIG._1A-2*

```
          970                 980         990                1000              1010              1020
CCCAACACGG        AGTTTGAGAT        TCCAAGCAGG        AGAGAAGATC        ATGGTGTGGA        TATGGCTCGG
GGGTTGTGCC        TCAAACTCTA        AGGTTCGTCC        TCTCTTCTAG        TACCACACCT        ATACCGAGCC 1030              1040              1050              1060              1070              1080
CATCGGGCTC        CTCGGCGGTA        CCGGACTGGC        TTCCCTGGTC        CTGGCCATTT        CCTTATTTAC
GTAGCCCGAG        GAGCCGCCAT        GGCCTGACCG        AAGGGACCAG        GACCGGTAAA        GGAATAAATG
                                                                            ▼UL134

1090              1100              1110              1120              1130              1140
CCAGCGCCGA        GGCCGCAAGC        GATCCGACGA        GACTTCGTCG        CGAGGCCGGC        TCCCGGGTGC
GGTCGCGGCT        CCGGCGTTCG        CTAGGCTGCT        CTGAAGCAGC        GCTCCGGCCG        AGGGCCCACG 1150              1160              1170              1180              1190              1200
TGCTTCTGAT        AAGCGTGGTG        CCTGCGCGTG        CTGCTATCGA        AATCCGAAAG        AAGACGTCGT
ACGAAGACTA        TTCGCACCAC        GGACGCGCAC        GACGATAGCT        TTAGGCTTTC        TTCTGCAGCA 1210              1220              1230              1240              1250              1260
CGAGCCGCTG        GATCTGGAAC        TGGGGCTCAT        GCGGGTGGAC        ACCCACCCGC        CGACGCCGCA
GCTCGGCGAC        CTAGACCTTG        ACCCCGAGTA        CGCCCACCTG        TGGGTGGGCG        GCTGCGGCGT 1270              1280              1290              1300              1310              1320
GGTGCCGCGG        TGTACGTCGC        TCTACATAGG        AGAGGATGGT        CTGCCGATAG        ATAAACCCGA
CCACGGCGCC        ACATGCAGCG        AGATGTATCC        TCTCCTACCA        GACGGCTATC        TATTTGGGCT 1330              1340              1350              1360              1370              1380
GTTCCCTCCG        GCGCGGTTCG        AGATCCCCGA        CGTATCCACG        CCGGGAACGC        CGACCAGCAT
CAAAGGAGGC        CGCGCCAAGC        TCTAGGGGCT        GCATAGGTGC        GGCCCTTGCG        GCTGGTCGTA 1390              1400              1410              1420              1430              1440
CGGCCGATCT        CCGTCGCATT        GCTCCTCGTC        GAGCTCTTTG        TCGTCCTCGA        CCAGCGTCGA
GCCGGCTAGA        GGCAGCGTAA        CGAGGAGCAG        CTCGAGAAAC        AGCAGGAGCT        GGTCGCAGCT
```

*FIG._1B-1*

```
      1450       1460       1470       1480       1490       1500
CACGGTGCTG TATCAGCCGC CGCCATCCTG GAAGCCACCT CCGCCGCCCG GGCGCAAGAA
GTGCCACGAC ATAGTCGGCG GCGGTAGGAC CTTCGGTGGA GGCGGCGGGC CCGCGTTCTT 1510       1520       1530       1540       1550       1560
GCGGCCGCCT ACGCCGCCGG TCCGGGCCCC CACCACGCGG CTGTCGTCGC ACAGACCCCC
CGCCGGCGGA TGCGGCGGCC AGGCCCGGGG GTGGTGCGCC GACAGCAGCG TGTCTGGGGG 1570       1580       1590       1600       1610       1620
GACGCCGATA CCCGCGCCGC GTAAGAACCT GAGCACGCCG CCCACCAAGA AAACGCCGCC
CTGCGGCTAT GGGCGCGGCG CATTCTTGGA CTCGTGCGGC GGGTGGTTCT TTTGCGGCGG 1630       1640       1650       1660       1670       1680
GCCCACGAAA CCCAAGCCGG TCGGCTGGAC ACCGCCGGTG ACACCCAGGC CCTTCCCGAA
CGGGTGCTTT GGGTTCGGCC AGCCGACCTG TGGCGGCCAC TGTGGGTCCG GGAAGGGCTT 1690       1700       1710       1720       1730       1740
AACGCCGACG CCACAAAAGC CGCCGCGGAA TCCGAGACTA CCGCGCACCG TCGGTCTGGA
TTGCGGCTGC GGTGTTTTCG GCGGCGCCTT AGGCTCTGAT GGCGCGTGGC AGCCAGACCT 1750       1760       1770       1780       1790       1800
GAATCTCTCG AAGGTGGGAC TCTCGTGTCC CTGTCCCCGA CCCCGCACGC CGACGGAGCC
CTTAGAGAGC TTCCACCCTG AGAGCACAGG GACAGGGGCT GGGGCGTGCG GCTGCCTCGG 1810       1820       1830       1840       1850       1860
GACCACGCTG CCTATCGTGT CGGTTTCCGA GCTAGCCCCG CCTCCTCGAT GGTCGGACAT
CTGGTGCGAC GGATAGCACA GCCAAAGGCT CGATCGGGGC GGAGGAGCTA CCAGCCTGTA
```

*FIG._1B-2*

```
                1870       1880       1890       1900       1910       1920
          CGAGGAACTC TTGGAACAGG CGGTGCAGAG CGTCATGAAG GACGCCGAGT CGATGCAGAT
          GCTCCTTGAG AACCTTGTCC GCCACGTCTC GCAGTACTTC CTGCGGCTCA GCTACGTCTA

UL135           1930       1940       1950       1960       1970       1980
          GACCTGAGAC CGAAAGAGCG AGCGCGTCCG TTGTACAGTT GTATAGCAGC ACACGCCTTC
          CTGGACTCTG GCTTTCTCGC TCGCGCAGGC AACATGTCAA CATATCGTCG TGTGCGGAAG 1990       2000       2010    UL136 2030       2040
          CCTCTTTTTC ACCGCAGCTA AGAGAGAGAA TCAGTCAAGG GCGTGGAGAT
          GGAGAAAAAG TGGCGTCGAT TCTCTCTCTT AGTCAGTTCC CGCACCTCTA 2050       2060       2070       2080       2090       2100
          GCCAGAAATG ACGTGGGACT TGGACGTTAG AAATAAATGG CGGCGTCGAA AGGCCCTGAG
          CGGTCTTTAC TGCACCCTGA ACCTGCAATC TTTATTTACC GCCGCAGCTT TCCGGGACTC 2110       2120       2130       2140       2150       2160
          TCGCATTCAC CGGTTCTGGG AATGTCGGCT ACGGGTGTGG TGGCTGAGTG ACGCCGGCGT
          AGCGTAAGTG GCCAAGACCC TTACAGCCGA TGCCCACACC ACCGACTCAC TGCGGCCGCA 2170       2180       2190       2200       2210       2220
          AAGAGAAACC GACCCACCGC GTCCCCGACG CCGCCCGACT TGGATGACCG CGGTGTTTCA
          TTCTCTTTGG CTGGGTGGCG CAGGGGCTGC GGCGGGCTGA ACCTACTGGC GCCACAAAGT 2230       2240       2250       2260       2270       2280
          CGTTATCTGT GCCGTTTTGC TTACGCTTAT GATTATGGCC ATCGGCGCGC TCATCGCGTA
          GCAATAGACA CGGCAAAACG AATGCGAATA CTAATACCGG TAGCCGCGCG AGTAGCGCAT 2290       2300       2310       2320       2330       2340
          CTTAAGATAT TACCACCAGG ACAGTTGGCG AGACATGCTC CACGATCTAT TTTGCGGCTG
          GAATTCTATA ATGGTGGTCC TGTCAACCGC TCTGTACGAG GTGCTAGATA AAACGCCGAC
```

FIG._1C-1

```
2350      2360      2370      2380      2390      2400
TCATTATCCC GAGAAGTGCC GTCGGCACCA CGAGCGGCAG AGAAGGAGAC GGCAAGCCAT
AGTAATAGGG CTCTTCACGG CAGCCGTGGT GCTCGCCGTC TCTTCCTCTG CCGTTCGGTA 2410      2420      2430      2440      2450      2460
GGATGTGCCC GACCCGGAAC TCGGCGACCC GGCCCGCCGG CCGTTGAACG GAGCTATGTA
CCTACACGGG CTGGGCCTTG AGCCGCTGGG CCGGGCGGCC GGCAACTTGC CTCGATACAT 2470      2480      2490      2500      2510      2520
CTACGGCAGC GGCTGTCGCT TCGACACGGT GGAAATGGTG GACGAGACGA GACCCGCGCC
GATGCCGTCG CCGACAGCGA AGCTGTGCCA CCTTTACCAC CTGCTCTGCT CTGGGCGCGG 2530      2540      2550      2560      2570      2580
GCCGGCGCTG TCATCGCCCG AAAACCGGCA CGATAGCAAC GACGACGCGG TTGCCGGCGG
CGGCCGCGAC AGTAGCGGGC TTTGGCCGCT GCTATCGTTG CTGCTGCGCC AACGGCCGCC 2590      2600      2610      2620      2630      2640
AGGTGCTGGC GGGGTAACAT CACCCGCGAC TCGTACGACG TCGCCGAACG CACTGCTGCC
TCCACGACCG CCCCATTGTA GTGGGCGCTG AGCATGCTGC AGCGGCTTGC GTGACGACGG
                     ▲UL137

2650      2660      2670      2680      2690      2700
AGAATGGATG GATGCGGTGC ATGTGGCGGT CCAAGCCGCC GTTCAAGCGA CCGTGCAAGT
TCTTACCTAC CTACGCCACG TACACCGCCA GGTTCGGCGG CAAGTTCGCT GGCACGTTCA 2710      2720      2730   UL136 2740      2750      2760
AAGTGGCCCG CGGGAGAACG CCGTATCTCC CGCTACGTAA GAGGGTTGAG GGGGCCGTTC
TTCACCGGGC GCCCTCTTGC GGCATAGAGG GCGATGCATT CTCCCAACTC CCCCGGCAAG
                                  ▲

2770      2780      2790      2800      2810      2820
CCGCGCGAGT GCTGTACAAA AGAGAGAGAC TGGGACGTAG ATCCGGACAG AGGACGGTCA
GGCGCGCTCA CGACATGTTT TCTCTCTCTG ACCCTGCATC TAGGCCTGTC TCCTGCCAGT
```

```
UL138  2830                2840                2850                2860                2870                2880
       CCATGACGA TCTGCCGCTG AATGTCGGGT TACCCATCAT CGGCGTGATG CTCGTGCTGA
       GGTACCTGCT AGACGGCGAC TTACAGCCCA ATGGGTAGTA GCCGCACTAC GAGCACGACT
       2890                2900                2910                2920                2930                2940
       TCGTGGCCAT CCTCTGCTAT CTGGCTTACC ACTGGCACGA CACCTTCAAA CTGGTGCGCA
       AGCACCGGTA GGAGACGATA GACCGAATGG TGACCGTGCT GTGGAAGTTT GACCACGCGT
UL137
       2950                2960                2970                2980                2990                3000
       TGTTTCTGAG CTACCGCTGG CTGATCCGCT GTTGCGAGCT GCGGGGGAG TACGAGCGCC
       ACAAAGACTC GATGGCGACC GACTAGGCGA CAACGCTCGA CGCCCCCTC ATGCTCGCGG
       3010                3020                3030                3040                3050                3060
       GGTTCGCGGA CCTGTCGTCT CTGGGCCTCG GCGCCGTACG GCGGGAGTCG GACAGACGAT
       CCAAGCGCCT GGACAGCAGA GACCCGGAGC CGCGGCATGC CGCCCTCAGC CTGTCTGCTA
       3070                3080                3090                3100                3110                3120
       ACCGTTTCTC CGAACGGCCC GACGAGATCT TGGTCCGTTG GGAGGAAGTG TCTTCCCAGT
       TGGCAAAGAG GCTTGCCGGG CTGCTCTAGA ACCAGCCAAC CCTCCTTCAC AGAAGGGTCA
       3130                3140                3150                3160                3170                3180
       GCAGCTACGC GTCGTCGCGG ATAACAGACC GCCGTGTGCG TTCATCGTCT TCGTCGTCGG
       CGTCGATGCG CAGCAGCGCC TATTGTCTGG CGGCACACGC AAGTAGCAGA AGCAGCAGCC
       3190                3200                3210                3220                3230                3240
       TCCACGTCGC TAGCCAGAGA AACAGCGTGC CTCCGCCGGA CATGGCGGTG ACGGGCGCGC
       AGGTGCAGCG ATCGGTCTCT TTGTCGCACG GAGGCGGCCT GTACCGCCAC TGCCGCGGCG
       3250                3260                3270                3280                3290                3300
       TGACCGACGT CGATCTGTTG AAACCCGTGA CGGGATCCGC GACGCAGTTC ACCACCGTAG
       ACTGGCTGCA GCTAGACAAC TTTGGGCACT GCCCTAGGCG CTGCGTCAAG TGGTGGCATC
```

```
      3310       3320       3330       3340       3350       3360
CCATGGTACA TTATCATCAA GAGTACACGT GAATGAGAAA AAGAAAAAAG AGGGGAGCGG
GGTACCATGT AATAGTAGTT CTCATGTGCA CTTACTCTTT TTCTTTTTTC TCCCCTCGCC
                                ↑
                               UL138

3370       3380       3390       3400       3410       3420
ATCGCGATAA TGTCGCTTTG ACATTCTCTG CTCGATCTAC TCAGCGTCTG CACGAAACGG
TAGCGCTATT ACAGCGAAAC TGTAAGAGAC GAGCTAGATG AGTCGCAGAC GTGCTTTGCC 3430       3440       3450       3460       3470       3480
CATCCGCACG GAGGCGAGCC CAAGCGTATC TGCAGCAAGC GGTTCTTTCC CTCGGTGATG
GTAGGCGTGC CTCCGCTCGG GTTCGCATAG ACGTCGTTCG CCAAGAAAGG GAGCCACTAC 3490       3500       3510       3520       3530       3540
GTGGCAGCAT CGGTGGCGGG AGCTTGTTCG GACGATGGAC GGTGAGGAGT CCCTGGCGAT
CACCGTCGTA GCCACCGCCC TCGAACAAGC CTGCTACCTG CCACTCCTCA GGGACCGCTA 3550       3560       3570       3580       3590       3600
CAGGCGGCTC CCGGGTGTGG AGTTCAACGG GTGGTAATGG TGGCGGTGAT CGGTGTTAGA
GTCCGCCGAG GGCCCACACC TCAAGTTGCC CACCATTACC ACCGCCACTA GCCACAATCT 3610       3620       3630       3640       3650       3660
AAACGGTGGC CCTGGCAAAC ATATATCCCT TGTAAACCCT CTGCTCTGTT AATAAAAAGC
TTTGCCACCG GGACCGTTTG TATATAGGGA ACATTTGGGA GACGAGACAA TTATTTTTCG 3670       3680       3690       3700       3710       3720
ACACTTTTCA CATGAGTTCG TAATTTTATT GTGTAGTGGA AATTTTTACG TCATTGGGAA
TGTGAAAAGT GTACTCAAGC ATTAAAATAA CACATCACCT TTAAAAATGC AGTAACCCTT 3730       3740       3750       3760       3770       3780
ACCCCAGAAT GAAAGAGTAT AATGTGCATA TCACCGGGGG TTCCCTGTCA GTACGAATGT
TGGGGTCTTA CTTTCTCATA TTACACGTAT AGTGGCCCCC AAGGGACAGT CATGCTTACA
```

*FIG._1D-2*

```
        3790                3800                3810                3820                3830                3840
ACACAACGCG  GGTTACATTA  CGATAAACTT  TCCGGTAAAA  CGATGCCGAT  ACAGGCGTGTA
TGTGTTGCGC  CCAATGTAAT  GCTATTTGAA  AGGCCATTTT  GCTACGGCTA  TGTCGCACAT 3850                3860                3870                3880                3890                3900
TAACGCTGAT  TGTTACGACA  AACGAGTTGG  TATATCCATT  ATATAGTAAC  GAACATGCTG
ATTGCGACTA  ACAATGCTGT  TTGCTCAACC  ATATATCATT  TATATCATTG  CTTGTACGAC
                                                                  UL139

3910                3920                3930                3940                3950                3960
TGGATATTAG  TTTTATTTGC  ACTCGCCGCA  TCGGCGAGTG  AAACCACTAC  AGGTACCAGC
ACCTATAATC  AAAATAAACG  TGAGCGGCGT  AGCCGCTCAC  TTTGGTGATG  TCCATGGTCG 3970                3980                3990                4000                4010                4020
TCTAATTCCA  GTCAATCTAC  TAGTGCTACC  GCCAACACGA  CCGTATCGAC  ATGTATTAAT
AGATTAAGGT  CAGTTAGATG  ATCACGATGG  CGGTTGTGCT  GGCATAGCTG  TACATAATTA 4030                4040                4050                4060                4070                4080
GCCTCTAACG  GCAGTAGCTG  GACAGTACCA  CAGCTCGCGC  TGCTTGCCGC  TAGCGGCTGG
CGGAGATTGC  CGTCATCGAC  CTGTCATGGT  GTCGAGCGCG  ACGAACGGCG  ATCGCCGACC 4090                4100                4110                4120                4130                4140
ACATTATCTG  GACTCCTTCT  CTTATTTACC  TGCTGCTTTT  GCTGCTTTTG  GCTAGTACGT
TGTAATAGAC  CTGAGGAAGA  GAATAAATGG  ACGACGAAAA  CGACGAAAAC  CGATCATGCA 4150                4160                4170                4180                4190                4200
AAAATCTGCA  GCTGCTGCGG  CAACTCCTCC  GAGTCAGAGA  GCAAAACAAC  CCACGCGTAC
TTTTAGACGT  CGACGACGCC  GTTGAGGAGG  CTCAGTCTCT  CGTTTTGTTG  GGTGCGCATG 4210                4220                4230                4240                4250                4260
ACCAATGCCG  CATTCACTTC  TTCCGACGCA  ACGTTACCCA  TGGGCCACTAC  AGGGTCGTAC
TGGTTACGGC  GTAAGTGAAG  AAGGCTGCGT  TGCAATGGGT  ACCCGTGATG  TCCCAGCATG
```

FIG._1E-1

```
                4270       4280       4290       4300       4310       4320
           ACTCCCCCAC AGGACGGCTC ATTTCCACCT CCGCCCTCGGT GACGTAGGCT AAACCGAAAC
           TGAGGGGGTG TCCTGCCGAG TAAAGGTGGA GGCGGAGCCA CTGCATCCGA TTTGGCTTTG
                                                        UL139
                4330       4340       4350       4360       4370       4380
           CCACGTTGAA CCTAACGCGG TTTCGGAAGG CCTGAGACGT CACTTTCACA ATGACGTCCG
           GGTGCAACTT GGATTGCGCC AAAGCCTTCC GGACTCTGCA GTGAAAGTGT TACTGCAGGC 4390       4400       4410       4420       4430       4440
           TATACACGTT CATCATAAAA CACCGTAGAG GCTAAGGCTT CGGTAGGGAG AGACCTCAAC
           ATATGTGCAA GTAGTATTTT GTGGCATCTC CGATTCCGAA GCCATCCCTC TCTGGAGTTG 4450       4460       4470       4480       4490       4500
           TGTTCCTGAT GAGCACCCGT GCTCTCCATCT CTTCAGACTT GTCATGAGACCC CCGCTCAGAC
           ACAAGGACTA CTCGTGGGCA CGAGAGTAGA GAAGTCTGAA CAGTACTGGG GGCGAGTCTG
                                                   UL140
                4510       4520       4530       4540       4550       4560
           TAACGCGACT ACCACCGTGC ACCCGCACGA CGCAAAAAAC GGCAGCGGCG GTAGTGCCCT
           ATTGCGCTGA TGGTGGCACG TGGGCGTGCT GCGTTTTTTG CCGTCGCCGC CATCACGGGA 4570       4580       4590       4600       4610       4620
           GCCGACCCTC GTCGTTTTCG GCTTTATCGT TACGCTACTT TTCTTTCTCT TTATGCTCTA
           CGGCTGGGAG CAGCAAAAGC CGAAATAGCA ATGCGATGAA AAGAAAGAGA AATACGAGAT 4630       4640       4650       4660       4670       4680
           CTTTTGGAAC AACGACGTGT TCCGTAAGCT GCTCCGTGCG CTTGGATCCA GCGCTGTTGC
           GAAAACCTTG TTGCTGCACA AGGCATTCGA CGAGGCACGC GAACCTAGGT CGCGACAACG 4690       4700       4710       4720       4730       4740
           GACCGCTTCG ACGCGTGGCA AGACGAGGTC ATCTACCGTC GTCCATCACG TCGTTCCCAG
           CTGGCGAAGC TGCGCACCGT TCTGCTCCAG TAGATGGCAG CAGGTAGTGC AGCAAGGGTC
```

FIG._1E-2

FIG._1F-1

```
5230       5240       5250       5260       5270       5280
TCAGTTGCGG GCATCCCGGG CGAGAAGCTG CGTCGCACGG TGGTCACCAC CACGCCGGCC
AGTCAACGCC CGTAGGGCCC GCTCTTCGAC GCAGCGTGCC ACCAGTGGTG GTGCGGCCGG 5290       5300       5310       5320       5330       5340
CGACGTTTGA GCGGCCGACA CACGGAGCAG GAGCAGGCGG GCATGCGTCT CTGTGAAAAA
GCTGCAAACT CGCCGGCTGT GTGCCTCGTC CTCGTCCGCC CGTACGCAGA GACACTTTTT 5350       5360       5370       5380       5390       5400
GGGAAGAAAA GAATCATCAT GTGCCGCCGG GAGTCGCTCC GAACTCTGCC GTGGCTGTTC
CCCTTCTTTT CTTAGTAGTA CACGGCGGCC CTCAGCGAGG CTTGAGACGG CACCGACAAG 5410       5420       5430       5440       5450       5460
TGGGTGCTGT TGAGCTGCCC GCGACTCCTC GAATATTCTT CCTCTTCGTT CCCCTTCGCC
ACCCACGACA ACTCGACGGG CGCTGAGGAG CTTATAAGAA GGAGAAGCAA GGGGAAGCGG 5470       5480       5490       5500       5510       5520
ACCGCTGACA TTGCCGAAAA GATGTGGGCC GAGAATTATG AGACCACGTC GCCGGCGCCG
TGGCGACTGT AACGGCTTTT CTACACCCGG CTCTTAATAC TCTGGTGCAG CGGCCGCGGC 5530       5540       5550       5560       5570       5580
GTGTTGGTCG CCGAGGGAGA GCAAGTTACC ATCCCCTGCA CGGTCATGAC ACACTCCTGG
CACAACCAGC GGCTCCCTCT CGTTCAATGG TAGGGGACGT GCCAGTACTG TGTGAGGACC 5590       5600       5610       5620       5630       5640
CCCATGGTCT CCATTCGCGC ACGTTTCTGT CGTTCCCACG ACGGCAGCGA CGAGCTCATC
GGGTACCAGA GGTAAGCGCG TGCAAAGACA GCAAGGGTGC TGCCGTCGCT GCTCGAGTAG
```

*FIG._1F-2*

```
5650        5660        5670        5680        5690        5700
CTGGACGCCG  TCAAAGGCCA  TCGGCTGATG  AACGGACTCC  AGTACCGCCT  GCCGTACGCC
GACCTGCGGC  AGTTTCCGGT  AGCCGACTAC  TTGCCTGAGG  TCATGGCGGA  CGGCATGCGG 5710        5720        5730        5740        5750        5760
ACTTGGAATT  TCTCGCAATT  GCATCTCGGC  CAAATATTCT  CGCTTACTTT  TAACGTATCG
TGAACCTTAA  AGAGCGTTAA  CGTAGAGCCG  GTTTATAAGA  GCGAATGAAA  ATTGCATAGC 5770        5780        5790        5800        5810        5820
ATGGACACAG  CCGGCATGTA  CGAATGCGTG  CTACGCAACT  ACAGCCACGG  CCTCATCATG
TACCTGTGTC  GGCCGTACAT  GCTTACGCAC  GATGCGTTGA  TGTCGGTGCC  GGAGTAGTAC 5830        5840        5850        5860        5870        5880
CAACGCTTCG  TAATTCTCAC  GCAGCTGGAG  ACGCTCAGCC  GGCCCGACGA  ACCTTGCTGC
GTTGCGAAGC  ATTAAGAGTG  CGTCGACCTC  TGCGAGTCGG  CCGGGCTGCT  TGGAACGACG 5890        5900        5910        5920        5930        5940
ACACCGGCGT  TAGGTCGCTA  CTCGCTGGGA  GACCAGATCT  GGTCGCCGAC  GCCCTGGCGT
TGTGGCCGCA  ATCCAGCGAT  GAGCGACCCT  CTGGTCTAGA  CCAGCGGCTG  CGGGACCGCA 5950        5960        5970        5980        5990        6000
CTACGGAATC  ACGACTGCGG  AACGTACCGC  GGCTTTCAAC  GCAACTACTT  CTATATCGGC
GATGCCTTAG  TGCTGACGCC  TTGCATGGCG  CCGAAAGTTG  CGTTGATGAA  GATATAGCCG 6010        6020        6030        6040        6050        6060
CGCGCCGACG  CCGAGGATTG  CTGGAAACCC  GCATGTCCGG  ACGAGGAACC  CGACCGCTGT
GCGCGGCTGC  GGCTCCTAAC  GACCTTTGGG  CGTACAGGCC  TGCTCCTTGG  GCTGGCGACA 6070        6080        6090        6100        6110        6120
TGGACAGTGA  TACAGCGTTA  CCGGCTCCCC  GGCGACTGCT  ACCGTTCGCA  GCCACACCCG
ACCTGTCACT  ATGTCGCAAT  GGCCGAGGGG  CCGCTGACGA  TGGCAAGCGT  CGGTGTGGGC
```

*FIG._1G-1*

```
     6130           6140           6150           6160           6170           6180
CCGAAATTTT TACCGGTGAC GCCAGCACCG CCGGCCGACA TAGACACCGG GATGTCTCCC
GGCTTTAAAA ATGGCCACTG CGGTCGTGGC GGCCGGCTGT ATCTGTGGCC CTACAGAGGG 6190           6200           6210           6220           6230           6240
TGGGCCACTC GGGGAATCGC GGCGTTTTTG GGGTTTTGGA GTATTTTTAC CGTATGTTTC
ACCCGGTGAG CCCCTTAGCG CCGCAAAAAC CCCAAAACCT CATAAAAATG GCATACAAAG 6250           6260           6270           6280           6290           6300
CTATGCTACC TGTGTTATCT GCAGTGTTGT GGACGCTGGT GTCCCACGCC GGGAAGGGGA
GATACGATGG ACACAATAGA CGTCACAACA CCTGCGACCA CAGGGTGCGG CCCTTCCCCT 6310           6320           6330           6340           6350           6360
CGACGAGGCG GTGAGGGCTA TCGACGCCTA CCGACTTACG ATAGTTACCC CGGTGTTAGA
GCTGCTCCGC CACTCCCGAT AGCTGCGGAT GGCTGAATGC TATCAATGGG GCCACAATCT

6370    UL141  6380           6390           6400    6450 UL142 6460         6420
AAGATGAAGA GGTGAGAACA CGTATAAAAT AAAAAAAATAA TTAAAAATATG CGGATTGAAT
TTCTACTTCT CCACTCTTGT GCATATTTTA TTTTTTTATT AATTTTATAC GCCTAACTTA 6430           6440                          6410                           6480
GTGAAGTGTG AATAGTGTGA                    TATGTTAAAA AATGCAGTGT GTTATTCGGA
CACTTCACAC TTATCACACT                    ATACAATTTT TTACGTCACA CAATAAGCCT 6490           6500           6510           6520           6530           6540
TACTTTGTGT CATCCGTTGG GAGCGAACGG TCATTATCCT ATCGTTACCA CTTGGAATCT
ATGAAACACA GTAGGCAACC CTCGCTTGCC AGTAATAGGA TAGCAATGGT GAACCTTAGA 6550           6560           6570           6580           6590           6600
AATTCATCTA CCAACGTGGT TTGCAACGGA AACATTCCG TGTTTGTAAA CGGCACCCTA
TTAAGTAGAT GGTTGCACCA AACGTTGCCT TTGTAAGGC ACAAACATTT GCCGTGGGAT
```

FIG._1G-2

| | | | | | |
|---|---|---|---|---|---|
| 6610 | 6620 | 6630 | 6640 | 6650 | 6660 |
| GGTGTGCGGT | ATAACATTAC | GGTAGGAATC | AGTTCGTCTT | TATTAATAGG | ACACCTTACT |
| CCACACGCCA | TATTGTAATG | CCATCCTTAG | TCAAGCAGAA | ATAATTATCC | TGTGGAATGA |
| 6670 | 6680 | 6690 | 6700 | 6710 | 6720 |
| ATACAAGTAT | TGGAATCATG | GTTCACACCC | TGGGTCCAAA | ATAAAAGTTA | CAACAAACAA |
| TATGTTCATA | ACCTTAGTAC | CAAGTGTGGG | ACCCAGGTTT | TATTTTCAAT | GTTGTTTGTT |
| 6730 | 6740 | 6750 | 6760 | 6770 | 6780 |
| CCCCTAGGTG | ACACTGAAAC | GCTTTATAAT | ATAGATAGCG | AAAACATTCA | TCGCGTATCT |
| GGGGATCCAC | TGTGACTTTG | CGAAATATTA | TATCTATCGC | TTTTGTAAGT | AGCGCATAGA |
| 6790 | 6800 | 6810 | 6820 | 6830 | 6840 |
| CAATATTTTC | ACACAAGATG | GATAAAATCT | CTGCAAGAGA | ATCACACTTG | CGACCTCACA |
| GTTATAAAAG | TGTGTTCTAC | CTATTTTAGA | GACGTTCTCT | TAGTGTGAAC | GCTGGAGTGT |
| 6850 | 6860 | 6870 | 6880 | 6890 | 6900 |
| AACAGTACAC | CTACCTATAC | ATATCAAGTA | AACGTGAACA | ACACGAATTA | CCTAACACTA |
| TTGTCATGTG | GATGGATATG | TATAGTTCAT | TTGCACTTGT | TGTGCTTAAT | GGATTGTGAT |
| 6910 | 6920 | 6930 | 6940 | 6950 | 6960 |
| ACATCCTCGG | GATGGCAAGA | CCGTCTAAAT | TACACCGTCA | TAAATAGTAC | ACACTTTAAC |
| TGTAGGAGCC | CTACCGTTCT | GGCAGATTTA | ATGTGGCAGT | ATTTATCATG | TGTGAAATTG |
| 6970 | 6980 | 6990 | 7000 | 7010 | 7020 |
| CTCACAGAAT | CGAACATAAC | CAGCATTCAA | AAATATCTCA | ACACTACCTG | CATAGAAAGA |
| GAGTGTCTTA | GCTTGTATTG | GTCGTAAGTT | TTTATAGAGT | TGTGATGGAC | GTATCTTTCT |
| 7030 | 7040 | 7050 | 7060 | 7070 | 7080 |
| CTCCGTAACT | ACACCTTGGA | GTCCGTATAC | ACCACAACTG | TGCCTCAAAA | CATAACAACA |
| GAGGCATTGA | TGTGGAACCT | CAGGCATATG | TGGTGTTGAC | ACGGAGTTTT | GTATTGTTGT |

```
7090        7100        7110        7120        7130        7140
TCTCAACACG  CAACAACCAC  TATGCACACA  ATACCTCCAA  ATACAATAAC  AATTCAAAAT
AGAGTTGTGC  GTTGTTGGTG  ATACGTGTGT  TATGGAGGTT  TATGTTATTG  TTAAGTTTTA 7150        7160        7170        7180        7190        7200
ACAACTCAAA  GCCATACTGT  ACAGACGCCG  TCTTTTAACG  ACACACATAA  CGTGACGAAA
TGTTGAGTTT  CGGTATGACA  TGTCTGCGGC  AGAAAATTGC  TGTGTGTATT  GCACTGCTTT 7210        7220        7230        7240        7250        7260
CACACGTTAA  ACATAAGCTA  CGTTTTATCA  CAAAAAACGA  ATAACACAAC  ATCACCGTGG
GTGTGCAATT  TGTATTCGAT  GCAAAATAGT  GTTTTTTGCT  TATTGTGTTG  TAGTGGCACC 7270        7280        7290        7300        7310        7320
ATATATGCCA  TACCTATGGG  CGCTACAGCC  ACAATAGGCG  CCGGTTTATA  TATCGGGAAA
TATATACGGT  ATGGATACCC  GCGATGTCGG  TGTTATCCGC  GGCCAAATAT  ATAGCCCTTT 7330        7340        7350   UL143 7360  UL142 7370       7380
CACTTTACGC  CGGTTAAGTT  CGTATACGAG  GTATGGCGCG  GTCAGTAAAG  ACGATTCGGA
GTGAAATGCG  GCCAATTCAA  GCATATGCTC  CATACCGCGC  CAGTCATTTC  TGCTAAGCCT 7390        7400        7410        7420        7430        7440
TTCAACACAT  ATACTCCCCA  CGATCCTCGA  ACACCTTACA  GCATATGAGC  AAAAAACAAG
AAGTTGTGTA  TATGAGGGGT  GCTAGGAGCT  TGTGGAATGT  CGTATACTCG  TTTTTTGTTC 7450        7460        7470        7480        7490        7500
AAAGTATAGC  CACAATCACA  TTTGGGCGAA  TAACATGCTG  TCATCCACTA  GCGTCTATTA
TTTCATATCG  GTGTTAGTGT  AAACCCGCTT  ATTGTACGAC  AGTAGGTGAT  CGCAGATAAT 7510        7520        7530        7540        7550        7560
ATCTAATGTT  TAACGGGAGC  TGTACTGTCA  CCGTTAAAAT  ATCCATGGGA  ATCAACGGGT
TAGATTACAA  ATTGCCCTCG  ACATGACAGT  GGCAATTTTA  TAGGTACCCT  TAGTTGCCCA
```

```
              7570                7580                7590                7600                7610                7620
      CAACCAACGT          CCATCAGCTT          GTGATTGTGC          TCCATCTGGG          TAACCGCTGT          CAGCCTTGGC
      GTTGGTTGCA          GGTAGTCGAA          CACTAACACG          AGGTAGACCC          ATTGGCGACA          GTCGGAACCG
UL143         7630                7640                7650                7660                7670                7680
      GACAGGTGTA ATCACAGCTG          TCACATAACT          CACGAAGCCT          CCAATCACAG          CAGCACACAT
      CTGTCCACAT TAGTGTCGAC          AGTGTATTGA          GTGCTTCGGA          GGTTAGTGTC          GTCGTGTGTA
              7690                7700                7710                7720                7730                7740
      AGTCCTAACG          CCATTGGCGT          GTATAAAAGT          TCGGAAAAACT          TGACGGTTGT          ACGGCACGAC
      TCAGGATTGC          GGTAACCGCA          CATATTTTCA          AGCCTTTTGA          ACTGCCAACA          TGCCGTGCTG
              7750                7760                7770                7780                7790                7800
      AAATCGATGT          AGTGGTATGT          TTTTCCAGCA          GAGACCGTGT          GCGGTCTCTT          AGGTTCGCTA
      TTTAGCTACA          TCACCATACA          AAAAGGTCGT          CTCTGGCACA          CGCCAGAGAA          TCCAAGCGAT
              7810                7820                7830                7840                7850                7860
      TACTGTGGCT          GGAAACTGGT          TACCTGTGAA          GATGGCTAAC          TATCCTGTTC          TGTCCTGGAA
      ATGACACCGA          CCTTTGACCA          ATGGACACTT          CTACCGATTG          ATAGGACAAG          ACAGGACCTT
              7870                7880                7890                7900                7910                7920
      AAACTTTTGG          CGTCGTAGGT          GGACTTTGCA          GTATGCGGGT          TAGTGAAGTT          ATGTCATTTA
      TTTGAAAACC          GCAGCATCCA          CCTGAAACGT          CATACGCCCA          ATCACTTCAA          TACAGTAAAT
              7930                7940                7950                7960                7970                7980
      TTTACGTTTA          CGATCTCGTA          TTACAAACCG          CGGAGAGGAT          GATACCGTTC          GGCCCCATGA
      AAATGCAAAT          GCTAGAGCAT          AATGTTTGGC          GCCTCTCCTA          CTATGGCAAG          CCGGGGTACT
              7990                8000         8010 UL144 8020                8030                8040
      GTTATTTTTA          TTCTTTCCGGT          AGGAGGCATG AAGCCCTCTGA          TAATGCTCAT          CTGCTTTGCT
      CAATAAAAAT          AAGAAGGCCA          TCCTCCGTAC TTCGGAGACT          ATTACGAGTA          GACGAAACGA
```

FIG._1I-1

```
                                                            8050                 8060                 8070                 8080                 8090                 8100
                                                  GTGATATTAT           TGCAGCTTGG           AGTGACTAAA           GTGTGTCAGC           ATAATGAAGT           GCAACTGGGC
                                                  CACTATAATA           ACGTCGAACC           TCACTGATTT           CACACAGTCG           TATTACTTCA           CGTTGACCCG
                                                            8110                 8120                 8130                 8140                 8150                 8160
                                                  AATGAGTGCT           GCCCTCCGTG           TGGTTCGGGA           CAAAGAGTTA           CTAAAGTATG           CACGGATTAT
                                                  TTACTCACGA           CGGGAGGCAC           ACCAAGCCCT           GTTTCTCAAT           GATTTCATAC           GTGCCTAATA
                                                            8170                 8180                 8190                 8200                 8210                 8220
                                                  ACCAGTGTAA           CGTGTACCCC           TTGCCCCAAC           GGCACGTATG           TATCGGGACT           TTACAACTGT
                                                  TGGTCACATT           GCACATGGGG           AACGGGGTTG           CCGTGCATAC           ATAGCCCTGA           AATGTTGACA
                                                            8230                 8240                 8250                 8260                 8270                 8280
                                                  ACCGATTGCA           CTCAATGTAA           CGTCACTCAG           GTCATGATTC           GTAACTGCAC           TTCCACCAAT
                                                  TGGCTAACGT           GAGTTACATT           GCAGTGAGTC           CAGTACTAAG           CATTGACGTG           AAGGTGGTTA
                                                            8290                 8300                 8310                 8320                 8330                 8340
                                                  AATACCGTAT           GCGCACCTAA           GAACCATACG           TACTTTTCCA           CTCCAGGCGT           CCAACATCAC
                                                  TTATGGCATA           CGCGTGGATT           CTTGGTATGC           ATGAAAAGGT           GAGGTCCGCA           GGTTGTAGTG
                                                            8350                 8360                 8370                 8380                 8390                 8400
                                                  AGCAAAATCA           TACCGCACAT           ATAACCGTCA           ATAACCGTCA           AACAAGGAAA           AAGCGGTCGT
                                                  TCGTTTTAGT           ATGGCGTGTA           TATTGGCAGT           TATTGGCAGT           TTGTTCCTTT           TTCGCCAGCA
                                                            8410                 8420                 8430                 8440                 8450                 8460
                                                  CATACTCTAG           CCTGGTTGTC           TCTCTTTATC           TTTCTGTGTG           GTATCATACT           TTTAATTCTC
                                                  GTATGAGATC           GGACCAACAG           AGAGAAATAG           AAAGAACACC           CATAGTATGA           AAATTAAGAG
                                                            8470                 8480                 8490                 8500                 8510                 8520
                                                  TATCTTATAG           CCGCCTATCG           GAGTGAGAGA           TGCCAACAGT           GTTGCTCAAT           CGGCAAAATT
                                                  ATAGAATATC           GGCGGATAGC           CTCACTCTCT           ACGGTTGTCA           CAACGAGTTA           GCCGTTTTAA
```

FIG._1I-2

```
                                                        8570        8580
    8530                  UL144  8540        8550        8560  TCACGGTACG  ATGAAGTCAC
TTCTACCGCA  CCTGTGTAAGC  TTCCTGTTGT  TGTTTTTACA  AGTGCCATGC  TACTTCAGTG
AAGATGGCGT  GGGACATTCG  AAGGACAACA  ACAAAAATGT 8590        8600        8610        8620        8630        8640
ACAGATAATT  ACAGATGAGC  TGTTCATATT  TTTTATTATT  TTTTCCAATT  CCTGCACTAA
TGTCTATTAA  TGTCTACTCG  ACAAGTATAA  AAAATAATAA  AAAAGGTTAA  GGACGTGATT 8650        8660        8670        8680        8690        8700
AAAAAGAAGC  ACTTTACGGA  ACCGTGTCTG  AGTATCTGTG  GGGAATTTAG  GTACTTTTTG
TTTTCTTCG   TGAAATGCCT  TGGCACAGAC  TCATAGACAC  CCCTTAAATC  CATGAAAAAC 8710        8720        8730        8740        8750        8760
CCGACGTCAG  GAAAAATAAG  TGTCGCCTAC  ATAAGAGCCC  GGTGCTATCG  TGCTGTCACT
GGCTGCAGTC  CTTTTTATTC  ACAGCGGATG  TATTCTCGGG  CCACGATAGC  ACGACAGTGA 8770        8780        8790        8800        8810        8820
CTTTCTTGTT  GCCTTCGATG  TACGGCGTCC  TGGCTCATTA  CTACTCCTTC  ATCAGTAGCC
GAAAGAACAA  CGGAAGCTAC  ATGCCGCAGG  ACCGAGTAAT  GATGAGGAAG  TAGTCATCGG 8830        8840        8850        8860  8870  UL145  8880
CCAGCGTTAT  GGTTAATTTT  AAGCATCATA  ACGCCGTGCA  GCTGTTATGT  GCACGGACCC
GGTCGCAATA  CCAATTAAAA  TTCGTAGTAT  TGCGGCACGT  CGACAATACA  CGTGCCTGGG 8890        8900        8910        8920        8930        8940
GAGACGCACT  GCCGGATGGG  AACGTTTAAC  CCATCATGCG  TCGTATCACG  CGAACTACGG
CTCTGCGTGA  CGGCCTACCC  TTGCAAATTG  GGTAGTACGC  AGCATAGTGC  GCTTGATGCC 8950        8960        8970        8980        8990        9000
GGCATACGCC  GTGTTGATGG  CTACATCGCA  AAGAAAGTCC  CTAGTGTTAC  ATCGATACAG
CCGTATGCGG  CACAACTACC  GATGTAGCGT  TTCTTTCAGG  GATCACAATG  TAGCTATGTC
```

*FIG._1J-1*

```
      9010                9020                9030                9040                9050                9060
TGCCGTGACA  GCCGTGGCCC  TGCAGCTCAT  GCCTGTTGAG  ATCGTCCGCA  AGCTAGATCA
ACGGCACTGT  CGGCACCGGG  ACGTCGAGTA  CGGACAACTC  TAGCAGGCGT  TCGATCTAGT 9070                9080                9090                9100                9110                9120
GTCGGACTGG  GTGCGGGGTG  CCTGGATCGT  GTCAGAGACT  TTTCCAACTA  GCGACCCCAA
CAGCCTGACC  CACGCCCCAC  GGACCTAGCA  CAGTCTCTGA  AAAGGTTGAT  CGCTGGGGTT 9130                9140                9150            UL145 9170              9180
AGGAGTTTGG  AGCGACGATG  ACTCCTCGAT  GGGTGGAAGT  GATGATTGAT  GATGAGAACC
TCCTCAAACC  TCGCTGCTAC  TGAGGAGCTA  CCCACCTTCA  CTACTAACTA  CTACTCTTGG 9190                9200                9210                9220                9230                9240
TGACAAGAAA  GACGAGAGAG  AAATTTAGAG  CTGTCATTGT  AGAATTAGTC  TAGATTCCTG
ACTGTTCTTT  CTGCTCTCTC  TTTAAATCTC  GACAGTAACA  TCTTAATCAG  ATCTAAGGAC 9250                9260                9270                9280                9290                9300
ATAATAAACA  GTATCGATTT  TGAAACCTAA  TTGACGTGTG  ATCGATTTTT  AAACCTCTGT
TATTATTTGT  CATAGCTAAA  ACTTTGGATT  AACTGCACAC  TAGCTAAAAA  TTTGGAGACA 9310                9320                9330                9340                9350                9360
GTTGTGTGAT  TGATTGGTAT  GTGGGGGAT  CCGATTTCAA  AGGGGGGTAC  TTATCGGAA
CAACACACTA  ACTAACACTA  CACCCCCCTA  GGCTAAAGTT  TCCCCCCATG  AATAGCCCTT 9370                9380                9390                9400                9410                9420
TTGATGTGTC  ATGGACGCAG  TTTGAGCCGA  TTTTCCGGGA  ATACCGGATA  TTACGAATTA
AACTACACAG  TACCTGCGTC  AAACTCGGCT  AAAAGGCCCT  TATGGCCTAT  AATGCTTAAT
```

FIG._1J-2

```
       9430                9440                9450  UL146   9460                9470                9480
CTGGTAGTGA          AAAATTATAA          TGCGATTAAT          TTTTGGTGCG          TTGATTATTT
GACCATCACT          TTTTAATATT          ACGCTAATTA          AAAACCACGC          AACTAATAAA
CGTAGAGATAAT 9490                9500                9510                9520                9530                9540
TTTTAGCATA          TATGAGGTGA          ATGGAACAGA          ATTACGCTGC          AGATGTCTTC
AAAATCGTAT          ATACTCCACT          TACCTTGTCT          TAATGCGACG          TCTACAGAAG
TGTGTATCAT 9550                9560                9570                9580                9590                9600
ATAGAAAATG          AAAATTATAT          TGGGTAATTA          TTGGCTTCAT          CGCGATCCCA
TATCTTTTAC          TTTTAATATA          ACCCATTAAT          AACCGAAGTA          GCGCTAGGGT
GCCGCCTAAT 9610                9620                9630                9640                9650                9660
GAGGGCCCGG          AATGAACATT          TATTGTATCC          AGACGGAAGG          AAACCGCCTG
CTCCCGGGCC          TTACTTGTAA          ATAACATAGG          TCTGCCTTCC          TTTGGCGGAC
ATGCGATAAA 9670                9680                9690                9700                9710                9720
GACCTGGAGT          CCCGATCACC          TCTTCTCAAA          ATGGTTAGAC          AAACACAACG
CTGGACCTCA          GGGCTAGTGG          AGAAGAGTTT          TACCAATCTG          TTTGTGTTGC
ATGTTTATCG 9730                9740                9750                9760                9770                9780
ATAATAGGTG          AACATAACGA          TTAGTGGTCC          ACCGAGACGA          ATAAATATAA
TATTATCCAC          TTGTATTGCT          AATCACCAGG          TGGCTCTGCT          TATTTATATT
GTATAATGTT 9790                9800  UL146        9810                9820                9830                9840
CCTTGATAGG          TAA TATTTAA          TGTATGTTTT          CAAACAGACA          AGTTCGTTAA
GGAACTATCC          ATT ATAAATT          ACATACAAAA          GTTTGTCTGT          TCAAGCAATT
TGTTAGAGA 9850                9860                9870  UL147  9880                9890                9900
AACAAAATAT          GTTTAATA ATG          GTGCTAACAT          GGTTGCACCA          TCCGGTTTCA
TTGTTTTATA          CAAATTAT TAC          CACGATTGTA          CCAACGTGGT          AGGCCAAAGT
TACAGTATGT          ATGTCATACA          
```

FIG._1K-1

```
             9910           9920           9930           9940           9950           9960
       AACTCGCATA     TCAATCTGTT     ATCGGTACGA     CACCTGTCAT     TAATCGCATA     TATGTTACTT
       TTGAGCGTAT     AGTTAGACAA     TAGCCATGCT     GTGGACAGTA     ATTAGCGTAT     ATACAATGAA 9970           9980           9990          10000          10010          10020
       ACCATATGTC     CCCTAGCCGT     CCATGTTTTA     GAACTAGAAG     ATTACGACAG     GCGCTGCCGT
       TGGTATACAG     GGGATCGGCA     GGTACAAAAT     CTTGATCTTC     TAATGCTGTC     CGCGACGGCA 10030          10040          10050          10060          10070          10080
       TGCAACAACC     AAATTCTGTT     GAATACCCTG     CCGGTCGGAA     CCGAATTGCT     TAAGCCAATC
       ACGTTGTTGG     TTTAAGACAA     CTTATGGGAC     GGCCAGCCTT     GGCTTAACGA     ATTCGGTTAG 10090          10100          10110          10120          10130          10140
       GCAGCGAGCG     AAAGCTGCAA     TCGTCAGGAA     GTGCTGGCTA     TTTTAAAGGA     CAAGGAACC
       CGTCGCTCGC     TTTCGACGTT     AGCAGTCCTT     CACGACCGAT     AAAATTTCCT     GTTCCCTTGG 10150          10160          10170          10180          10190          10200
       AAGTGTCTCA     ATCCTAACGC     GCAAGCCGTG     CGTCGTCACA     GACGTAGTGT     ATTTTTTCGG
       TTCACAGAGT     TAGGATTGCG     CGTTCGGCAC     GCAGCAGTGT     CTGCATCACA     TAAAAAAGCC 10210          10220          10230          10240          10250          10260
       TTAATCTTAG     ACGAGGAACA     ACGCATTTAC     CTACCAATAT     TGAGTTCGGT     TGAGTTCGGT
       AATTAGAATC     TGCTCCTTGT     TGCGTAAATG     GATGGTTATA     ACTCAAGCCA     ACTCAAGCCA 10270          10280          10290          10300          10310          10320
       GCCTGGCCAG     TCCCTACGGC     CTACAAAGCC     TTTCTTTGGA     AATACGCCAA     GAGACTGAAC
       CGGACCGGTC     AGGGATGCCG     GATGTTTCGG     AAAGAAACCT     TTATGCGGTT     CTCTGACTTG 10330          10340      UL147 10350          10360          10370          10380
       TACCACCACT     TCAGACTGCG     CTGGTGATCA     TGTCCCTATT     TTACCGTGCG     GTAGCTCTGG
       ATGGTGGTGA     AGTCTGACGC     GACCACTAGT     ACAGGGATAA     AATGGCACGC     CATCGAGACC
```

FIG._1K-2

| | | | | | |
|---|---|---|---|---|---|
| 10390 | 10400 | 10410 | 10420 | 10430 | 10440 |
| GCACGCTAAG | CGCTTTGGTG | TGGTACAGCA | CTAGCATCCT | CGCAGAGATT | AACGAAAATT |
| CGTGCGATTC | GCGAAACCAC | ACCATGTCGT | GATCGTAGGA | GCGTCTCTAA | TTGCTTTTAA |
| 10450 | 10460 | 10470 | 10480 | 10490 | 10500 |
| CCTGCTCCTC | ATCTTCTGCG | GATCACGAAG | ACTGCGAGGA | ACCGGACGAG | ATCGTTCGCG |
| GGACGAGGAG | TAGAAGACGC | CTAGTGCTTC | TGACGCTCCT | TGGCCTGCTC | TAGCAAGCGC |
| 10510 | 10520 | 10530 | 10540 | 10550 | 10560 |
| AAGAGCAAGA | CTATCGGGCT | CTGCCTGGCT | TTTCCCTAGT | GATTTGCGGT | ACGCTCCTCG |
| TTCTCGTTCT | GATAGCCCGA | GACGACCCGA | AAAGGGATCA | CTAAACGCCA | TGCGAGGAGC |
| 10570 | 10580 | 10590 | 10600 | 10610 | 10620 |
| TCACTTGTGT | GATCTGAGAC | GTCATGCTGG | TAGCGTTTAT | GAGTCGGGCG | GTGGCCGACA |
| AGTGAACACA | CTAGACTCTG | CAGTACGACC | ATCGCAAATA | CTCAGCCCGC | CACCGGCTGT |
| 10630 | 10640 | 10650 UL148 | 10660 | 10670 | 10680 |
| CGCCCGCATTT | CCTAACCCGC | GCAGCATGTT | GCGCTTGCTG | TTCACGCTCG | TCCTGCTGGC |
| GCGGCGTAAA | GGATTGGGCG | CGTCGTACAA | CGCGAACGAC | AAGTGCGAGC | AGGACGACCG |
| 10690 | 10700 | 10710 | 10720 | 10730 | 10740 |
| CCTTCCACGGG | CAGTCTGTCG | GCGCTAGCCG | CGACTATGTG | CATGTTCGGC | TACTGAGCTA |
| GGAGGTGCCC | GTCAGACAGC | CGCGATCGGC | GCTGATACAC | GTACAAGCCG | ATGACTCGAT |
| 10750 | 10760 | 10770 | 10780 | 10790 | 10800 |
| CCGAGGCGAC | CCCCTGGTCT | TCAAGCACAC | TTTCTCGGGT | GTGCGTCGAC | CCTTCACCGA |
| GGCTCCGCTG | GGGGACCAGA | AGTTCGTGTG | AAAGAGCCCA | CACGCAGCTG | GGAAGTGGCT |
| 10810 | 10820 | 10830 | 10840 | 10850 | 10860 |
| GCTAGGCTGG | GCTGCCGTGTC | GCGACTGGGA | CAGTATGCAT | TGCACACCCT | TCTGGTCTAC |
| CGATCCGACC | CGACGCACAG | CGCTGACCCT | GTCATACGTA | ACGTGTGGGA | AGACCAGATG |

FIG._1L-1

```
      10870           10880           10890           10900           10910           10920
CGATCTGGAG CAGATGACCG ACTCGGTGCG GCGTTACAGC ACGGTGAGCC CCGGCAAGGA
GCTAGACCTC GTCTACTGGC TGAGCCACGC CGCAATGTCG TGCCACTCGG GGCCGTTCCT 10930           10940           10950           10960           10970           10980
AGTGACGCTT CAGCTTCACG GGAACCAAAC CGTACAGCCG TCGTTTCTAA GCTTTACGTG
TCACTGCGAA GTCGAAGTGC CCTTGGTTTG GCATGTCGGC AGCAAAGATT CGAAATGCAC 10990           11000           11010           11020           11030           11040
CCGCCTGCAG CTAGAACCCG TGGTGGAAAA TGTTGGCCTC TACGTGGCCT ACGTGGTCAA
GGCGGACGTC GATCTTGGGC ACCACCTTTT ACAACCGGAG ATGCACCGGA TGCACCAGTT 11050           11060           11070           11080           11090           11100
CGACGGGCGAA CGCCCACAAC AGTTTTTTAC ACCGCAGGTA GACGTGGTAC GCTTTGCTCT
GCTGCCGCTT GCGGGTGTTG TCAAAAAATG TGGCGTCCAT CTGCACCATG CGAAACGAGA 11110           11120           11130           11140           11150           11160
ATATCTAGAA ACACTCTCCC GGATCGTGGA ACCGTTAGAA TCAGGTCGCC TGGCAGTGGA
TATAGATCTT TGTGAGAGGG CCTAGCACCT TGGCAATCTT AGTCCAGCGG ACCGTCACCT 11170           11180           11190           11200           11210           11220
ATTTGATACG CCTGACCTAG CTCTGGCGCC CGATTTAGTA AGCAGCCTCT TCGTGGCCGG
TAAACTATGC GGACTGGATC GAGACCGCGG GCTAAATCAT TCGTCGGAGA AGCACCGGCC 11230           11240           11250           11260           11270           11280
ACACGGCGAG ACCGACTTTT ACATGAACTG GACGCTGCGT CGCAGTCAGA CCCACTACCT
TGTGCCGCTC TGGCTGAAAA TGTACTTGAC CTGCGACGCA GCGTCAGTCT GGGTGATGGA 11290           11300           11310           11320           11330           11340
GGAGGAGATG GCCTTACAGG TGGAGATTCT AAAACCCCGC GGCGTACGTC ACCGCGCTAT
CCTCCTCTAC CGGAATGTCC ACCTCTAAGA TTTTGGGGCG CCGCATGCAG TGGCGCGATA
```

FIG._1L-2

```
        11350                11360                11370                11380                11390                11400
TATCCACCAT           CCGAAGCTAC           AGCCGGGCGT           TGGCCTGTGG           ATAGATTTCT           GCGTGTACCG
ATAGGTGGTA           GGCTTCGATG           TCGGCCCGCA           ACCGGACACC           TATCTAAAGA           CGCACATGGC 11410                11420                11430                11440                11450                11460
CTACAACGCG           CGCCTGACCC           GCGGCTACGT           ACGATACACC           CTGTCACCGA           AAGCCGCTT
GATGTTGCGC           GCGGACTGGG           CGCCGATGCA           TGCTATGTGG           GACAGTGGCT           TTCGGCGAA 11470                11480                11490                11500                11510                11520
GCCCGCAAAA           GCAGAGGGTT           GGCTGGTGTC           ACTAGACAGA           TTCATCGTGC           AGTACCTCAA
CGGGCGTTTT           CGTCTCCCAA           CCGACCACAG           TGATCTGTCT           AAGTAGCACG           TCATGGAGTT 11530                11540                11550                11560                11570                11580
CACATTGCTG           ATTACAATGA           TGGCGGCGAT           ATGGGCTCGC           GTTTTGATAA           CCTACCTGGT
GTGTAACGAC           TAATGTTACT           ACCGCCGCTA           TACCCGAGCG           CAAAACTATT           GGATGGACCA

UL148 11590          11600                11610                11620                11630                11640
GTCGCGGCGT           CGGTAGAGGC           TTGCGGAAAC           CACGTCCCTG           TCACACGTCG           TTCGCGGACA
CAGCGCCGCA           GCCATGTCCG           AACGCCTTTG           GTGCAGGGAC           AGTGTGCAGC           AAGCGCCTGT 11650                11660                11670         UL132 11680                11690                11700
TAGCAAGAAA           TCCACGTCGC           CACATCTCGA           GAATGCCGGC           CTTGCGGGGT           CCCCTTCGCG
ATCGTTCTTT           AGGTGCAGCG           GTGTAGAGCT           CTTACGGCCG           GAACGCCCCA           GGGGAAGCGC 11710                11720                11730                11740                11750                11760
CAACATTCCT           GGCCCTGGTC           GCGTTCGGGT           TGCTGCTTCA           GATAGACCTC           AGCGACGCTA
GTTGTAAGGA           CCGGGACCAG           CGCAAGCCCA           ACGACGAAGT           CTATCTGGAG           TCGCTGCGAT 11770                11780                11790                11800                11810                11820
CGAATGTGAC           CAGCAGCACA           AAAGTCCCTA           CTAGCACCAG           CAACAGAAAT           AACGTCGACA
GCTTACACTG           GTCGTCGTGT           TTTCAGGGAT           GATCGTGGTC           GTTGTCTTTA           TTGCAGCTGT
```

```
11830      11840      11850      11860      11870      11880
ACGCCACGAG TAGCGGACCC ACAACCGGGA TCAACATGAC CACCACCCAC GAGTCTTCCG
TGCGGTGCTC ATCGCCTGGG TGTTGGCCCT AGTTGTACTG GTGGTGGGTG CTCAGAAGGC 11890      11900      11910      11920      11930      11940
TTCACAACGT GCGCAATAAC GAGATCATGA AAGTGCTGGC TATCCTCTTC TACATCGTGA
AAGTGTTGCA CGCGTTATTG CTCTAGTACT TTCACGACCG ATAGGAGAAG ATGTAGCACT 11950      11960      11970      11980      11990      12000
CAGGCACCTC CATTTTCAGC TTCATAGCGG TACTGATCGC GGTAGTTTAC TCCTCGTGTT
GTCCGTGGAG GTAAAAGTCG AAGTATCGCC ATGACTAGCG CCATCAAATG AGGAGCACAA 12010      12020      12030      12040      12050      12060
GCAAGCACCC GGGCCGCTTT CGTTTCGCCG ACGAAGAGGC CGTCAACCTG TTGGACGACA
CGTTCGTGTC CCCGGCGAAA GCAAAGCGGC TGCTTCTCCG GCAGTTGGAC AACCTGCTGT 12070      12080      12090      12100      12110      12120
CGGACGACAG TGGCGGCAGC AGCCCGTTTG GCAGCGGTTC CCGACGAGGT TCTCAGATCC
GCCTGCTGTC ACCGCCGTCG CGGGCAAAC CGTCGCCAAG GGCTGCTCCA AGAGTCTAGG 12130      12140      12150      12160      12170      12180
CCGCCGGATT TTGTTCCTCG AGCCCTTATC AGCGGTTGGA AACTCGGGAC TGGGACGAGG
GGCGGCCTAA AACAAGGAGC TCGGGAATAG TCGCCAACCT TTGAGCCCTG ACCCTGCTCC 12190      12200      12210      12220      12230      12240
AGGAGGAGGC GTCCGCGGCC CGCGAGCGCA TGAAACATGA TCCTGAGAAC GTCATCTATT
TCCTCCTCCG CAGGCGCCGG GCGCTCGCGT ACTTTGTACT AGGACTCTTG CAGTAGATAA 12250      12260      12270      12280      12290      12300
TCAGAAAGGA TGGCAACTTG GACACGTCGT TCGTGAATCC CAATTATGGG AGAGGCTCGC
AGTCTTTCCT ACCGTTGAAC CTGTGCAGCA AGCACTTAGG GTTAATACCC TCTCCGAGCG
```

FIG. 1M-2

```
           12310      12320      12330      12340      12350      12360
      CTTTGACCAT CGAATCTCAC CTCTCGGACA ATGAGGAGGA CCCCATCAGG TACTACGTTT
      GAAACTGGTA GCTTAGAGTG GAGAGCCTGT TACTCCTCCT GGGGTAGTCC ATGATGCAAA 12370      12380      12390      12400      12410      12420
      CGGTGTACGA TGAACTGACC GCCTCGGAAA TGGAAGAACC TTCGAACAGC ACCAGCTGGC
      GCCACATGCT ACTTGACTGG CGGAGCCTTT ACCTTCTTGG AAGCTTGTCG TGGTCGACCG 12430      12440      12450      12460      12470      12480
      AGATTCCCAA ACTAATGAAA GTTGCCATGC AACCCGTCTC GCTCAGAGAT CCCGAGTACG
      TCTAAGGGTT TGATTACTTT CAACGGTACG TTGGGCAGAG CGAGTCTCTA GGGCTCATGC

UL132  12490      12500      12510      12520      12530      12540
      ACTAGGCTTT TTTTTTTGTC TTTCGGTTCC AACTCTTTCC CCGCCCATC ACCTGCCCTG
      TGATCCGAAA AAAAAAACAG AAAGCCAAGG TTGAGAAAGG GGCGGGGTAG TGGAGCGGAC 12550      12560      12570      12580      12590      12600
      TACTATGTGT ATGATGTCTC ATAATAAAGC TTTCTTTCTC AGTCTGCAAC ATGCAGCTGT
      ATGATACACA TACTACAGAG TATTATTTCG AAAGAAAGAG TCAGACGTTG TACGTCGACA 12610      12620      12630      12640      12650      12660
      GTCGGGTGTG GCTGTCTGTT TGTCTGTGCG CCGTGGTGCT GGGTCAGTGC CAGCGGGAAA
      CAGCCCACAC CGACAGACAA ACAGACACGC GGCACCACGA CCCAGTCACG GTCGCCCTTT 12670      12680      12690      12700      12710      12720
      CCGCGGAAAA AAACGATTAT TACCGAGTAC CGCATTACTG GACGCGGTGC TCTCGCGCGC
      GGCGCCTTTT TTTGCTAATA ATGGCTCATG GCGTAATGAC CCTGCCACG AGAGCGCGCG 12730      12740      12750      12760      12770      12780
      TGCCCGACCA AACCCGTTAC AAGTATGTGG AACAGCTCGT GGACCTCACG TTGAACTACC
      ACGGGCTGGT TTGGGCAATG TTCATACACC TTGTCGAGCA CCTGGAGTGC AACTTGATGG
```

FIG._1N-1

```
         12790            12800            12810            12820            12830            12840
ACTACGATGC GAGCCACGGC TTGGACAACT TTGACGTGCT CAAGAGGTGA GGGTACGCGC
TGATGCTACG CTCGGTGCCG AACCTGTTGA AACTGCACGA GTTCTCCACT CCCATGCGCG 12850            12860            12870            12880            12890            12900
TAAAGGTGCA TGACAACGGG AAGGTAAGGG CGAACGGGTA ACGGCTAAGT AACCCGCATGG
ATTTCCACGT ACTGTTGCCC TTCCATTCCC GCTTGCCCAT TGCCGATTCA TTGGCGTACC 12910            12920            12930            12940            12950            12960
GGTATGAAAT GACGTTTGGA ACCTGTGCTT GCAGAATCAA CGTGACCGAG GTGTCGTTGC
CCATACTTTA CTGCAAACCT TGGACACGAA CGTCTTAGTT GCACTGGCTC CACAGCAACG 12970            12980            12990            13000            13010            13020
TCATCAGCGA CTTTAGACGT CAGAACCGTC GCGGCGGCAC CAACAAAAGG ACCACGTTCA
AGTAGTCGCT GAAATCTGCA GTCTTGGCAG CGCCGCCGTG GTTGTTTTCC TGGTGCAAGT 13030            13040            13050            13060            13070            13080
ACGCCGCCGG TTCGCTGGCG CCACACGCCC GGAGCCTCGA GTTCAGCGTG CGGCTCTTTG
TGCGGCGGCC AAGCGACCGC GGTGTGCGGG CCTCGGAGCT CAAGTCGCAC GCCGAGAAAC 13090            13100         13110 UL130 13120            13130            13140
CCAACTAGCC TGCGTCACGG GAAATAATAT GCTGCGGCTT CTGCTTCGTC ACCACTTTCA
GGTTGATCGG ACGCAGTGCC CTTTATTATA CGACGCCGAA GACGAAGCAG TGGTGAAAGT 13150            13160            13170            13180            13190            13200
CTGCCCTGCTT CTGTGCCGCG TTTGGGCAAC GCCCTGTCTG GCGTCTCCGT GGTCGACGCT
GACGGGACGAA GACACGCGCC AAACCCGTTG CGGGACAGAC CGCAGAGCA CCAGCTGCGA
```

```
13210      13220      13230      13240      13250      13260
AACGGCAAAC CAGAATCCGT CCCCGCCATG GTCTAAACTG ACGTATTCCA AACCGCATGA
TTGCCGTTTG GTCTTAGGCA GGGGCGGTAC CAGATTTGAC TGCATAAGGT TTGGCGTACT 13270      13280      13290      13300      13310      13320
CGCGGCGACG TTTTACTGTC CTTTTCTCTA TCCCTCGCCC CCACGGTCCC CCTTGCAATT
GCGCCGCTGC AAAATGACAG GAAAAGAGAT AGGGAGCGGG GGTGCCAGGG GGAACGTTAA 13330      13340      13350      13360      13370      13380
CTCGGGGTTC CAGCAGGTAT CAACGGGTCC CGAGTGTCGC AACGAGACCC TGTATCTGCT
GAGCCCCAAG GTCGTCCATA GTTGCCCAGG GCTCACAGCG TTGCTCTGGG ACATAGACGA 13390      13400      13410      13420      13430      13440
GTACAACCGG GAAGGCCAGA CCTTGGTGGA GAGAAGCTCC ACCTGGGTGA AAAAGGTGAT
CATGTTGGCC CTTCCGGTCT GGAACCACCT CTCTTCGAGG TGGACCCACT TTTTCCACTA 13450      13460      13470      13480      13490      13500
CTGGTATCTG AGCGGTCGCA ACCAGACCAT CCTCCAACGG ATGCCCCAAA CGGCTTCGAA
GACCATAGAC TCGCCAGCGT TGGTCTGGTA GGAGGTTGCC TACGGGGTTT GCCGAAGCTT 13510      13520      13530      13540      13550      13560
ACCGAGCGAC GGAAACGTGC AGATCAGCGT GGAAGACGCC AAGATTTTTG GAGCGCACAT
TGGCTCGCTG CCTTTGCACG TCTAGTCGCA CCTTCTGCGG TTCTAAAAAC CTCGCGTGTA 13570      13580      13590      13600      13610      13620
GGTGCCCAAG CAGACCAAGC TGCTACGCTT CGTCGTCAAC GATGGCACGC GTTATCAGAT
CCACGGGTTC GTCTGGTTCG ACGATGCGAA GCAGCAGTTG CTACCGTGCG CAATAGTCTA 13630      13640      13650      13660      13670      13680
GTGTGTGATG AAGCTGGAGA GCTGGGCCCA CGTCTTCCGG GACTACAGCG TGTCTTTTCA
CACACACTAC TTCGACCTCT CGACCCGGGT GCAGAAGGCC CTGATGTCGC ACAGAAAAGT
```

FIG._10-1

```
         13690                13700      13710                13720      13730                13740
GGTGCGATTG  ACGTTCACCG  AGGCCAATAA  CCAGACTTAC  ACCTTCTGTA  CCCATCCCAA
CCACGCTAAC  TGCAAGTGGC  TCCGGTTATT  GGTCTGAATG  TGGAAGACAT  GGGTAGGGTT
         13750 UL130    13760      13770                13780      13790                13800
TCTCATCATT  TGAGCCCCGTC  GCGCGCGCAG  GGAATTTTGA  AAACCGCGCG  TCATGAGTCC
AGAGTAGTAA  ACTCGGGGCAG  CGCGCGCGTC  CCTTAAAACT  TTTGGCGCGC  AGTACTCAGG
         13810                13820      13830                13840      13850                13860
CAAAGACCTG  ACGCCGTTCT  TGACGACGTT  GTGGCTGCTA  TTTGGGTCACA  GCCGCGTGCC
GTTTCTGGAC  TGCGGCAAGA  ACTGCTGCAA  CACCGACGAT  AACCCAGTGT  CGGCGCACGG
         13870                13880      13890                13900      13910                13920
GCGGGTGCGC  GCAGAAGAAT  GTTGCGAATT  CATAAACGTC  AACCACCCGC  CGGAACGCTG
CGCCCACGCG  CGTCTTCTTA  CAACGCTTAA  GTATTTGCAG  TTGGTGGGCG  GCCTTGCGAC
         13930                13940      13950                13960      13970                13980
TTACGATTTC  AAAATGTGCA  ATCGCTTCAC  CGTCGCGTAC  GTATTTTCAT  GATTGTCTGC
AATGCTAAAG  TTTTACACGT  TAGCGAAGTG  GCAGCGCATG  CATAAAAGTA  CTAACAGACG
         13990                14000      14010                14020      14030                14040
GTTCTGTGGT  GCGTCTGGAT  TTGTCTCTCG  ACGTTTCTGA  TAGCCATGTT  CCATCGACGA
CAAGACACCA  CGCAGACCTA  AACAGAGAGC  TGCAAAGACT  ATCGGTACAA  GGTAGCTGCT
         14050                14060      14070                14080      14090                14100
TCCTCGGGAA  TGCCAGAGTA  GATTTTCATG  AATCCACAGG  CTGCGGTGTC  CGGACGGCGA
AGGAGCCCTT  ACGGTCTCAT  CTAAAAGTAC  TTAGGTGTCC  GACGCCACAG  GCCTGCCGCT
         14110                14120      14130                14140      14150                14160
AGTCTGCTAC  AGTCCCGAGA  AAACGGCTGA  GATTCGCGGG  ATCGTCACCA  CCATGACCCA
TCAGACGATG  TCAGGGCTCT  TTTGCCGACT  CTAAGCGCCC  TAGCAGTGGT  GGTACTGGGT
```

```
     14170      14180      14190      14200      14210      14220
TTCATTGACA CGCCAGGTCG TACACAACAA ACTGACGAGC TGCAACTACA ATCCGTAAGT
AAGTAACTGT GCGGTCCAGC ATGTGTTGTT TGACTGCTCG ACGTTGATGT TAGGCATTCA 14230      14240      14250      14260      14270      14280
CTCTTCCTCG AGGGCCTTAC AGCCTATGGG AGAGTAAGAC AGAGAGGGAC AAAACATCAT
GAGAAGGAGC TCCCGGAATG TCGGATACCC TCTCATTCTG TCTCTCCCTG TTTTGTAGTA 14290      14300      14310      14320      14330      14340
TAAAAAAAAA AGTCTAATTT CACGTTTTGT ACCCCCCTTC CCCTCCGTGT TGTAGCCCAT
ATTTTTTTTT TCAGATTAAA GTGCAAAACA TGGGGGGAAG GGGAGGCACA ACATCGGGTA 14350      14360      14370      14380      14390      14400
CGGCCGCGGC GATCTCCTAG TAACACTCGT CCGACACTTC CACCATCTCC AGCTCGGCCG
GCCGGCGCCG CTAGAGGATC ATTGTGAGCA GGCTGTGAAG GTGGTAGAGG TCGAGCCGGC 14410      14420      14430      14440      14450      14460
GCGGTTCGGC ATCCTCTACC AGCGGGCGTCG TCTCATCTTT GCCGCAGCAG CGGACGCACA
CGCCAAGCCG TAGGAGATGG TCGCCGCAGC AGAGTAGAAA CGGCGTCGTC GCCTGCGTGT 14470      14480      14490      14500      14510      14520
CCTTCTCCAG GCAGAACGCC ACCAGCTGCC GCCGAACGTA CCACAGGTAC ACGTGCAGAC
GGAAGAGGTC CGTCTTGCGG TGGTCGACGG CGGCTTGCAT GGTGTCCATG TGCACGTCTG 14530      14540      14550      14560      14570      14580
CTGCGAACAG GACTACGGAG GTCATGACCA CCACGACGCA CACGGGAATC CAGGGATCGA
GACGCTTGTC CTGATGCCTC CAGTACTGGT GGTGCTGCGT GTGCCCTTAG GTCCCTAGCT 14590      14600      14610      14620      14630      14640
GATTGTTGCT GGAACTCATG GCTATCGCCA CCGACGTGCC CGGTCTGTC TCACCGCCGC
CTAACAACGA CCTTGAGTAC CGATAGCGGT GGCTGCACGG GCAGACAG AGTGGCGGCG
```

FIG._1P-1

```
14650       14660       14670       14680       14690       14700
TCGCCCGATG  TCGCGCGGCT  TGTTATACGC  TAGCCCGTCG  CCGCCTCGGG  GCACGGTGCC
AGCGGGCTAC  AGCGCGCCGA  ACAATATGCG  ATCGGGCAGC  GGCGGAGCCC  CGTGCCACGG 14710       14720       14730       14740       14750       14760
CTCCTACCCA  CGTAACTTCC  TCCGTGACTT  AAAGTCGCGT  GTGGTAGATC  TCCTGCTCCG
GAGGATGGGT  GCATTGAAGG  AGGCACTGAA  TTTCAGCGCA  CACCATCTAG  AGGACGAGGC 14770       14780       14790       14800       14810       14820
TGGACGAACC  GTCCGGCAGG  ATAGCGGTTA  AGGATTCGGT  GCTAAGGCCG  TGTCGCCAAC
ACCTGCTTGG  CAGGCCGTCC  TATCGCCAAT  TCCTAAGCCA  CGATTCCGGC  ACAGCGGTTG 14830       14840       14850       14860       14870       14880
GTCGAATGCT  ACGTTGCAAC  AGCTTCGACG  GACGGCCATC  CCCTCTCTCA  TCGCAATAAT
CAGCTTACGA  TGCAACGTTG  TCGAAGCTGC  CTGCCGGTAG  GGGAGAGAGT  AGCGTTATTA 14890       14900       14910       14920       14930       14940
AAAACACCAG  CAGCGCGCAC  GACGCGATCA  CGGTGACACC  CATGATTAGA  CCCACGCAGA
TTTGTGGTC   GTCGCGCGTG  CTGCGCTAGT  GCCACTGTGG  GTACTAATCT  GGGTGCGTCT 14950       14960       14970       14980       14990       15000
TAGCCAGCCC  CGCTAGCGTA  TCTAGCCGCA  TCCCGTTCGC  TCCCGTTGTC  TCCTGAGCGA
ATCGGTCGGG  GCGATCGCAT  AGATCGCGGT  AGGGCAAGCG  AGGGCAACAG  AGGACTCGCT 15010       15020       15030       15040       15050       15060
AGCAACTTCT  CGGTCCCCGT  TTTCAACAGT  TTTTGTTTCC  TTCTCCGCGA  CTAGATGTTA
TCGTTGAAGA  GCCAGGGGCA  AAAGTTGTCA  AAAACAAAGG  AAGAGGCGCT  GATCTACAAT 15070       15080       15090       15100       15110       15120
ACGCCCGCGG  TCTTTCCGGC  CGTGCTCTAC  CTCCTGGCGC  TTGTCGTCTG  GGTTGAGATG
TGCGGGCGCC  AGAAAGGCCG  GCACGAGATG  GAGGACCGCG  AACAGCAGAC  CCAACTCTAC
```

*FIG._1P-2*

|       |       |       |       |       |       |
|-------|-------|-------|-------|-------|-------|
| 15130 | 15140 | 15150 | 15160 | 15170 | 15180 |
| TTCTGCCTCG | TCGCCGTAGC | CGTCGTCGAG | CGCGAGATCG | CCTGGGCGCT | GCTGCTGCGG |
| AAGACGGAGC | AGCGGCATCG | GCAGCAGCTC | GCGCTCTAGC | GGACCCGCGA | CGACGACGCC |
| 15190 | 15200 | 15210 | 15220 | 15230 | 15240 |
| ATGCTGGTCG | TTGGCCTGAT | GGTGGAAGTC | CCGCCGCCCG | CCGCTTGGAC | CTTCGTGCGT |
| TACGACCAGC | AACCGGACTA | CCACCTTCAG | GGCGGCGGGC | GGCGAACCTG | GAAGCACGCA |
| 15250 | 15260 | 15270 | 15280 | 15290 | 15300 |
| TGTCTTGCCT | ATCAGCGCTC | CTTCCCCGTG | CTTACGGCCT | TCCCCTGAAA | CCCACGTTAA |
| ACAGAACGGA | TAGTCGCGAG | GAAGGGCGAG | GAATGCCGGA | AGGGGACTTT | GGGTGCAATT |
| 15310 | 15320 | 15330 | 15340 | 15350 | 15360 |
| CCGACCGTCC | CAAAAACGCC | GGTGTTAACA | CAGGAAAAAA | AGAAACCACG | CAGGAACCGC |
| GGCTGGCAGG | GTTTTGCGCG | CCACAATTGT | GTCCTTTTTT | TCTTTGGTGC | GTCCTTGGCG |
| 15370 | 15380 | 15390 | 15400 | 15410 | 15420 |
| GCAGGAACCA | CGGGAACAT | GGGACACTAT | CTGGAAATCC | GTCGCTTGGT | ACTTCACGTG |
| CGTCCTTGGT | GCGCCTTGTA | CCCTGTGATA | GACCCTTAGG | CAGCGAACCA | TGAAGTGCAC |
| 15430 | 15440 | 15450 | 15460 | 15470 | 15480 |
| ACTCTGCTGC | TCGGGCGTCAT | GGTCAGTATC | GTCAGTTGGT | TGTTCAACGT | CATCGTCTTC |
| TGAGACGACG | AGCCGCAGTA | CCAGTCATAG | CAGCGAACCA | ACAAGTTGCA | GTAGCAGAAG |
| 15490 | 15500 | 15510 | 15520 | 15530 | 15540 |
| GTCCCGGTTT | AAAAACCATC | GTTATAAAGC | CACCCGGACA | ACTTCACGTG | AACCACCGTC |
| CAGGGCCAAA | TTTTTGGTAG | CAATATTTCG | GTGGGCCTGT | TGAAGTGCAC | TTGGTGGCAG |
| 15550 | 15560 | 15570 | 15580 | 15590 | 15600 |
| CACTTGCCTA | CGGCGCTGCT | TCAGGGAAAC | TCCTCTTCCT | TCTGCTCTTC | CTCCTTCACC |
| GTGAACGGAT | GCCGCGACGA | AGTCCCTTTG | AGGAGAAGGA | AGACGAGAAG | GAGGAAGTGG |

FIG._1Q-1

```
15610       15620       15630       15640       15650       15660
GCAGGGATCG  TTTCCCTCGA  CCAGGGACTC  GCCGAAGCAA  CCGCCGGAGC  AACCTGGAGG
CGTCCCTAGC  AAAGGGAGCT  GGTCCCTGAG  CGGCTTCGTT  GGCGGCCTCG  TTGGACCTCC 15670       15680       15690       15700       15710       15720
AGTCGCGGCA  TGACGGCGCC  CAAGTGTGTC  ACCACCAGTA  CTTATCTGGT  CAAGACCAAG
TCAGCGCCGT  ACTGCCGCGG  GTTCACACAG  TGGTGGTCAT  GAATAGACCA  GTTCTGGTTC 15730       15740       15750         15760 UL149  15770       15780
GAACAGCCCT  GGTGGCCCGA  CAACGCCATC  AGGAGATGGT  GGATCAGTGT  TGCTATCGTC
CTTGTCGGGA  CCACCGGGCT  GTTGCGGTAG  TCCTCTACCA  CCTAGTCACA  ACGATAGCAG 15790       15800       15810       15820       15830       15840
ATCTTCATCG  GAGTCTGTCT  GGTGGCCCTG  ATGTACTTTA  CGCAGCAGCA  GGCACGCAGC
TAGAAGTAGC  CTCAGACAGA  CCACCGGGAC  TACATGAAAT  GCGTCGTCGT  CCGTGCGTCG 15850       15860       15870  UL150  15880       15890       15900
GGGAGCAGCA  GCGGCTAGAC  AAGTCTCTGG  CGGCTACAGC  TCCAAGCGCC  GTAGCCGGGC
CCCTCGTCGT  CGCCGATCTG  TTCAGAGACC  GCCGATGTCG  AGGTTCGCGG  CATCGGCCCG 15910       15920       15930       15940       15950       15960
CGCCTGCCGA  TCGGCGACGTC  GTGGACCATC  GAACAGAGAC  TCACGCGTAC  GAGACCCCGA
GCGGACGGCT  AGCCGCTGCAG  CACCTGGTAG  CTTGTCTCTG  AGTGCGCATG  CTCTGGGGCT 15970       15980       15990       16000       16010       16020
GGTACGCCAC  GCGGTGCCTA  ACGCGGTATA  CCACACCCGT  ACGGTCTGCA  GTGCGGCGTA
CCATGCGGTG  CGCCACGGAT  TGCGCCATAT  GGTGTGGGCA  TGCCAGACGT  CACGCCGCAT 16030       16040       16050       16060       16070       16080
CAACGTGTGG  AAAACGCGTT  GCGTCGCAGA  GTCCGCCACG  TTCCTGTCTT  GTCGCTCCCC
GTTGCACACC  TTTTGCGCAA  CGCAGCGTCT  CAGGCGGTGC  AAGGACAGAA  CAGCGAGGGG
```

FIG._1Q-2

```
                16090      16100      16110      16120 UL149 16130      16140
           AATCGTCTCC CGCACACCCC CCGGACACC  CAGAGGGCGG GTGAGCCAAG TATTCTTAAG
           TTAGCAGAGG GCGTGTGGGG GGCGCTGTGG GTCTCCCGCC CACTCGGTTC ATAAGAATTC 16150      16160      16170      16180      16190      16200
           GCCGTTCTTT GTTCCATAGC CCATAAATTG TTGATTCCGG AGCTCGTTGG CGCGGAAATA
           CGGCAAGAAA CAAGGTATCG GGTATTTAAC AACTAAGGCC TCGAGCAACC GCGCCTTTAT 16210      16220      16230      16240      16250      16260
           GCCGGATAAG GGGAGCAACA ACCGTTGGCG AAAGCCGTCC CGCTCATTCA GTCCGGGTTT
           CGGCCTATTC CCCTCGTTGT TGGCAACCGC TTTCGGCAGG GCGAGTAAGT CAGGCCCAAA 16270      16280      16290      16300      16310      16320
           CGCGTCCAGT CGGACGTGTG ACCGTTGGGC AACGGAACGG CGTTTCACTG CCAAAATCGT
           GCGCAGGTCA GCCTGCACAC TGGCAACCCG TTGCCTTGCC GCAAAGTGAC GGTTTTAGCA 16330      16340      16350      16360      16370      16380
           ATCGGGTAGT GTACGAGACG TCGGCGGTGC AGAATGCGAC TCGGGGCGTA GCTCGCCGTC
           TAGCCCATCA CATGCTCTGC AGCCGCCACG TCTTACGCTG AGCCGCCAT  CGAGCGGCAG 16390      16400      16410      16420      16430      16440
           GCTATGCGGC TCGTCGCCGT GTGGCGCGGC CTGGCCGGCT GTCTGCGTCC AGATCTGTTG
           CGATACGCCG AGCAGCGGCA CACCGCGCCG GACCGGCCGA CAGACGCAGG TCTAGACAAC 16450      16460      16470      16480      16490      16500
           GCCTTTTGGT TCCTCTGGCT GCTGCTGCGT GTGTGCTTTG GTAGACGCGG TGGCAGTTTG
           CGGAAAACCA AGGAGACCGA CGACGACGCA CACACGAAAC CATCTGCGCC ACCGTCAAAC 16510      16520      16530      16540      16550      16560
           CGGTCTGCGG TAAGTGAGGA TGTCGCCGAG CAAACGCACT TGCGGCGCGT GGGCGGCACG
           GCCAGACGCC ATTCACTCCT ACAGCGGCTC GTTTGCGTGA ACGCCGCGCA CCCGCCGTGC
```

*FIG._1R-1*

```
                                                       16570                16580                16590                16600                16610                16620
                                                  CGTGTCATTG           TAGGTTCGTT           GCCAGATGGC           AAGTGCTGTC           AACAGCAGGC           GTTGTGGGCG
                                                  GCACAGTAAC           ATCCAAGCAA           CGGTCTACCG           TTCACGACAG           TTGTCGTCCG           CAACACCCGC 16630                16640                16650                16660                16670                16680
                                                  GTCGGTGTAT           TTTTGTGGGT           TGCGGTGAGA           GTCGGCACTC           GGTGTTTTGT           GAGTCATCTC
                                                  CAGCCACATA           AAAACACCCA           ACGCCACTCT           CAGCCGTGAG           CCACAAAACA           CTCAGTAGAG 16690                16700                16710                16720                16730                16740
                                                  AACTATCTGT           GTTGCTTTGA           GCAGCGTCCA           GAACAGCGAC           GCGACTTTGG           GGATGGCCTC
                                                  TTGATAGACA           CAACGAAACT           CGTCGCAGGT           CTTGTCGCTG           CGCTGAAACC           CCTACCGGAG 16750                16760                16770                16780                16790                16800
                                                  GTGCTCACCT           CCGCGGAGAG           CGCCGCCGGA           CCTGCTCGTC           AGCAGCGAGC           TACGCAGACG
                                                  CACGAGTGGA           GGCGCCCTCT           GCGGCGGCCT           GGACGAGCAG           TCGTCGCTCG           ATGCGTCTGC 16810                16820                16830                16840                16850                16860
                                                  GAATATCTGG           AGGAGAGTTA           CGTGTGTCAC           AGGAGAGCGC           GGGTCTCCGG           CGGTAACGAC
                                                  CTTATAGACC           TCCTCTCAAT           GCACACAGTG           TCCTCTCGCG           CCCAGAGGCC           GCCATTGCTG 16870                16880                16890                16900                16910                16920
                                                  GGCGGTGTCG           TCGACACGTG           TGCGGCCTGT           TGTGCTCTGC           GGAAAAGTGC           CGGTCTCGGA
                                                  CCGCCACAGC           AGCTGTGCAC           ACGCCGGACA           ACACGAGACG           CCTTTTCACG           GCCAGAGCCT 16930                16940                16950                16960                16970                16980
                                                  GACCGTGGAC           GAAAAGAGA            ACGCAGCAGC           TACCGCTGGC           GGCGGCGGCG           TTAATGCAGC
                                                  CTGGCACCTG           CTTTTTCTCT           TGCGTCGTCG           ATGGCGACCG           CCGCCGCCGC           AATTACGTCG
```

FIG._1R-2

```
        16990      17000      17010      17020      17030      17040
CGTTGATGTT CGACGTTGTG AGCACTCGGA AACAGCGGTG AGGCAGAAGG TCGATTCTCC
GCAACTACAA GCTGCAACAC TCGTGAGCCT TTGTCGCCAC TCCGTCTTCC AGCTAAGAGG 17050      17060      17070      17080      17090      17100
AGGGAACGAC AGTCGATGCG TGGTAGCCGC AGCAGGTGAG GTTGGGGCGG ACAACGTGTT
TCCCTTGCTG TCAGCTACGC ACCATCGGCG TCGTCCACTC CAACCCCGCC TGTTGCACAA 17110      17120      17130      17140      17150      17160
GCGGATTGTG GCGAGAACGT CGTCCTCCCC TTCTTCACCG CCCCACCCAC CCTCGGTTGG
CGCCTAACAC CGCTCTTGCA GCAGGAGGGG AAGAAGTGGC GGGTGGGGTG GGAGCCAACC 17170      17180      17190      17200      17210      17220
TGTTTCTTTT TTCTTGTGTC CTGCAGATAG TTCCACGGAC AGCGACGGCA AGTCCATAAT
ACAAAGAAAA AAGAACACAG GACGTCTATC AAGGTGCCTG TCGCTGCCGT TCAGGTATTA 17230      17240      17250      17260      17270      17280
CAGCGGTGTG CAAGTGGTGG AACACGACGA AGATATCATC GCGCCGCAGA GTTGTGGTG
GTCGCCACAC GTTCACCACC TTGTGCTGCT TCTATAGTAG CGCGGCGTCT CAAACACCAC

17290 UL151    17300      17310      17320      17330      17340
CACGGGCGTC AAGGAAGCCC TCTGGGATGT GGCTCTGTTG GAAGTGCCGC GTTGGGCGTG
GTGCCGCAAG TTCCTTCGGG AGACCCTACA CCGAGACAAC CTTCACGGCG CAACCCGCAC 17350      17360      17370      17380      17390      17400
GCAGGGCTGG AAGAGGTGGC GCAACAGCGA GGCCGGGCGT CGATGGAGTG CTGGGTCTGC
CGTCCCGACC TTCTCCACCG CGTTGTCGCT CCGGCCCGCA GCTACCTCAC GACCCAGACG 17410      17420      17430      17440      17450      17460
GTCGGCTTCC AGCTTGTCTG ACTTGGCGGG CGAGGCCGTT GGAGAATTGG TGGGATCGGT
CAGCCGAAGG TCGAACAGAC TGAACCGCCC GCTCCGGCAA CCTCTTAACC ACCCTAGCCA
```

*FIG._1S-1*

```
17470      17480      17490      17500      17510      17520
CGTCGCGTAC GTGATCCTTG AACGTCTGTG GTTGGCAGCC AGAGGTTGGG TGTGCGAAAC
GCAGCGCATG CACTAGGAAC TTGCAGACAC CAACCGTCGG TCTCCAACCC ACACGCTTTG 17530      17540      17550      17560      17570      17580
AGGTGTGGAA GCCGAGGAGG CCATGTCGCG GCGGCGACAG CGCATGCTGT GGCGTATTGT
TCCACACCTT CGGCTCCTCC GGTACAGCGC CGCCGCTGTC GCGTACGACA CCGCATAACA 17590      17600      17610      17620      17630      17640
TCTCTCGTGG AGGCGACGGC GAATGCAGCA GACGGTGTTC GATGGAGATG GCCTGCGGGG
AGAGAGCACC TCCGCTGCCG CTTACGTCGT CTGCCACAAG CTACCTCTAC CGGACGCCCC 17650      17660      17670      17680      17690      17700
AAGAAAGCGC CGTGTTGTGA GCAGACGACG TAGGATGCGG GACGTCGGAG CACATGGGCC
TTCTTTCGCG GCACAACACT CGTCTGCTGC ATCCTACGCC CTGCAGCCTC GTGTACCCGG 17710      17720      17730      17740      17750      17760
ATGTGTGGTG GCAGATGGCG GTGTCCGCTG GTGTCTGCTG CGGCAGTGCA TAGACGAAGC
TACACACCAC CGTCTACCGC CACAGGCGAC CACAGACGAC GCCGTCACGT ATCTGCTTCG

UL150 17810
17770      17780      17790      17800      17810      17820
AACATGTCGC TGTGAAGAGA TAGAGTGTGA GCATAGCTGC ATGCAGCGTT GCGTGTATAA
TTGTACAGCG ACACTTCTCT ATCTCACACT CGTATCGACG TACGTCGCAA CGCACATATT
                                                ↓

17830      17840      17850      17860      17870      17880
GCGGGGGGA  TTAAGACGTT AATAAAGAAT AGCGGGCGGT CTGATAGGGC GACCGCTGAA
CGCCCCCCT  AATTCTGCAA TTATTTCTTA TCGCCGCCAA GACTATCCCG CTGGCGACTT 17890      17900      17910      17920      17930      17940
GTGAGCTGCG TGTGCGTGTG GTTTGTGGAG TCCCCGCCGC CCCCGGTCCC GTGTCCGCCG
CACTCGACGC ACACGCACAC CAAACACCTC AGGGGCGGCG GGGGCCAGGG CACAGGCGGC
```

FIG._1S-2

```
17950          17960      17970      17980      17990      18000
GCAAAGCCCC  CCGGNTCCGC  ACACTCCTGG  CCGCGCAACC  CTCGTCGCTG  CAAAAGCCCC
CGTTTCGGGG  GGCCNAGGCG  TGTGAGGACC  GGCGCGTTGG  GAGCAGCGAC  GTTTTCGGGG 18010          18020      18030      18040      18050      18060
CCGTCCCCGC  ACACCCCCGC  GACCGCCGGT  CCCGCGAGTC  CCCGTCCCCG  CCGCAAAAGG
GGCAGGGGCG  TGTGGGGCG   CTGGCGGCCA  GGGCGCTCAG  GGGCAGGGGC  GGCGTTTTCC 18070          18080      18090      18100      18110      18120
CCCCGTCCT   CGCCGCAAAC  ACCCCCGTCA  CCCCCGTCCC  TCAGNCCGGG  TCCGCGAGTC
GGGGCAGGA   GCGGCGTTTG  TGGGGGCAGT  GGGGCAGGG   AGTCNGGCCC  AGGCGCTCAG 18130          18140      18150      18160      18170      18180
CCCGTTCCCA  GCGTAATCCC  CGTACCCGCA  ACGNCCCGGN  CCCACCGTCG  TCCCGCACAC
GGGCAAGGGT  CGCATTAGGG  GCATGGGCGT  TGCNGGGCCN  GGGTGGCAGC  AGGGCGTGTG 18190          18200      18210      18220      18230      18240
CCCCGTCCC   CCAGCCCCGT  GCCCAGCGTG  CGAAAAAAGC  TCCGTCCCTC  ACACCCGCAG
GGGGCAGGG   GGTCGGGGCA  CGGGTCGCAC  GCTTTTTTCG  AGGCAGGGAG  TGTGGGCGTC 18250          18260      18270      18280      18290      18300
AAAGATCCCT  CAGCGCGGTG  AAACCCCGTC  CCCAGCGCCG  TGCCGCTGAC  AAAGACCATG
TTTCTAGGGA  GTCGCGCCAC  TTTGGGGCAG  GGGTCGCGGC  ACGGCGACTG  TTTCTGGTAC
                                                           ▼
                                                           UL151

18310          18320      18330      18340      18350      18360
GGACGACACG  CACAGGCA..  ..........  ..........  ..........  ..........
CCTGCTGTGC  GTGTCCGT..
```

FIG._1T

```
  10         20         30         40         50         60
ATCGGCGCC  AGAGCTAGAT  CAGGCGTATC  AAATTCCACT  GCCAGGCGAC  CTGATTCTAA
TAGCCCGCGG  TCTCGATCTA  GTCCGCATAG  TTTAAGGTGA  CGGTCCGCTG  GACTAAGATT 70         80         90        100        110        120
CGGTTCCACG  ATCCGGGAGA  GCGTTTCTAG  ATATAGAGCA  AAGCGTACCA  CGTCTACCTG
GCCAAGGTGC  TAGGCCCTCT  CGCAAAGATC  TATATCTCGT  TTCGCATGGT  GCAGATGGAC 130        140        150        160        170        180
CGGTGTAAAA  AACTGTTGTG  GGCGTTCACC  GTCGTTGACC  ACGTAAGCCA  CGTAGAGGCC
GCCACATTTT  TTGACAACAC  CCGCAAGTGG  CAGCAACTGG  TGCATTCGGT  GCATCTCCGG 190        200        210        220        230        240
AACATTTTCC  ACCACGGGTT  CTAGCTGCAG  GCGGCACGTA  AAGCTTAGAA  ACGACGGCTG
TTGTAAAAGG  TGGTGCCCAA  GATCGACGTC  CGCCGTGCAT  TTCGAATCTT  TGCTGCCGAC 250        260        270        280        290        300
TACGGTTTGG  TTCCCGTGAA  GCTGAAGCGT  CACTTCCTTG  CCGGGGCTCA  CCGTGCTGTA
ATGCCAAACC  AAGGGCACTT  CGACTTCGCA  GTGAAGGAAC  GGCCCCGAGT  GGCACGACAT 310        320        330        340        350        360
ACGCCGCACC  GAGTCGGTCA  TCTGCTCCAG  ATCGGTAGAC  CAGAAGGGCG  TGCAATGCAT
TGCGGCGTGG  CTCAGCCAGT  AGACGAGGTC  TAGCCATCTG  GTCTTCCCGC  ACGTTACGTA 370        380        390        400        410        420
ACGTGTCCCAG  TCGCGACACG  CAGCCCAGCC  TAGCTCGGTG  AAGGGTCGAC  GCACACCCGA
TGACAGGGTC  AGCGCTGTGC  GTCGGGTCGG  ATCGAGCCAC  TTCCCAGCTG  CGTGTGGGCT 430        440        450        460        470        480
AAAAGTGTGC  TTGAAGACCA  GGGGGTCGCC  TCGGTAGCTC  AGTAGCCCGAA  CATGCACATA
TTTTCACACG  AACTTCTGGT  CCCCCAGCGG  AGCCATCGAG  TCATCGGCTT  GTACGTGTAT
```

FIG._2A-1

```
         490        500        510        520        530        540
  GTCGCGGCTA CGTTGACAGA CGGCCCGTAG ACAGGCAGGA CAAGCGTGAA CAGCAAGCGC
  CAGCGCCGAT GCAACTGTCT GCCGGGCATC TGTCCGTCCT GTTCGCACTT GTCGTTCGCG 550        560        570        580        590        600
  AACATGCTGC GGGTTAGAAA ATGCGGGCGTG CCGGCCACCG CCCGACTCAT AAACGCTACC
  TTGTACGACG CCCAATCTTT TACGCCCGCAC GGCCGGTGGC GGGCTGAGTA TTTGCGATGG 610        620        630        640        650        660
  AGCATGACGT CTCAGAGATC ACAAGTGACG AGGAGCGTAC CGCAAATCAC TAGGGAAAAG
  TCGTACTGCA GAGTCTAGTG TGTTCACTGC TCCTCGCATG GCGTTTAGTG ATCCCTTTTC 670        680        690        700        710        720
  GCCAGCAGAG CCCGATAGTC TTGCTCTTCG CGAACGATCT CGTCCGGTTC CTCGCAGTCT
  CGGTCGTCTC GGGCTATCAG AACGAGAAGC GCTTGCTAGA GCAGGCCAAG GAGCGTCAGA 730        740        750        760        770        780
  TCGTGGTCCA CAGAAGATGA GGAGCCAGGAT TCTTCGTTAA TTTCTGCCAG GATACTAGTG
  AGCACCAGGT GTCTTCTACT CCTCGTCCTA AGAAGCAATT AAAGACGGTC CTATGATCAC

UL147  790        800        810        820        830        840
  CTGTACCACA CCAGAGCGCT CAGCGTGCCC AGGGCTACCG CACGGTAAAA TAGGGACATG
  GACATGGTGT GGTCTCGCGA GTCGCACGGG TCCCGATGGC GTGCCATTTT ATCCCTGTAC 850        860        870        880        890        900
  ATCACCAGCG CAATCTGAAG TGGTGGTAGT TCAGTTTCTT GGCGTATTTC CAGAGAAAGG
  TAGTGGTCGC GTTAGACTTC ACCACCATCA AGTCAAAGAA CCGCATAAAG GTCTCTTTCC 910        920        930        940        950        960
  CTTTGTAGGC CGTAGGGACT GGCCAGGCAC CGAACTCAAT ATTGGTAGAC ACTACGTCGT
  GAAACATCCG GCATCCCTGA CCGGTCCGTG GCTTGAGTTA TAACCATCTG TGATGCAGCA
```

FIG._2A-2

```
        970       980       990      1000      1010      1020
AAATGCGTTG TTCCTCGTCT AAGATTAACC GAAAAAATAG CCGGTTGATG TGACGACGCA
TTTACGCAAC AAGGAGCAGA TTCTAATTGG CTTTTTTATC GGCCAACTAC ACTGCTGCGT 1030      1040      1050      1060      1070      1080
CGGCTTGCGC GTTAGGATTG AGACACTTGG TGCCCTTGTC CTTTAAAATA GCCAGCACTT
GCCGAACGCG CAATCCTAAC TCTGTGAACC ACGGGAACAG GAAATTTTAT CGGTCGTGAA 1090      1100      1110      1120      1130      1140
CCTGACGATT GCAGCTTTCG CTCGCCGCGA TTGGCTTAAG CAATTCAGTT CCGATTGGCA
GGACTGCTAA CGTCGAAAGC GAGCGGCGCT AACCGAATTC GTTAAGTCAA GGCTAACCGT 1150      1160      1170      1180      1190      1200
GAGTATTCAA CAGAATTTGG TTGTTACAAC GACAGCGTTT GTCGTAATCT TCCAATTCTA
CTCATAAGTT GTCTTAAACC AACAATGTTG CTGTCGCAAA CAGCATTAGA AGGTTAAGAT 1210      1220      1230      1240      1250      1260
AAAGATGGAC GGCTAGGGGA CATACGACAA ATAACATGTA TGCAGTCAAT TGCATATATC
TTTCTACCTG CCGATCCCCT GTATGCTGTT TATTGTACAT ACGTCAGTTA ACGTATATAG 1270      1280      1290      1300      1310      1320
GTACCGATAA AATGTTAGTG TACCGATTCA GAATCGGATG ATGCAACCGT CTTAGCATCA
CATGGCTATT TTACAATCAC ATGGCTAAGT CTTAGCCTAC TACGTTGGCA GAATCGTAGT 1330      1340      1350      1360      1370      1380
TATCGAAAAA GTATACATAT TACCGATTCA TTATAATTAG GGAATTATTT CCAACGCGGA
ATAGCTTTTT CATATGTATA ATGGCTAAGT AATATTAATC CCTTAATAAA GGTTGCGCCT
UL147                                                   UL152

1390      1400      1410      1420      1430      1440
CGTTTGTTAG TGACAGCGTT TTCTTCTACA TGCGGTCCAT TACTATCCTT TACTTTTACC
GCAAACAATC ACTGTCGCAA AAGAAGATGT ACGCCAGGTA ATGATAGGAA ATGAAAATGG
```

FIG._2B-1

```
      1450       1460       1470       1480       1490       1500
AATACTCTGT GCCATGAGTT GTCTTTTTTA CCATCCAGCC ATTTGGACAA ATGATGATCG
TTATGAGACA CGGTACTCAA CAGAAAAAAT GGTAGGTCGG TAAACCTGTT TACTACTAGC 1510       1520       1530       1540       1550       1560
GGAGCTAAAC ATACAGGTTT ACCTCGAGGA GGCAATAGAT AATGTTGAGG TTTGTCACAC
CCTCGATTTG TATGTCCAAA TGGAGCTCCT CCGTTATCTA TTACAACTCC AAACAGTGTG 1570       1580       1590       1600       1610       1620
TCAGGAGGAT TGGGAGGGTC ACGACCAACC CAAAATAAGC CACCTATAGG ATGATGTAAA
AGTCCTCCTA ACCCTCCCAG TGCTGGTTGG GTTTTATTCG GTGGATATCC TACTACATTT 1630       1640       1650       1660       1670       1680
GCTTTGTGTGGG TACACGGACA ACGCAATTCT CTACTGTGAA CCCCATGGTA ATACATAAAT
CGAAACACCC ATGTGCCTGT TGCGTTAAGA GATGACACTT GGGGTACCAT TATGTATTTA 1690       1700       1710       1720   UL152  1730       1740
GCCATCAAAA GACTAATCAG CGAACCAAAA ATTAATCGCA TTCTAATTTT ATTAACTACG
CGGTAGTTTT CTGATTAGTC GCTTGGTTTT TAATTAGCGT AAGATTAAAA TAATTGATGC 1750       1760       1770       1780       1790       1800
TCACTATCAG TAATTCGTAA TATCCGGTAT TCCCGGAAAA TCACTCAAAA CTGCCGTCCAT
AGTGATAGTC ATTAAGCATT ATAGGCCATA AGGGCCTTTT AGTGAGTTTT GACGCAGGTA 1810       1820       1830       1840       1850       1860
GACACATCAA TTCCCGATAA GTACCCCCCT TTGAAATCGG ATCCCCCCAC ATACCAATCA
CTGTGTAGTT AAGGGCTATT CATGGGGGGA AACTTTAGCC TAGGGGGGTG TATGGTTAGT
```

FIG._2B-2

```
1870       1880       1890       1900       1910       1920
ATCACACAAC ACACAGGTTT AAAAATCGAT CACACGTCAA TTAGGTTTCA AAATCGATAC
TAGTGTGTTG TGTGTCCAAA TTTTTAGCTA GTGTGCAGTT AATCCAAAGT TTTAGCTATG 1930       1940       1950       1960       1970       1980
TGTTTATTAT CAGGAATCTA GACTAATTCT ACAATGACAG CTCTGAATTT CTCTCTCGTC
ACAAATAATA GTCCTTAGAT CTGATTAAGA TGTTACTGTC GAGACTTAAA GAGAGAGCAG 1990       2000       2010       2020       2030       2040
TTTCTTGTCA GGTTCTCATC ATCAATCTTC ACTTCCACCC ATCGAGGAGT CATCGTCGCT
AAAGAACAGT CCAAGAGTAG TAGTTAGAAG TGAAGGTGGG TAGCTCCTCA GTAGCAGCGA 2050       2060       2070       2080       2090       2100
CCAAAACCCT TTGGGGTCGC TGGTTGGAAA AGTCTCTGAC ACGATCCAGG CACCCCGTAC
GGTTTTGGGA AACCCCAGCG ACCAACCTTT TCAGAGACTG TGCTAGGTCC GTGGGGCATG 2110       2120       2130       2140       2150       2160
CCAGTCCGAC TGATCTAGCT TACGGAGCAT CTCAACAGGC ATGAGCTGCA GGGCCACGGC
GGTCAGGCTG ACTAGATCGA ATGCCTCGTA GAGTTGTCCG TACTCGACGT CCCGGTGCCG 2170       2180       2190       2200       2210       2220
TGTCACGGCA GGGATTATTA CTACCGTTCA GGTAAAACTGT ATCTCCCTGA GTTACCGTGA
ACAGTGCCGT CCCTAATAAT GATGGCAAGT CCATTTGACA TAGAGGGACT CAATGGCACT 2230       2240       2250       2260       2270       2280
TGGGTCTTTC CTTTGCGTAA AAAATCGCCG GTAAAATGTT TTTTCTTGTT
ACCCAGAAAG GAAACGCATT TTTTAGCGGC CATTTTACAA AAAAGAACAA 2290       2300       2310       2320       2330       2340
CATGTAAAAG TACCGGAACT AAAATGCTAG TTAGAATGGT TGCAGTTGCT ATTAGCGCGG
GTACATTTTC ATGGCCTTGA TTTTACGATC AATCTTACCA ACGTCAACGA TAATCGCGCC
```

FIG._2C-1

```
2350       2360       2370       2380       2390       2400
CTAGTAACAG TAGTTTAGTG TTACATTGTA TACCCATGTT TTTAATAACT ATGAATATTC
GATCATTGTC ATCAAATCAC AATGTAACAT ATGGGTACAA AAATTATTGA TACTTATAAG 2410       2420       2430       2440       2450       2460
TGCTTCACAC CATAAGTGCT TAACCCACAA AAACCACACG GAGACATTAT TGGCTAAARAA
ACGAAGTGTG GTATTCACGA ATTGGGTGTT TTTGGTGTGC CTCTGTAATA ACCGATTTTT 2470       2480       2490       2500       2510       2520
                                             UL153
TAAAAACAAA AGTTTATTGA TGTGCATGTT AGGTTTTAGT CTAAAATTCA TCTGGGTCGT
ATTTTTGTTT TCAAATAACT ACACGTACAA TCCAAAATCA GATTTTAAGT AGACCCAGCA
                                                 →

2530       2540       2550       2560       2570       2580
ATTTGGGAAG TTTTGTATAA CGCGGTCTTC TGGGGACGCG ACGGGCTACCC ATGTATAAGG
TAAACCCTTC AAAACATATT GCGCCAGAAG ACCCCTGCGC TGCCGATGGG TACATATTCC 2590       2600       2610       2620       2630       2640
CTATAAGTGC CACAGATACC ACTATACCCG CCCATACAGC ATGAATTCCC AGGGGAATGT
GATATTCACG GTGTCTATGG TGATATGGGC GGGTATGTCG TACTTAAGGG TCCCCTTACA 2650       2660       2670       2680       2690       2700
TAGTGTTTTT TACAGTTTTT ATTACATTGT CCCACGTTCT GCTATTATGC AGGGGAATTC
ATCACAAAAA ATGTCAAAAA TAATGTAACA GGGTGCAAGA CGATAATACG TCCCCTTAAG 2710       2720       2730       2740       2750       2760
CCTCTTTTGT TTTACATTTA TCAGGTATAG GAGACGATGT TGCAGTTCCT GATAACACGG
GGAGAAAACA AAATGTAAAT AGTCCATATC CTCTGCTACA ACGTCAAGGA CTATTGTGCC 2770       2780       2790       2800       2810       2820
TAGTGTTTTT GTTTTCCTTT TTACCGTCAC TGTAACGTTG CAAAACGTAT TTTCCAGCGT
ATCACAAAAA CAAAAGGAAA AATGGCAGTG ACATTGCAAC GTTTTGCATA AAAGGTCGCA
```

```
       2830       2840       2850       2860       2870       2880
GTTCGGTAGT TACGTTGTAT ATAGTGAGAG AGGTCTTATT GCAGTCTAAA CACATGCCGT
CAAGCCATCA ATGCAACATA TATCACTCTC TCCAGAATAA CGTCAGATTT GTGTACGGCA 2890       2900       2910       2920       2930       2940
TCAGTGGGGA AGTTGAATAA TAATGTCCAA TGCTGCACAG TTGGTGTGCG CGAGGTCCAT
AGTCACCCCT TCAACTTATT ATTACAGGTT ACGACGTGTC AACCACACGC GCTCCAGGTA 2950       2960       2970       2980       2990       3000
ATTTTATCCA TTCTATATCG TGCCATACAT CCGTTCTACT GCAGTTTTTC AAAGTGACGT
TAAAATAGGT AAGATATAGC ACGGTATGTA GGCAAGATGA CGTCAAAAAG TTTCACTGCA 3010       3020       3030       3040       3050       3060
ATCCACCGAC ATATCCCTGTT ACATTAATTA CTTCGTAATT TAAATTAGAG TGTTTATAAA
TAGGTGGCTG TATAGGACAA TGTAATTAAT GAAGCATTAA ATTTAATCTC ACAAATATTT 3070       3080       3090       3100       3110       3120
CGGTGTACAA ACTGCCATTG GTTGGCGTAG TGCTGGTATT CAACCAGGGA GTAGTACTAT
GCCACATGTT TGACGGTAAC CAACCGCATC ACGACCATAA GTTGGTCCCT CATCATGATA 3130       3140       3150       3160       3170       3180
GAATGGTAGA AAACGTTAAT GTTGGCGTAG CGCTTGACGA TGATTTTGAA AGCGTTGAAG
CTTACCATCT TTTGCAATTA CAACCGCATC GCGAACTGCT ACTAAAACTT TCGCAACTTC 3190       3200       3210       3220       3230       3240
TGGTTGCTGA TGCGACTGAA GAAGCGGGTAG AGGGTTTGTG CGTGGTTCCA TTTGCGATAG
ACCAACGACT ACGCTGACTC CTTCGCCATC TCCCAAACAC GCACCAAGGT AAACGCTATC 3250       3260       3270       3280       3290       3300
CTGAAGTGCT GTTAGCATCG GTGACAGAGT TAGAAGAATT TGTGATAGTG GAGGCGGTGG
GACTTCACGA CAATCGTAGC CACTGTCTCA ATCTTCTTAA ACACTATCAC CTCCGCCACC
```

*FIG. 2D-1*

```
       3310            3320            3330           UL153 3340            3350            3360
AGGTAAAGGC      AATTGCACGG      ACAGGAGCAC      GTGTCATTGC      AACCTTCAGA      TATCGTAATC
TCCATTTCCG      TTAACGTGCC      TGTCCTCGTG      CACAGTAACG      TTGGAAGTCT      ATAGCATTAG 3370            3380            3390            3400            3410            3420
ATCAGTAACG      TCCACTTAAC      CGTAAATCTC      CAGTCCATAA      CGTTATTAAA      TTTCGGTTAA
TAGTCATTGC      AGGTGAATTG      GCATTTAGAG      GTCAGGTATT      GCAATAATTT      AAAGCCAATT 3430            3440            3450            3460            3470            3480
CGGGCATTGA      TGTTTCTTCG      GACGTTGTTG      ATCTTTCTTG      CCCGTTTATT      TTCTGATATG
GCCCGTAACT      ACAAAGAAGC      CTGCAACAAC      TAGAAAGAAC      GGGCAAATAA      AAGACTATAC 3490            3500            3510           UL154 3520            3530            3540
GTCTCATAAG      ACATTTATCC      GGAAACGTTG      CTTAGTCCTC      GTGCTCAGGA      TTGTATCGAA
CAGAGTATTC      TGTAAATAGG      CCTTTGCAAC      GAATCAGGAG      CACGAGTCCT      AACATAGCTT 3550            3560            3570            3580            3590            3600
CTATGAATTC      TGATTCACTT      ATATCGTCAC      TTAATGGATG      ATATTTTTTA      TTTAGAGCTC
GATACTTAAG      ACTAAGTGAA      TATAGCAGTG      AATTACCTAC      TATAAAAAAT      AAATCTCGAG 3610            3620            3630            3640            3650            3660
GTCGGACGAA      AAATAGGAGA      ATGCAGGCTA      CACAAATTAA      TGCTAACGTC      CACGTAGTGC
CAGCCTGCTT      TTTATCCTCT      TACGTCCGAT      GTGTTTAATT      ACGATTGCAG      GTGCATCACG 3670            3680            3690            3700            3710            3720
GTCTGCCGTG      TGATGTGTTA      GAATGATTGT      TATAGCGGTA      TAAATGATCT      ATAGATGATG
CAGACGGCAC      ACTACACAAT      CTTACTAACA      ATATCGCCAT      ATTTACTAGA      TATCTACTAC 3730            3740            3750            3760            3770            3780
TGGCTGTATT      GTCTTCATAA      TTGGTCGGTT      TATGAGAAGT      GTCCCATTCG      TGCTTTGGTT
ACCGACATAA      CAGAAGTATT      AACCAGCCAA      ATACTCTTCA      CAGGGTAAGC      ACGAAACCAA
```

*FIG._2D-2*

```
                3790       3800       3810       3820       3830       3840
           CTTCACATAC CCAGGGATTC ACGTGTGTCC CGTTTGTGTT GTTTCTAGGA TGTATTTGCA
           GAAGTGTATG GGTCCCTAAG TGCACACAGG GCAAACACAA CAAAGATCCT ACATAAACGT 3850       3860       3870       3880       3890       3900
           GATTARAGTT TTGATTTTGT TCGGAGGGAT GCCCAGTTTT ATAACATCGA AAGCTATATT
           CTAATTTCAA AACTAAAACA AGCCTCCCTA CGGGTCAAAA TATTGTAGCT TTCGATATAA 3910       3920       3930       3940       3950       3960
           TACCAGAATG AGTAAAATTA AGACCGTACA GAGATAAAGA TAAATTACGA TCGCATGTAA
           ATGGTCTTAC TCATTTTAAT TCTGGCATGT CTCTATTTCT ATTTAATGCT AGCGTACATT 3970       3980       3990       4000       4010       4020
           AACATAAATC ATAGTGATGT TTTAGATAAT TTGTGTGCCA CTCACATAGT ATACGCGAAT
           TTGTATTTAG TATCACTACA AAATCTATTA AACACACGGT GAGTGTATCA TATGCGCTTA 4030       4040       4050       4060       4070       4080
           GGAGGATTTT CAATGAATGG TTATGATATT TTCCATTTCT TATGTTGGGA TGGGTGTATT
           CCTCCTAAAA GTTACTTACC AATACTATAA AAGGTAAAGA ATACAACCCT ACCCACATAA 4090       4100       4110       4120       4130       4140
           TTCCGTGTGT GGATATATTA AAATGTCTAA GCCAGGCTGT GATGTGATGG GTTTCAGATT
           AAGGCACACA CCTATATAAT TTTACAGATT CGGTCCGACA CTACACTGTG CAAAGTCTAA 4150       4160       4170       4180       4190       4200
           TTAGGTTGTG TGTTATAGTA ATATTGTCTC CTTGTGCCGC CTCCAATAAT GTTTCAGATT
           AATCCAACAC ACAATATCAT TATAACAGAG GAACACGGCG GAGGTTATTA CAAAGTCTAA 4210       4220       4230       4240       4250       4260
           CTTTGATAT CGTATTATTT GTACTGTTAG GCGATGAGCA AGTTGGAAGC GGTGTAGTGA
           GAAACTATA GCATAATAAA CATGACAATC CGCTACTCGT TCAACCTTCG CCACATCACT
```

*FIG._2E-1*

```
                4270       4280       4290       4300       4310       4320
           CGTTTTCATT TGCATTTATC ATAGTAGTAG TGTTGGTTGA TAATGATATA GTTTGCAAAG
           GCAAAAGTAA ACGTAAATAG TATCATCATC ACAACCAACT ATTACTATAT CAAACGTTTC 4330       4340       4350       4360       4370       4380
           TCACAGTACT ATCGGTTACA TGCTGTGTCG ATGAATTCGT GTCGCCGTTT GGTGAAGTTG
           AGTGTCATGA TAGCCAATGT ACGACACAGC TACTTAAGCA CAGCGGCAAA CCACTTCAAC 4390       4400       4410       4420       4430       4440
           TTATTACAGT TACGTTAGTT GTAGATGTTT GGGTAGATAT GGTGGAAATA GTTGAGGTCA
           AATAATGTCA ATGCAATCAA CATCTACAAG CCCATCTATA CCACCTTTAT CAACTCCAGT 4450       4460       4470       4480       4490       4500
           CGTCTGTGCC TTTTACAGAG CTTGCAGTGA ATCCTGTGGA TGTGTTGACG TTGCCATTGG
           GCAGACACGG AAAATGTCTC GAACGTCACT TAGGACACCT ACACAACTGC AACGGTAACC 4510       4520       4530       4540       4550       4560
           AGGATGTGAA CATAGTGGTA GACATTTCGG TGGTTTGTAA CGTAGATGTC AGTTGTGTAG
           TCCTACACTT GTATCACCAT CTGTAAAGCC ACCAAACATT GCATCTACAG TCAACACATC 4570       4580       4590       4600       4610       4620
           TAGATATTAA GCTTGTGGGT GTAATCGACG TGGAAGTATT GGCGATAGTG GTGTTGTTAC
           ATCTATAATT CGAACACCCA CATTAGCTGC ACCTTCATAA CCGCTATCAC CACAACAATG 4630       4640       4650       4660       4670       4680
           ACTTGCTTTT CTGCAGAATC CAAAAAATAA TAAACATGCA TATTATTTGC GTATATGATG
           TGAACGAAAA GACGTCTTAG GTTTTTTATT ATTTGTACGT ATAATAAACG CATATACTAC 4690       4700       4710       4720       4730       4740
           ACTTGTTCCA CCGTCGATGT TGTGTGCGCA T..........
           TGAACAAGGT GGCAGCTACA ACACACGCGT A..........
                                         └─── UL154
```

*FIG. 2E-2*

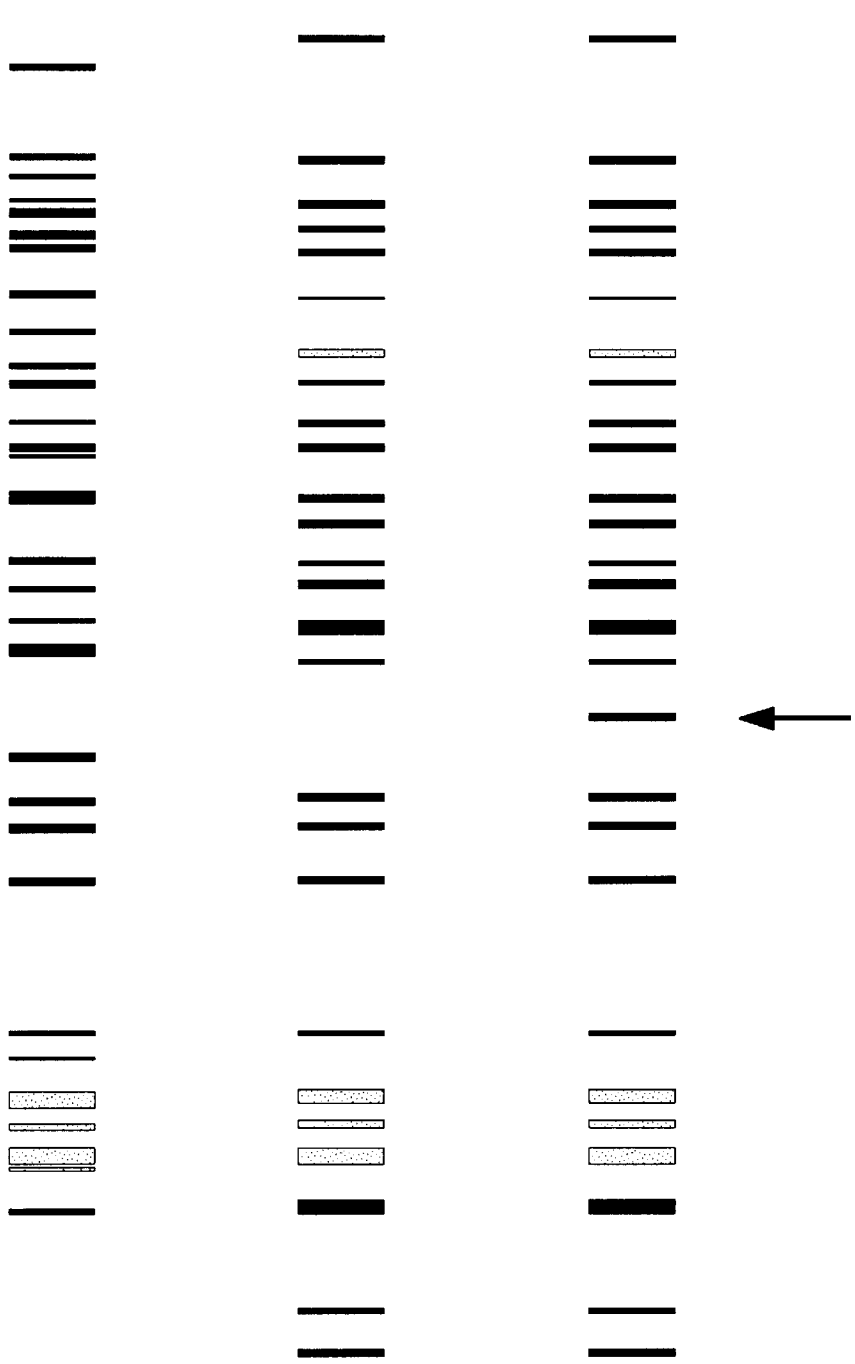
FIG._3

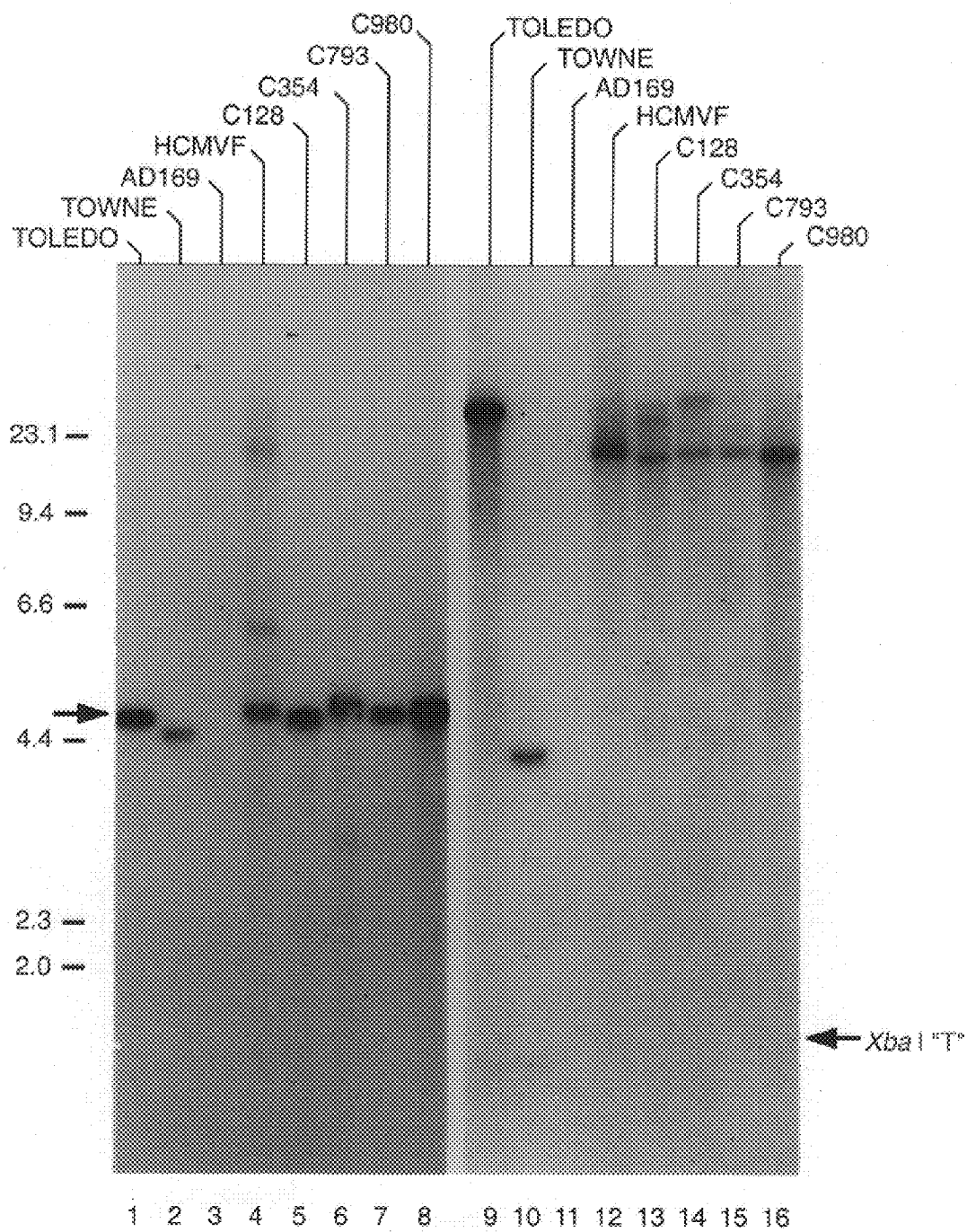
FIG._4

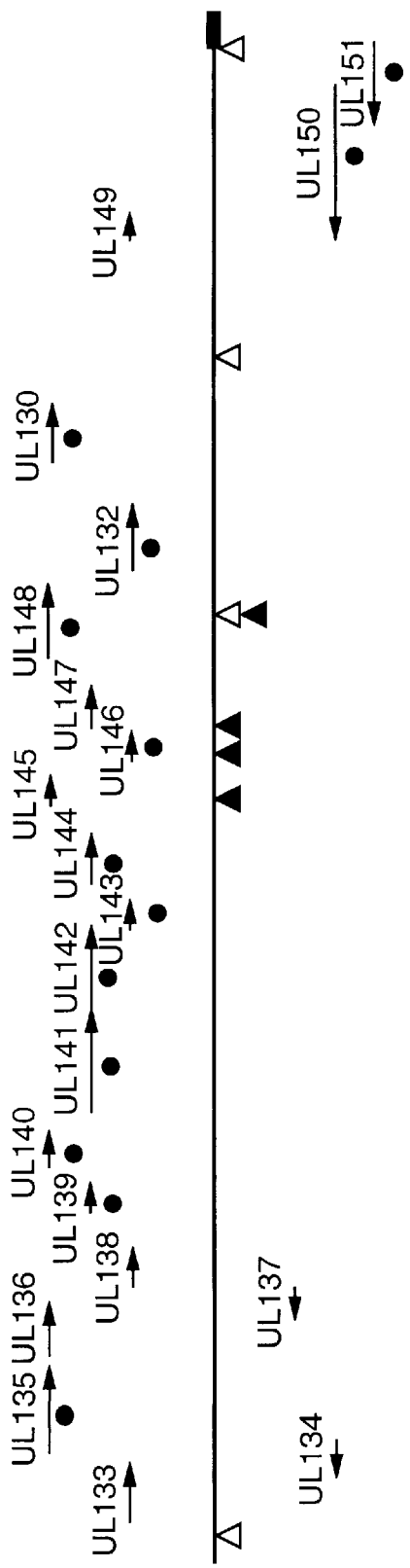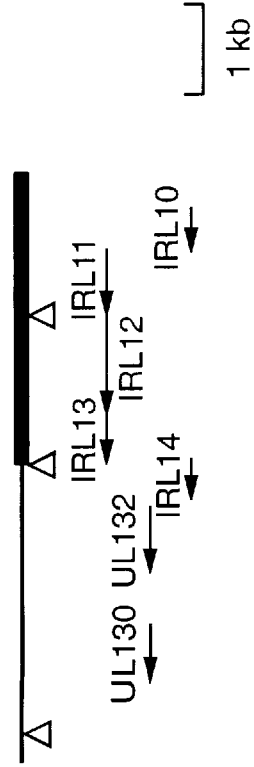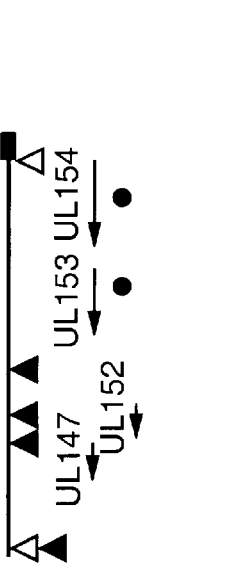
FIG._5

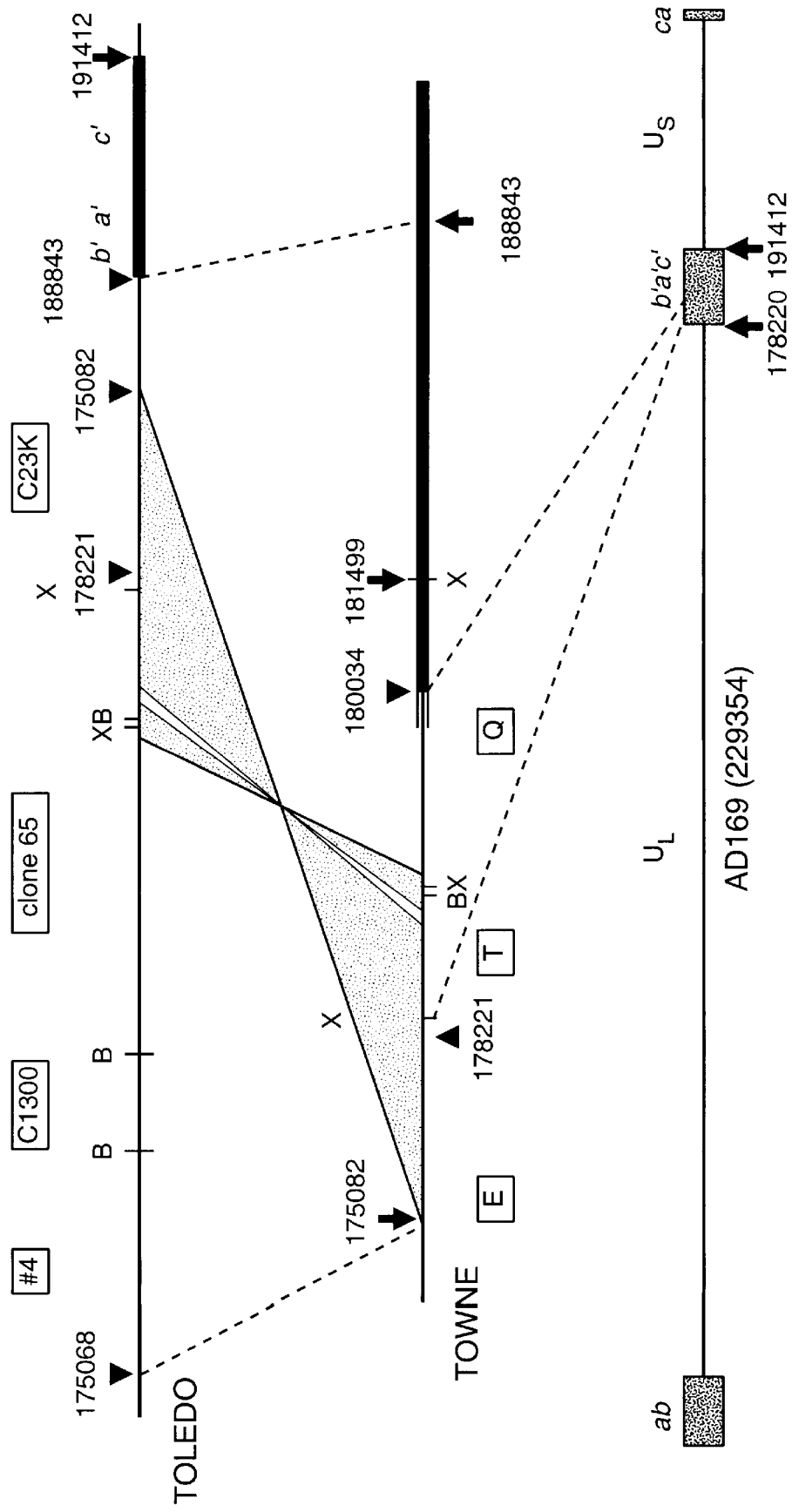
FIG._6

SEQUENCE LISTING (1) GENERAL INFORMATION:

(iii) NUMBER OF SEQUENCES: 27

(2) INFORMATION FOR SEQ ID NO: 1:

(i) SEQUENCE CHARACTERISTICS:
      (A) LENGTH: 4711 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
  (A) ORGANISM: Human CMV
  (B) STRAIN: Towne (ix) FEATURE:
  (A) NAME/KEY: CDS
  (B) LOCATION: complement (845..1321)
  (D) OTHER INFORMATION: /product= "UL147"

(ix) FEATURE:
  (A) NAME/KEY: CDS
  (B) LOCATION: complement (1368..1721)
  (D) OTHER INFORMATION: /product= "UL152"

(ix) FEATURE:
  (A) NAME/KEY: CDS
  (B) LOCATION: complement (2504..3337)
  (D) OTHER INFORMATION: /product= "UL153"

(ix) FEATURE:
  (A) NAME/KEY: CDS
  (B) LOCATION: complement (3515..4711)
  (D) OTHER INFORMATION: /product= "UL154"

(xi) SEQUENCE DESCRIPTION: SEQ ID NO: 1:

```
ATCGGGCGCC AGAGCTAGAT CAGGCGTATC AAATTCCACT GCCAGGCGAC CTGATTCTAA        60
CGGTTCCACG ATCCGGGAGA GCGTTTCTAG ATATAGAGCA AAGCGTACCA CGTCTACCTG       120
CGGTGTAAAA AACTGTTGTG GGCGTTCACC GTCGTTGACC ACGTAAGCCA CGTAGAGGCC       180
AACATTTTCC ACCACGGGTT CTAGCTGCAG GCGGCACGTA AAGCTTAGAA ACGACGGCTG       240
TACGGTTTGG TTCCCGTGAA GCTGAAGCGT CACTTCCTTG CCGGGGCTCA CCGTGCTGTA       300
ACGCCGCACC GAGTCGGTCA TCTGCTCCAG ATCGGTAGAC CAGAAGGGCG TGCAATGCAT       360
ACTGTCCCAG TCGCGACACG CAGCCCAGCC TAGCTCGGTG AAGGGTCGAC GCACACCCGA       420
AAAAGTGTGC TTGAAGACCA GGGGGTCGCC TCGGTAGCTC AGTAGCCGAA CATGCACATA       480
GTCGCGGCTA CGTTGACAGA CGGCCCGTAG ACAGGCAGGA CAAGCGTGAA CAGCAAGCGC       540
AACATGCTGC GGGTTAGAAA ATGCGGCGTG CCGGCCACCG CCCGACTCAT AAACGCTACC       600
AGCATGACGT CTCAGATCAC ACAAGTGACG AGGAGCGTAC CGCAAATCAC TAGGGAAAAG       660
GCCAGCAGAG CCCGATAGTC TTGCTCTTCG CGAACGATCT CGTCCGGTTC CTCGCAGTCT       720
TCGTGGTCCA CAGAAGATGA GGAGCAGGAT TCTTCGTTAA TTTCTGCCAG GATACTAGTG       780
CTGTACCACA CCAGAGCGCT CAGCGTGCCC AGGGCTACCG CACGGTAAAA TAGGGACATG       840
ATCACCAGCG CAATCTGAAG TGGTGGTAGT TCAGTTTCTT GGCGTATTTC CAGAGAAAGG       900
CTTTGTAGGC CGTAGGGACT GGCCAGGCAC CGAACTCAAT ATTGGTAGAC ACTACGTCGT       960
AAATGCGTTG TTCCTCGTCT AAGATTAACC GAAAAAATAG CCGGTTGATG TGACGACGCA      1020
CGGCTTGCGC GTTAGGATTG AGACACTTGG TGCCCTTGTC CTTTAAAATA GCCAGCACTT      1080
CCTGACGATT GCAGCTTTCG CTCGCCGCGA TTGGCTTAAG CAATTCAGTT CCGATTGGCA      1140
GAGTATTCAA CAGAATTTGG TTGTTACAAC GACAGCGTTT GTCGTAATCT TCCAATTCTA      1200
AAAGATGGAC GGCTAGGGGA CATACGACAA ATAACATGTA TGCAGTCAAT TGCATATATC      1260
GTACCGATAA AATGTTAGTG TGCGGATTCA GAATCGGATG ATGCAACCGT CTTAGCATCA      1320
TATCGAAAAA GTATACATAT TACCGATTCA TTATAATTAG GGAATTATTT CCAACGCGGA      1380
CGTTTGTTAG TGACAGCGTT TTCTTCTACA TGCGGTCCAT TACTATCCTT TACTTTTACC      1440
```

```
AATACTCTGT GCCATGAGTT GTCTTTTTTA CCATCCAGCC ATTTGGACAA ATGATGATCG    1500

GGAGCTAAAC ATACAGGTTT ACCTCGAGGA GGCAATAGAT AATGTTGAGG TTTGTCACAC    1560

TCAGGAGGAT TGGGAGGGTC ACGACCAACC CAAAATAAGC CACCTATAGG ATGATGTAAA    1620

GCTTTGTGGG TACACGGACA ACGCAATTCT CTACTGTGAA CCCCATGGTA ATACATAAAT    1680

GCCATCAAAA GACTAATCAG CGAACCAAAA ATTAATCGCA TTCTAATTTT ATTAACTACG    1740

TCACTATCAG TAATTCGTAA TATCCGGTAT TCCCGGAAAA TCACTCAAAA CTGCGTCCAT    1800

GACACATCAA TTCCCGATAA GTACCCCCCT TTGAAATCGG ATCCCCCCAC ATACCAATCA    1860

ATCACACAAC ACACAGGTTT AAAAATCGAT CACACGTCAA TTAGGTTTCA AAATCGATAC    1920

TGTTTATTAT CAGGAATCTA GACTAATTCT ACAATGACAG CTCTGAATTT CTCTCTCGTC    1980

TTTCTTGTCA GGTTCTCATC ATCAATCTTC ACTTCCACCC ATCGAGGAGT CATCGTCGCT    2040

CCAAAACCCT TTGGGGTCGC TGGTTGGAAA AGTCTCTGAC ACGATCCAGG CACCCCGTAC    2100

CCAGTCCGAC TGATCTAGCT TACGGAGCAT CTCAACAGGC ATGAGCTGCA GGGCCACGGC    2160

TGTCACGGCA GGGATTATTA CTACCGTTCA GGTAAACTGT ATCTCCCTGA GTTACCGTGA    2220

TGGGTCTTTC TACATGTTGA CTTTGCGTAA AAAATCGCCG GTAAAATGTT TTTTCTTGTT    2280

CATGTAAAAG TACCGGAACT AAAATGCTAG TTAGAATGGT TGCAGTTGCT ATTAGCGCGG    2340

CTAGTAACAG TAGTTTAGTG TTACATTGTA TACCCATGTT TTTAATAACT ATGAATATTC    2400

TGCTTCACAC CATAAGTGCT TAACCCACAA AAACCACACG GAGACATTAT TGGCTAAAAA    2460

TAAAAACAAA AGTTTATTGA TGTGCATGTT AGGTTTTAGT CTAAAATTCA TCTGGGTCGT    2520

ATTTGGGAAG TTTTGTATAA CGCGGTCTTC TGGGGACGCG ACGGCTACCC ATGTATAAGG    2580

CTATAAGTGC CACAGATACC ACTATACCCG CCCATACAGC ATGAATTCCC AGGGGAATGT    2640

TAGTGTTTTT TACAGTTTTT ATTACATTGT CCCACGTTCT GCTATTATGC TGGTCTGATT    2700

CCTCTTTTGT TTTACATTTA TCAGGTATAG GAGACGATGT TGCAGTTCCT GATAACACGG    2760

TTAAATAGTA GTTTTCCTTT TTACCGTCAC TGTAACGTTG CAAAACGTAT TTTCCAGCGT    2820

GTTCGGTAGT TACGTTGTAT ATAGTGAGAG AGGTCTTATT GCAGTCTAAA CACATGCCGT    2880

TCAGTGGGGA AGTTGAATAA TAATGTCCAA TGCTGCACAG TTGGTGTGCG CGAGGTCCAT    2940

ATTTTATCCA TTCTATATCG TGCCATACAT CCGTTCTACT GCAGTTTTTC AAAGTGACGT    3000

ATCCACCGAC ATATCCTGTT ACATTAATTA CTTCGTAATT TAAATTAGAG TGTTTATAAA    3060

CGGTGTACAA ACTGCCATTG CAAGTTATGT TGCTGGTATT CAACCAGGGA GTAGTACTAT    3120

GAATGGTAGA AAACGTTAAT GTTGGCGTAG CGCTTGACGA TGATTTTGAA AGCGTTGAAG    3180

TGGTTGCTGA TGCGACTGAA GAAGCGGTAG AGGGTTTGTG CGTGGTTCCA TTTGCGATAG    3240

CTGAAGTGCT GTTAGCATCG GTGACAGAGT TAGAAGAATT TGTGATAGTG GAGGCGGTGG    3300

AGGTAAAGGC AATTGCACGG ACAGGAGCAC GTGTCATTGC AACCTTCAGA TATCGTAATC    3360

ATCAGTAACG TCCACTTAAC CGTAAATCTC CAGTCCATAA CGTTATTAAA TTTCGGTTAA    3420

CGGGCATTGA TGTTTCTTCG GACGTTGTTG ATCTTTCTTG CCCGTTTATT TTCTGATATG    3480

GTCTCATAAG ACATTTATCC GGAAACGTTG CTTAGTCCTC GTGCTCAGGA TTGTATCGAA    3540

CTATGAATTC TGATTCACTT ATATCGTCAC TTAATGGATG ATATTTTTA TTTAGAGCTC    3600

GTCGGACGAA AAATAGGAGA ATGCAGGCTA CACAAATTAA TGCTAACGTC CACGTAGTGC    3660

GTCTGCCGTG TGATGTGTTA GAATGATTGT TATAGCGGTA TAAATGATCT ATAGATGATG    3720

TGGCTGTATT GTCTTCATAA TTGGTCGGTT TATGAGAAGT GTCCCATTCG TGCTTTGGTT    3780
```

-continued

```
CTTCACATAC CCAGGGATTC ACGTGTGTCC CGTTTGTGTT GTTTCTAGGA TGTATTTGCA     3840

GATTAAAGTT TTGATTTTGT TCGGAGGGAT GCCCAGTTTT ATAACATCGA AAGCTATATT     3900

TACCAGAATG AGTAAAATTA AGACCGTACA GAGATAAAGA TAAATTACGA TCGCATGTAA     3960

AACATAAATC ATAGTGATGT TTTAGATAAT TTGTGTGCCA CTCACATAGT ATACGCGAAT     4020

GGAGGATTTT CAATGAATGG TTATGATATT TTCCATTTCT TATGTTGGGA TGGGTGTATT     4080

TTCCGTGTGT GGATATATTA AAATGTCTAA GCCAGGCTGT TTTGTAGCAC GATGTGATGG     4140

TTAGGTTGTG TGTTATAGTA ATATTGTCTC CTTGTGCCGC CTCCAATAAT GTTTCAGATT     4200

CTTTTGATAT CGTATTATTT GTACTGTTAG GCGATGAGCA AGTTGGAAGC GGTGTAGTGA     4260

CGTTTTCATT TGCATTTATC ATAGTAGTAG TGTTGGTTGA TAATGATATA GTTTGCAAAG     4320

TCACAGTACT ATCGGTTACA TGCTGTGTCG ATGAATTCGT GTCGCCGTTT GGTGAAGTTG     4380

TTATTACAGT TACGTTAGTT GTAGATGTTT GGGTAGATAT GGTGGAAATA GTTGAGGTCA     4440

CGTCTGTGCC TTTTACAGAG CTTGCAGTGA ATCCTGTGGA TGTGTTGACG TTGCCATTGG     4500

AGGATGTGAA CATAGTGGTA GACATTTCGG TGGTTTGTAA CGTAGATGTC AGTTGTGTAG     4560

TAGATATTAA GCTTGTGGGT GTAATCGACG TGGAAGTATT GGCGATAGTG GTGTTGTTAC     4620

ACTTGCTTTT CTGCAGAATC CAAAAAATAA TAAACATGCA TATTATTTGC GTATATGATG     4680

ACTTGTTCCA CCGTCGATGT TGTGTGCGCA T                                    4711
```

(2) INFORMATION FOR SEQ ID NO: 2:

(i) SEQUENCE CHARACTERISTICS:
        (A) LENGTH: 159 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Met Leu Arg Arg Leu His His Pro Ile Leu Asn Pro His Thr Asn
  1               5                  10                  15

Ile Leu Ser Val Arg Tyr Met Gln Leu Thr Ala Tyr Met Leu Phe Val
             20                  25                  30

Val Cys Pro Leu Ala Val His Leu Leu Glu Leu Glu Asp Tyr Asp Lys
         35                  40                  45

Arg Cys Arg Cys Asn Asn Gln Ile Leu Leu Asn Thr Leu Pro Ile Gly
     50                  55                  60

Thr Glu Leu Leu Lys Pro Ile Ala Ala Ser Glu Ser Cys Asn Arg Gln
 65                  70                  75                  80

Glu Val Leu Ala Ile Leu Lys Asp Lys Gly Thr Lys Cys Leu Asn Pro
                 85                  90                  95

Asn Ala Gln Ala Val Arg Arg His Ile Asn Arg Leu Phe Phe Arg Leu
            100                 105                 110

Ile Leu Asp Glu Glu Gln Arg Ile Tyr Asp Val Val Ser Thr Asn Ile
        115                 120                 125

Glu Phe Gly Ala Trp Pro Val Pro Thr Ala Tyr Lys Ala Phe Leu Trp
    130                 135                 140

Lys Tyr Ala Lys Lys Leu Asn Tyr His His Phe Arg Leu Arg Trp
145                 150                 155
```

(2) INFORMATION FOR SEQ ID NO: 3:

(i) SEQUENCE CHARACTERISTICS:
        (A) LENGTH: 118 amino acids (B) TYPE: amino acid
        (D) TOPOLOGY: linear (ii) MOLECULE TYPE: protein (xi) SEQUENCE DESCRIPTION: SEQ ID NO: 3:

Met Arg Leu Ile Phe Gly Ser Leu Ile Ser Leu Leu Met Ala Phe Met
 1               5                  10                  15

Tyr Tyr His Gly Val His Ser Arg Glu Leu Arg Cys Pro Cys Thr His
                20                  25                  30

Lys Ala Leu His His Pro Ile Gly Gly Leu Phe Trp Val Gly Arg Asp
            35                  40                  45

Pro Pro Asn Pro Pro Glu Cys Asp Lys Pro Gln His Tyr Leu Leu Pro
    50                  55                  60

Pro Arg Gly Lys Pro Val Cys Leu Ala Pro Asp His His Leu Ser Lys
65                  70                  75                  80

Trp Leu Asp Gly Lys Lys Asp Asn Ser Trp His Arg Val Leu Val Lys
                85                  90                  95

Val Lys Asp Ser Asn Gly Pro His Val Glu Glu Asn Ala Val Thr Asn
                100                 105                 110

Lys Arg Pro Arg Trp Lys
            115

(2) INFORMATION FOR SEQ ID NO: 4:

(i) SEQUENCE CHARACTERISTICS:
        (A) LENGTH: 278 amino acids
        (B) TYPE: amino acid
        (D) TOPOLOGY: linear (ii) MOLECULE TYPE: protein (xi) SEQUENCE DESCRIPTION: SEQ ID NO: 4:

Met Thr Arg Ala Pro Val Arg Ala Ile Ala Phe Thr Ser Thr Ala Ser
 1               5                  10                  15

Thr Ile Thr Asn Ser Ser Asn Ser Val Thr Asp Ala Asn Ser Thr Ser
                20                  25                  30

Ala Ile Ala Asn Gly Thr Thr His Lys Pro Ser Thr Ala Ser Ser Val
            35                  40                  45

Ala Ser Ala Thr Thr Ser Thr Leu Ser Lys Ser Ser Ser Ser Ala Thr
    50                  55                  60

Pro Thr Leu Thr Phe Ser Thr Ile His Ser Thr Thr Pro Trp Leu Asn
65                  70                  75                  80

Thr Ser Asn Ile Thr Cys Asn Gly Ser Leu Tyr Thr Val Tyr Lys His
                85                  90                  95

Ser Asn Leu Asn Tyr Glu Val Ile Asn Val Thr Gly Tyr Val Gly Gly
                100                 105                 110

Tyr Val Thr Leu Lys Asn Cys Ser Arg Thr Asp Val Trp His Asp Ile
            115                 120                 125

Glu Trp Ile Lys Tyr Gly Pro Arg Ala His Gln Leu Cys Ser Ile Gly
    130                 135                 140

His Tyr Tyr Ser Thr Ser Pro Leu Asn Gly Met Cys Leu Asp Cys Asn
145                 150                 155                 160

Lys Thr Ser Leu Thr Ile Tyr Asn Val Thr Thr Glu His Ala Gly Lys
                165                 170                 175

Tyr Val Leu Gln Arg Tyr Ser Asp Gly Lys Lys Glu Asn Tyr Tyr Leu
            180                 185                 190

```
Thr Val Leu Ser Gly Thr Ala Thr Ser Ser Pro Ile Pro Asp Lys Cys
            195                 200                 205

Lys Thr Lys Glu Glu Ser Asp Gln His Asn Ser Arg Thr Trp Asp Asn
            210                 215                 220

Val Ile Lys Thr Val Lys Asn Thr Asn Ile Pro Leu Gly Ile His Ala
225                 230                 235                 240

Val Trp Ala Gly Ile Val Val Ser Val Ala Leu Ile Ala Leu Tyr Met
                245                 250                 255

Gly Ser Arg Arg Val Pro Arg Arg Pro Arg Tyr Thr Lys Leu Pro Lys
            260                 265                 270

Tyr Asp Pro Asp Glu Phe
            275

(2) INFORMATION FOR SEQ ID NO: 5:

(i) SEQUENCE CHARACTERISTICS:
        (A) LENGTH: 399 amino acids
        (B) TYPE: amino acid
        (D) TOPOLOGY: linear (ii) MOLECULE TYPE: protein (xi) SEQUENCE DESCRIPTION: SEQ ID NO: 5:

Met Arg Thr Gln His Arg Arg Trp Asn Lys Ser Ser Tyr Thr Gln Ile
1               5                   10                  15

Ile Cys Met Phe Ile Ile Phe Trp Ile Leu Gln Lys Ser Lys Cys Asn
                20                  25                  30

Asn Thr Thr Ile Ala Asn Thr Ser Thr Ser Ile Thr Pro Thr Ser Leu
            35                  40                  45

Ile Ser Thr Thr Gln Leu Thr Ser Thr Leu Gln Thr Thr Glu Met Ser
        50                  55                  60

Thr Thr Met Phe Thr Ser Ser Asn Gly Asn Val Asn Thr Ser Thr Gly
65                  70                  75                  80

Phe Thr Ala Ser Ser Val Lys Gly Thr Asp Val Thr Ser Thr Ile Ser
                85                  90                  95

Thr Ile Ser Thr Gln Thr Ser Thr Thr Asn Val Thr Val Ile Thr Thr
            100                 105                 110

Ser Pro Asn Gly Asp Thr Asn Ser Ser Thr Gln His Val Thr Asp Ser
        115                 120                 125

Thr Val Thr Leu Gln Thr Ile Ser Leu Ser Thr Asn Thr Thr Thr Met
130                 135                 140

Ile Asn Ala Asn Glu Asn Val Thr Thr Pro Leu Pro Thr Cys Ser Ser
145                 150                 155                 160

Pro Asn Ser Thr Asn Asn Thr Ile Ser Lys Glu Ser Glu Thr Leu Leu
                165                 170                 175

Glu Ala Ala Gln Gly Asp Asn Ile Thr Ile Thr His Asn Leu Thr Ile
            180                 185                 190

Thr Ser Cys Tyr Lys Thr Ala Trp Leu Arg His Phe Asn Ile Ser Thr
        195                 200                 205

His Gly Lys Tyr Thr His Pro Asn Ile Arg Asn Gly Lys Tyr His Asn
    210                 215                 220

His Ser Leu Lys Ile Leu His Ser Arg Ile Leu Cys Glu Trp His Thr
225                 230                 235                 240

Asn Tyr Leu Lys His His Tyr Asp Leu Cys Phe Thr Cys Asp Arg Asn
                245                 250                 255

Leu Ser Leu Ser Leu Tyr Gly Leu Asn Phe Thr His Ser Gly Lys Tyr
```

```
                       260                 265                 270
Ser Phe Arg Cys Tyr Lys Thr Gly His Pro Ser Glu Gln Asn Gln Asn
            275                 280                 285

Phe Asn Leu Gln Ile His Pro Arg Asn Thr Asn Gly Thr His Val
290                 295                 300

Asn Pro Trp Val Cys Glu Glu Pro Lys His Glu Trp Asp Thr Ser His
305             310                 315                 320

Lys Pro Thr Asn Tyr Glu Asp Asn Thr Ala Thr Ser Ser Ile Asp His
                325                 330                 335

Leu Tyr Arg Tyr Asn Asn His Ser Asn Thr Ser His Gly Arg Arg Thr
            340                 345                 350

Thr Trp Thr Leu Ala Leu Ile Cys Val Ala Cys Ile Leu Leu Phe Phe
            355                 360                 365

Val Arg Arg Ala Leu Asn Lys Lys Tyr His Pro Leu Ser Asp Asp Ile
370                 375                 380

Ser Glu Ser Glu Phe Ile Val Arg Tyr Asn Pro Glu His Glu Asp
385                 390                 395
```

(2) INFORMATION FOR SEQ ID NO: 6:

(i) SEQUENCE CHARACTERISTICS:
        (A) LENGTH: 18318 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Human CMV
        (B) STRAIN: Toledo (ix) FEATURE:
        (A) NAME/KEY: CDS
        (B) LOCATION: 511..1281
        (D) OTHER INFORMATION: /product = "UL133"

(ix) FEATURE:
        (A) NAME/KEY: CDS
        (B) LOCATION: 1401..2384
        (D) OTHER INFORMATION: /product = "UL135"

(ix) FEATURE:
        (A) NAME/KEY: CDS
        (B) LOCATION: 2478..3197
        (D) OTHER INFORMATION: /product = "UL136"

(ix) FEATURE:
        (A) NAME/KEY: CDS
        (B) LOCATION: 3283..3789
        (D) OTHER INFORMATION: /product = "UL138"

(ix) FEATURE:
        (A) NAME/KEY: CDS
        (B) LOCATION: 4355..4759
        (D) OTHER INFORMATION: /product = "UL139"

(ix) FEATURE:
        (A) NAME/KEY: CDS
        (B) LOCATION: 4944..5285
        (D) OTHER INFORMATION: /product = "UL140"

(ix) FEATURE:
        (A) NAME/KEY: CDS
        (B) LOCATION: 5558..6832
        (D) OTHER INFORMATION: /product = "UL141"

```
(ix) FEATURE:
    (A) NAME/KEY: CDS
    (B) LOCATION: 6908..7825
    (D) OTHER INFORMATION: /product = "UL142"

(ix) FEATURE:
    (A) NAME/KEY: CDS
    (B) LOCATION: 7813..8088
    (D) OTHER INFORMATION: /product = "UL143"

(ix) FEATURE:
    (A) NAME/KEY: CDS
    (B) LOCATION: 8468..8995
    (D) OTHER INFORMATION: /product = "UL144"

(ix) FEATURE:
    (A) NAME/KEY: CDS
    (B) LOCATION: 9327..9626
    (D) OTHER INFORMATION: /product = "UL145"

(ix) FEATURE:
    (A) NAME/KEY: CDS
    (B) LOCATION: 9910..10260
    (D) OTHER INFORMATION: /product = "UL146"

(ix) FEATURE:
    (A) NAME/KEY: CDS
    (B) LOCATION: 10328..10804
    (D) OTHER INFORMATION: /product = "UL147"

(ix) FEATURE:
    (A) NAME/KEY: CDS
    (B) LOCATION: 11106..12053
    (D) OTHER INFORMATION: /product = "UL148"

(ix) FEATURE:
    (A) NAME/KEY: CDS
    (B) LOCATION: 12133..12942
    (D) OTHER INFORMATION: /product = "UL132"

(ix) FEATURE:
    (A) NAME/KEY: CDS
    (B) LOCATION: 13569..14210
    (D) OTHER INFORMATION: /product = "UL130"

(ix) FEATURE:
    (A) NAME/KEY: CDS
    (B) LOCATION: 16216..16581
    (D) OTHER INFORMATION: /product = "UL149"

(ix) FEATURE:
    (A) NAME/KEY: CDS
    (B) LOCATION: 1004..1528
    (D) OTHER INFORMATION: /product = "UL134"

(ix) FEATURE:
    (A) NAME/KEY: CDS
    (B) LOCATION: 3063..3350
    (D) OTHER INFORMATION: /product = "UL137"

(ix) FEATURE:
    (A) NAME/KEY: CDS
    (B) LOCATION: 16337..18262
    (D) OTHER INFORMATION: /product = "UL150"

(ix) FEATURE:
    (A) NAME/KEY: CDS
    (B) LOCATION: 17752..18759
    (D) OTHER INFORMATION: /product = "UL151"

(xi) SEQUENCE DESCRIPTION: SEQ ID NO: 6:

CGCTGTAGGG ATAAATAGTG CGATGGCGTT TGTGGGAGAA CGCAGTAGCG ATGGGTTGCG      60

ACGTGCACGA TCCTTCGTGG CAATGCCAAT GGGGCGTTCC CACGATTATC GTGGCCTGGA     120

TAACATGCGC GGCTTTAGGA ATTTGGTGTT TGGCGGGATC GTCGGCGGAT GTCTCTTCGG     180
```

```
                                          -continued

GACCCGGCAT CGCAGCCGTA GTCGGCTGTT CTGTTTTCAT GATTTTCCTC TGCGCGTATC      240

TCATCCGTTA CCGGGAATTC TTCAAAGACT CCGTAATCGA CCTCCTTACC TGCCGATGGG      300

TTCGCTACTG CAGCTGCAGC TGTAAGTGCA GCTGCAAATG CATCTCGGGC CCCTGTAGCC      360

GCTGCTGTTC AGCGTGTTAC AAGGAGACGA TGATTTACGA CATGGTCCAA TACGGTCATC      420

GACGGCGTCC CGGACACGGC GACGATCCCG ACAGGGTGAT CTGCGAGATA GTCGAGAGTC      480

CCCCGGTTTC GGCGCCGACG GTGTCCGTCC CCCCGCCGTC GGAGGAGTCC CACCAGCCCG      540

TCATCCCACC GCAGCCGCCA GCACCGACAT CGGAACCCAA ACCGAAGAAA GGTAGGGCGA      600

AAGATAAACC GAAGGGTAGA CCGAAAGACA AACCTCCGTG CGAACCGACG GTGAGTTCAC      660

AACCACCGTC GCAGCCGACG GCAATGCCCG GCGGTCCGCC CGACGCGCCT CCCCCCGCCA      720

TGCCGCAGAT GCCACCCGGC GTGGCCGAGG CGGTACAAGC TGCCGTGCAG GCGGCCGTGG      780

CCGCGGCTCT ACAACAACAG CAGCAGCATC AGACCGGAAC GTAACCCGCC CCCGGTGCGA      840

TAAGGAATTT TCCGACTTGG CGCACATCTC CTTCCTCAAT GTTTGGACAA TAAACACATT      900

CCTTGCCAAA AAATGACGTT TCCAGAAATC CAAGGCATAA ATGTCCGTAC ACCGCCCTT       960

CCCAACACGG AGTTTGAGAT TCCAAGCAGG AGAGAAGATC ATGGTGTGGA TATGGCTCGG     1020

CATCGGGCTC CTCGGCGGTA CCGGACTGGC TTCCCTGGTC CTGGCCATTT CCTTATTTAC     1080

CCAGCGCCGA GGCCGCAAGC GATCCGACGA GACTTCGTCG CGAGGCCGGC TCCCGGGTGC     1140

TGCTTCTGAT AAGCGTGGTG CCTGCGCGTG CTGCTATCGA AATCCGAAAG AAGACGTCGT     1200

CGAGCCGCTG GATCTGGAAC TGGGGCTCAT GCGGGTGGAC ACCCACCCGC CGACGCCGCA     1260

GGTGCCGCGG TGTACGTCGC TCTACATAGG AGAGGATGGT CTGCCGATAG ATAAACCCGA     1320

GTTTCCTCCG GCGCGGTTCG AGATCCCCGA CGTATCCACG CCGGGAACGC CGACCAGCAT     1380

CGGCCGATCT CCGTCGCATT GCTCCTCGTC GAGCTCTTTG TCGTCCTCGA CCAGCGTCGA     1440

CACGGTGCTG TATCAGCCGC CGCCATCCTG GAAGCCACCT CCGCCGCCCG GGCGCAAGAA     1500

GCGGCCGCCT ACGCCGCCGG TCCGGGCCCC CACCACGCGG CTGTCGTCGC ACAGACCCCC     1560

GACGCCGATA CCCGCGCCGC GTAAGAACCT GAGCACGCCG CCCACCAAGA AAACGCCGCC     1620

GCCCACGAAA CCCAAGCCGG TCGGCTGGAC ACCGCCGGTG ACACCCAGGC CCTTCCCGAA     1680

AACGCCGACG CCACAAAAGC CGCCGCGGAA TCCGAGACTA CCGCGCACCG TCGGTCTGGA     1740

GAATCTCTCG AAGGTGGGAC TCTCGTGTCC CTGTCCCCGA CCCCGCACGC CGACGGAGCC     1800

GACCACGCTG CCTATCGTGT CGGTTTCCGA GCTAGCCCCG CCTCCTCGAT GGTCGGACAT     1860

CGAGGAACTC TTGGAACAGG CGGTGCAGAG CGTCATGAAG GACGCCGAGT CGATGCAGAT     1920

GACCTGAGAC CGAAAGAGCG AGCGCGTCCG TTGTACAGTT GTATAGCAGC ACACGCCTTC     1980

CCTCTTTTTC ACCGCAGCTA AGAGAGAGAA AGAGAGTATG TCAGTCAAGG GCGTGGAGAT     2040

GCCAGAAATG ACGTGGGACT TGGACGTTAG AAATAAATGG CGGCGTCGAA AGGCCCTGAG     2100

TCGCATTCAC CGGTTCTGGG AATGTCGGCT ACGGGTGTGG TGGCTGAGTG ACGCCGGCGT     2160

AAGAGAAACC GACCCACCGC GTCCCCGACG CCGCCCGACT TGGATGACCG CGGTGTTTCA     2220

CGTTATCTGT GCCGTTTTGC TTACGCTTAT GATTATGGCC ATCGGCGCGC TCATCGCGTA     2280

CTTAAGATAT TACCACCAGG ACAGTTGGCG AGACATGCTC CACGATCTAT TTTGCGGCTG     2340

TCATTATCCC GAGAAGTGCC GTCGGCACCA CGAGCGGCAG AGAAGGAGAC GGCAAGCCAT     2400

GGATGTGCCC GACCCGGAAC TCGGCGACCC GGCCCGCCGG CCGTTGAACG GAGCTATGTA     2460

CTACGGCAGC GGCTGTCGCT TCGACACGGT GGAAATGGTG GACGAGACGA GACCCGCGCC     2520

GCCGGCGCTG TCATCGCCCG AAACCGGCGA CGATAGCAAC GACGACGCGG TTGCCGGCGG     2580
```

```
AGGTGCTGGC GGGGTAACAT CACCCGCGAC TCGTACGACG TCGCCGAACG CACTGCTGCC    2640

AGAATGGATG GATGCGGTGC ATGTGGCGGT CCAAGCCGCC GTTCAAGCGA CCGTGCAAGT    2700

AAGTGGCCCG CGGGAGAACG CCGTATCTCC CGCTACGTAA GAGGGTTGAG GGGGCCGTTC    2760

CCGCGCGAGT GCTGTACAAA AGAGAGAGAC TGGGACGTAG ATCCGGACAG AGGACGGTCA    2820

CCATGGACGA TCTGCCGCTG AATGTCGGGT TACCCATCAT CGGCGTGATG CTCGTGCTGA    2880

TCGTGGCCAT CCTCTGCTAT CTGGCTTACC ACTGGCACGA CACCTTCAAA CTGGTGCGCA    2940

TGTTTCTGAG CTACCGCTGG CTGATCCGCT GTTGCGAGCT GTACGGGGAG TACGAGCGCC    3000

GGTTCGCGGA CCTGTCGTCT CTGGGCCTCG GCGCCGTACG GCGGGAGTCG GACAGACGAT    3060

ACCGTTTCTC CGAACGGCCC GACGAGATCT TGGTCCGTTG GGAGGAAGTG TCTTCCCAGT    3120

GCAGCTACGC GTCGTCGCGG ATAACAGACC GCCGTGTGGG TTCATCGTCT TCGTCGTCGG    3180

TCCACGTCGC TAGCCAGAGA AACAGCGTGC CTCCGCCGGA CATGGCGGTG ACGGCGCCGC    3240

TGACCGACGT CGATCTGTTG AAACCCGTGA CGGGATCCGC GACGCAGTTC ACCACCGTAG    3300

CCATGGTACA TTATCATCAA GAGTACACGT GAATGAGAAA AGAAAAAAG AGGGGAGCGG    3360

ATCGCGATAA TGTCGCTTTG ACATTCTCTG CTCGATCTAC TCAGCGTCTG CACGAAACGG    3420

CATCCGCACG GAGGCGAGCC CAAGCGTATC TGCAGCAAGC GGTTCTTTCC CTCGGTGATG    3480

GTGGCAGCAT CGGTGGCGGG AGCTTGTTCG GACGATGGAC GGTGAGGAGT CCCTGGCGAT    3540

CAGGCGGCTC CCGGGTGTGG AGTTCAACGG GTGGTAATGG TGGCGGTGAT CGGTGTTAGA    3600

AAACGGTGGC CCTGGCAAAC ATATATCTAC TGTAAACCCT CTGCTCTGTT AATAAAAAGC    3660

ACACTTTTCA CATGAGTTCG TAATTTTATT GTGTAGTGGA AATTTTTACG TCATTGGGAA    3720

ACCCCAGAAT GAAAGAGTAT AATGTGCATA TCACCGGGGG TTCCCTGTCA GTACGAATGT    3780

ACACAACGCG GGTTACATTA CGATAAACTT TCCGGTAAAA CGATGCCGAT ACAGCGTGTA    3840

TAACGCTGAT TGTTACGACA AACGAGTTGG TATATCCATT ATATAGTAAC GAACATGCTG    3900

TGGATATTAG TTTTATTTGC ACTCGCCGCA TCGGCGAGTG AAACCACTAC AGGTACCAGC    3960

TCTAATTCCA GTCAATCTAC TAGTGCTACC GCCAACACGA CCGTATCGAC ATGTATTAAT    4020

GCCTCTAACG GCAGTAGCTG GACAGTACCA CAGCTCGCGC TGCTTGCCGC TAGCGGCTGG    4080

ACATTATCTG GACTCCTTCT CTTATTTACC TGCTGCTTTT GCTGCTTTTG GCTAGTACGT    4140

AAAATCTGCA GCTGCTGCGG CAACTCCTCC GAGTCAGAGA GCAAAACAAC CCACGCGTAC    4200

ACCAATGCCG CATTCACTTC TTCCGACGCA ACGTTACCCA TGGGCACTAC AGGGTCGTAC    4260

ACTCCCCCAC AGGACGGCTC ATTTCCACCT CCGCCTCGGT GACGTAGGCT AAACCGAAAC    4320

CCACGTTGAA CCTAACGCGG TTTCGGAAGG CCTGAGACGT CACTTTCACA ATGACGTCCG    4380

TATACACGTT CATCATAAAA CACCGTAGAG GCTAAGGCTT CGGTAGGGAG AGACCTCAAC    4440

TGTTCCTGAT GAGCACCCGT GCTCTCATCT CTTCAGACTT GTCATGACCC CCGCTCAGAC    4500

TAACGCGACT ACCACCGTGC ACCCGCACGA CGCAAAAAAC GGCAGCGGCG GTAGTGCCCT    4560

GCCGACCCTC GTCGTTTTCG GCTTTATCGT TACGCTACTT TTCTTTCTCT TTATGCTCTA    4620

CTTTTGGAAC AACGACGTGT TCCGTAAGCT GCTCCGTGCG CTTGGATCCA GCGCTGTTGC    4680

GACCGCTTCG ACGCGTGGCA AGACGAGGTC ATCTACCGTC GTCCATCACG TCGTTCCCAG    4740

AGCGACGACG AGAGTCGTAC TAACAGCGTG TCATCGTACG TTCTTTTATC ACCCGCGTCC    4800

GATGGCGGTT TTGACAACCC GGCACTGACA GAGGCCGTCG ACAGCGTGGA CGACTGGGCG    4860

ACCACCTCGG TTTTCTACGC CACGTCCGAC GAAACGGCGG ACGCCGAGCG CCGAGACTCG    4920
```

-continued

```
CAGCAACTGC TCATCGAGCT TCCGCCGGAG CCGCTCCCGC CCGACGTGGT GGCGGCCATG    4980

CAGAAAGCAG TGAAACGCGC TGTACAGAAC GCACTACGAC ACAGCCACGA CTCTTGGCAG    5040

CTTCATCAGA CCCTGTGACG CCAGATGAAC GTTCCTTCTT AAACATCCGA GGTAGCAATG    5100

AGACAGGTCG CGTACCGCCG GCGACGCGAG AGTTCCTGCG CGGTGCTGGT CCACCACGTC    5160

GGCCGCGACG GCGACGGCGA GGGGGAGGCA GCAAAAAAGA CCTGCAAAAA AACCGGACGC    5220

TCAGTTGCGG GCATCCCGGG CGAGAAGCTG CGTCGCACGG TGGTCACCAC CACGCCGGCC    5280

CGACGTTTGA GCGGCCGACA CACGGAGCAG GAGCAGGCGG GCATGCGTCT CTGTGAAAAA    5340

GGGAAGAAAA GAATCATCAT GTGCCGCCGG GAGTCGCTCC GAACTCTGCC GTGGCTGTTC    5400

TGGGTGCTGT TGAGCTGCCC GCGACTCCTC GAATATTCTT CCTCTTCGTT CCCCTTCGCC    5460

ACCGCTGACA TTGCCGAAAA GATGTGGGCC GAGAATTATG AGACCACGTC GCCGGCGCCG    5520

GTGTTGGTCG CCGAGGGAGA GCAAGTTACC ATCCCCTGCA CGGTCATGAC ACACTCCTGG    5580

CCCATGGTCT CCATTCGCGC ACGTTTCTGT CGTTCCCACG ACGGCAGCGA CGAGCTCATC    5640

CTGGACGCCG TCAAAGGCCA TCGGCTGATG AACGGACTCC AGTACCGCCT GCCGTACGCC    5700

ACTTGGAATT TCTCGCAATT GCATCTCGGC CAAATATTCT CGCTTACTTT TAACGTATCG    5760

ATGGACACAG CCGGCATGTA CGAATGCGTG CTACGCAACT ACAGCCACGG CCTCATCATG    5820

CAACGCTTCG TAATTCTCAC GCAGCTGGAG ACGCTCAGCC GGCCCGACGA ACCTTGCTGC    5880

ACACCGGCGT TAGGTCGCTA CTCGCTGGGA GACCAGATCT GGTCGCCGAC GCCCTGGCGT    5940

CTACGGAATC ACGACTGCGG AACGTACCGC GGCTTTCAAC GCAACTACTT CTATATCGGC    6000

CGCGCCGACG CCGAGGATTG CTGGAAACCC GCATGTCCGG ACGAGGAACC CGACCGCTGT    6060

TGGACAGTGA TACAGCGTTA CCGGCTCCCC GGCGACTGCT ACCGTTCGCA GCCACACCCG    6120

CCGAAATTTT TACCGGTGAC GCCAGCACCG CCGGCCGACA TAGACACCGG GATGTCTCCC    6180

TGGGCCACTC GGGGAATCGC GGCGTTTTTG GGGTTTTGGA GTATTTTTAC CGTATGTTTC    6240

CTATGCTACC TGTGTTATCT GCAGTGTTGT GGACGCTGGT GTCCCACGCC GGGAAGGGGA    6300

CGACGAGGCG TGAGGGCTA TCGACGCCTA CCGACTTACG ATAGTTACCC CGGTGTTAGA    6360

AAGATGAAGA GGTGAGAACA CGTATAAAAT AAAAAAATAA TATGTTAAAA AATGCAGTGT    6420

GTGAAGTGTG AATAGTGTGA TTAAAATATG CGGATTGAAT GGGTGTGGTG GTTATTCGGA    6480

TACTTTGTGT CATCCGTTGG GAGCGAACGG TCATTATCCT ATCGTTACCA CTTGGAATCT    6540

AATTCATCTA CCAACGTGGT TTGCAACGGA AACATTTCCG TGTTTGTAAA CGGCACCCTA    6600

GGTGTGCGGT ATAACATTAC GGTAGGAATC AGTTCGTCTT TATTAATAGG ACACCTTACT    6660

ATACAAGTAT TGGAATCATG GTTCACACCC TGGGTCCAAA ATAAAAGTTA CAACAAACAA    6720

CCCCTAGGTG ACACTGAAAC GCTTTATAAT ATAGATAGCG AAAACATTCA TCGCGTATCT    6780

CAATATTTTC ACACAAGATG GATAAAATCT CTGCAAGAGA ATCACACTTG CGACCTCACA    6840

AACAGTACAC CTACCTATAC ATATCAAGTA AACGTGAACA ACACGAATTA CCTAACACTA    6900

ACATCCTCGG GATGGCAAGA CCGTCTAAAT TACACCGTCA TAAATAGTAC ACACTTTAAC    6960

CTCACAGAAT CGAACATAAC CAGCATTCAA AAATATCTCA ACACTACCTG CATAGAAAGA    7020

CTCCGTAACT ACACCTTGGA GTCCGTATAC ACCACAACTG TGCCTCAAAA CATAACAACA    7080

TCTCAACACG CAACAACCAC TATGCACACA ATACCTCCAA ATACAATAAC AATTCAAAAT    7140

ACAACTCAAA GCCATACTGT ACAGACGCCG TCTTTTAACG ACACACATAA CGTGACGAAA    7200

CACACGTTAA ACATAAGCTA CGTTTTATCA CAAAAACGA ATAACACAAC ATCACCGTGG    7260

ATATATGCCA TACCTATGGG CGCTACAGCC ACAATAGGCG CCGGTTTATA TATCGGGAAA    7320
```

```
CACTTTACGC CGGTTAAGTT CGTATACGAG GTATGGCGCG GTCAGTAAAG ACGATTCGGA      7380

TTCAACACAT ATACTCCCCA CGATCCTCGA ACACCTTACA GCATATGAGC AAAAAACAAG      7440

AAAGTATAGC CACAATCACA TTTGGGCGAA TAACATGCTG TCATCCACTA GCGTCTATTA      7500

ATCTAATGTT TAACGGGAGC TGTACTGTCA CCGTTAAAAT ATCCATGGGA ATCAACGGGT      7560

CAACCAACGT CCATCAGCTT GTGATTGTGC TCCATCTGGG TAACCGCTGT CAGCCTTGGC      7620

GACAGGTGTA ATCACAGCTG TCACATAACT CACGAAGCCT CCAATCACAG CAGCACACAT      7680

AGTCCTAACG CCATTGGCGT GTATAAAAGT TCGGAAAACT TGACGGTTGT ACGGCACGAC      7740

AAATCGATGT AGTGGTATGT TTTTCCAGCA GAGACCGTGT GCGGTCTCTT AGGTTCGCTA      7800

TACTGTGGCT GGAAACTGGT TACCTGTGAA GATGGCTAAC TATCCTGTTC TGTCCTGGAA      7860

AAACTTTTGG CGTCGTAGGT GGACTTTGCA GTATGCGGGT TAGTGAAGTT ATGTCATTTA      7920

TTTACGTTTA CGATCTCGTA TTACAAACCG CGGAGAGGAT GATACCGTTC GGCCCCATGA      7980

GTTATTTTTA TTCTTCCGGT AGGAGGCATG AAGCCTCTGA TAATGCTCAT CTGCTTTGCT      8040

GTGATATTAT TGCAGCTTGG AGTGACTAAA GTGTGTCAGC ATAATGAAGT GCAACTGGGC      8100

AATGAGTGCT GCCCTCCGTG TGGTTCGGGA CAAAGAGTTA CTAAAGTATG CACGGATTAT      8160

ACCAGTGTAA CGTGTACCCC TTGCCCCAAC GGCACGTATG TATCGGGACT TTACAACTGT      8220

ACCGATTGCA CTCAATGTAA CGTCACTCAG GTCATGATTC GTAACTGCAC TTCCACCAAT      8280

AATACCGTAT GCGCACCTAA GAACCATACG TACTTTTCCA CTCCAGGCGT CCAACATCAC      8340

AAACAACGAC AGCAAAATCA TACCGCACAT ATAACCGTCA AACAAGGAAA AAGCGGTCGT      8400

CATACTCTAG CCTGGTTGTC TCTCTTTATC TTTCTTGTGG GTATCATACT TTTAATTCTC      8460

TATCTTATAG CCGCCTATCG GAGTGAGAGA TGCCAACAGT GTTGCTCAAT CGGCAAAATT      8520

TTCTACCGCA CCCTGTAAGC TTCCTGTTGT TGTTTTTACA TCACGGTACG ATGAAGTCAC      8580

ACAGATAATT ACAGATGAGC TGTTCATATT TTTTATTATT TTTTCCAATT CCTGCACTAA      8640

AAAAAGAAGC ACTTTACGGA ACCGTGTCTG AGTATCTGTG GGGAATTTAG GTACTTTTTG      8700

CCGACGTCAG GAAAAATAAG TGTCGCCTAC ATAAGAGCCC GGTGCTATCG TGCTGTCACT      8760

CTTTCTTGTT GCCTTCGATG TACGGCGTCC TGGCTCATTA CTACTCCTTC ATCAGTAGCC      8820

CCAGCGTTAT GGTTAATTTT AAGCATCATA ACGCCGTGCA GCTGTTATGT GCACGGACCC      8880

GAGACGCACT GCCGGATGGG AACGTTTAAC CCATCATGCG TCGTATCACG CGAACTACGG      8940

GGCATACGCC GTGTTGATGG CTACATCGCA AAGAAAGTCC CTAGTGTTAC ATCGATACAG      9000

TGCCGTGACA GCCGTGGCCC TGCAGCTCAT GCCTGTTGAG ATCGTCCGCA AGCTAGATCA      9060

GTCGGACTGG GTGCGGGGTG CCTGGATCGT GTCAGAGACT TTTCCAACTA GCGACCCCAA      9120

AGGAGTTTGG AGCGACGATG ACTCCTCGAT GGGTGGAAGT GATGATTGAT GATGAGAACC      9180

TGACAAGAAA GACGAGAGAG AAATTTAGAG CTGTCATTGT AGAATTAGTC TAGATTCCTG      9240

ATAATAAACA GTATCGATTT TGAAACCTAA TTGACGTGTG ATCGATTTTT AAACCTCTGT      9300

GTTGTGTGAT TGATTGGTAT GTGGGGGGAT CCGATTTCAA AGGGGGGTAC TTATCGGGAA      9360

TTGATGTGTC ATGGACGCAG TTTTGAGCGA TTTTCCGGGA ATACCGGATA TTACGAATTA      9420

CTGGTAGTGA CGTAGATAAT AAAATTATAA TGCGATTAAT TTTTGGTGCG TTGATTATTT      9480

TTTTAGCATA TGTGTATCAT TATGAGGTGA ATGGAACAGA ATTACGCTGC AGATGTCTTC      9540

ATAGAAAATG GCCGCCTAAT AAAATTATAT TGGGTAATTA TTGGCTTCAT CGCGATCCCA      9600

GAGGGCCCGG ATGCGATAAA AATGAACATT TATTGTATCC AGACGGAAGG AAACCGCCTG      9660
```

```
GACCTGGAGT ATGTTTATCG CCCGATCACC TCTTCTCAAA ATGGTTAGAC AAACACAACG      9720

ATAATAGGTG GTATAATGTT AACATAACGA AATCACCAGG ACCGAGACGA ATAAATATAA      9780

CCTTGATAGG TGTTAGAGGA TAATATTTAA TGTATGTTTT CAAACAGACA AGTTCGTTAA      9840

AACAAAATAT TACAGTATGT GTTAATATG GTGCTAACAT GGTTGCACCA TCCGGTTTCA       9900

AACTCGCATA TCAATCTGTT ATCGGTACGA CACCTGTCAT TAATCGCATA TATGTTACTT      9960

ACCATATGTC CCCTAGCCGT CCATGTTTTA GAACTAGAAG ATTACGACAG GCGCTGCCGT     10020

TGCAACAACC AAATTCTGTT GAATACCCTG CCGGTCGGAA CCGAATTGCT TAAGCCAATC     10080

GCAGCGAGCG AAAGCTGCAA TCGTCAGGAA GTGCTGGCTA TTTTAAAGGA CAAGGGAACC     10140

AAGTGTCTCA ATCCTAACGC GCAAGCCGTG CGTCGTCACA TCAACCGGCT ATTTTTTCGG     10200

TTAATCTTAG ACGAGGAACA ACGCATTTAC GACGTAGTGT CTACCAATAT TGAGTTCGGT     10260

GCCTGGCCAG TCCCTACGGC CTACAAAGCC TTTCTTTGGA AATACGCCAA GAGACTGAAC     10320

TACCACCACT TCAGACTGCG CTGGTGATCA TGTCCCTATT TTACCGTGCG GTAGCTCTGG     10380

GCACGCTAAG CGCTTTGGTG TGGTACAGCA CTAGCATCCT CGCAGAGATT AACGAAAATT     10440

CCTGCTCCTC ATCTTCTGCG GATCACGAAG ACTGCGAGGA ACCGGACGAG ATCGTTCGCG     10500

AAGAGCAAGA CTATCGGGCT CTGCTGGCCT TTTCCCTAGT GATTTGCGGT ACGCTCCTCG     10560

TCACTTGTGT GATCTGAGAC GTCATGCTGG TAGCGTTTAT GAGTCGGGCG GTGGCCGACA     10620

CGCCGCATTT CCTAACCCGC GCAGCATGTT GCGCTTGCTG TTCACGCTCG TCCTGCTGGC     10680

CCTCCACGGG CAGTCTGTCG GCGCTAGCCG CGACTATGTG CATGTTCGGC TACTGAGCTA     10740

CCGAGGCGAC CCCCTGGTCT TCAAGCACAC TTTCTCGGGT GTGCGTCGAC CCTTCACCGA     10800

GCTAGGCTGG GCTGCGTGTC GCGACTGGGA CAGTATGCAT TGCACACCCT TCTGGTCTAC     10860

CGATCTGGAG CAGATGACCG ACTCGGTGCG GCGTTACAGC ACGGTGAGCC CCGGCAAGGA     10920

AGTGACGCTT CAGCTTCACG GGAACCAAAC CGTACAGCCG TCGTTTCTAA GCTTTACGTG     10980

CCGCCTGCAG CTAGAACCCG TGGTGGAAAA TGTTGGCCTC TACGTGGCCT ACGTGGTCAA     11040

CGACGGCGAA CGCCCACAAC AGTTTTTTAC ACCGCAGGTA GACGTGGTAC GCTTTGCTCT     11100

ATATCTAGAA ACACTCTCCC GGATCGTGGA ACCGTTAGAA TCAGGTCGCC TGGCAGTGGA     11160

ATTTGATACG CCTGACCTAG CTCTGGCGCC CGATTTAGTA AGCAGCCTCT TCGTGGCCGG     11220

ACACGGCGAG ACCGACTTTT ACATGAACTG GACGCTGCGT CGCAGTCAGA CCCACTACCT     11280

GGAGGAGATG GCCTTACAGG TGGAGATTCT AAAACCCCGC GGCGTACGTC ACCGCGCTAT     11340

TATCCACCAT CCGAAGCTAC AGCCGGGCGT TGGCCTGTGG ATAGATTTCT GCGTGTACCG     11400

CTACAACGCG CGCCTGACCC GCGGCTACGT ACGATACACC CTGTCACCGA AAGCGCGCTT     11460

GCCCGCAAAA GCAGAGGGTT GGCTGGTGTC ACTAGACAGA TTCATCGTGC AGTACCTCAA     11520

CACATTGCTG ATTACAATGA TGGCGGCGAT ATGGGCTCGC GTTTTGATAA CCTACCTGGT     11580

GTCGCGGCGT CGGTAGAGGC TTGCGGAAAC CACGTCCTCG TCACACGTCG TTCGCGGACA     11640

TAGCAAGAAA TCCACGTCGC CACATCTCGA GAATGCCGGC CTTGCGGGGT CCCCTTCGCG     11700

CAACATTCCT GGCCCTGGTC GCGTTCGGGT TGCTGCTTCA GATAGACCTC AGCGACGCTA     11760

CGAATGTGAC CAGCAGCACA AAAGTCCCTA CTAGCACCAG CAACAGAAAT AACGTCGACA     11820

ACGCCACGAG TAGCGGACCC ACAACCGGGA TCAACATGAC CACCACCCAC GAGTCTTCCG     11880

TTCACAACGT GCGCAATAAC GAGATCATGA AAGTGCTGGC TATCCTCTTC TACATCGTGA     11940

CAGGCACCTC CATTTTCAGC TTCATAGCGG TACTGATCGC GGTAGTTTAC TCCTCGTGTT     12000

GCAAGCACCC GGGCCGCTTT CGTTTCGCCG ACGAAGAGGC CGTCAACCTG TTGGACGACA     12060
```

```
CGGACGACAG TGGCGGCAGC AGCCCGTTTG GCAGCGGTTC CCGACGAGGT TCTCAGATCC    12120

CCGCCGGATT TTGTTCCTCG AGCCCTTATC AGCGGTTGGA AACTCGGGAC TGGGACGAGG    12180

AGGAGGAGGC GTCCGCGGCC CGCGAGCGCA TGAAACATGA TCCTGAGAAC GTCATCTATT    12240

TCAGAAAGGA TGGCAACTTG GACACGTCGT TCGTGAATCC CAATTATGGG AGAGGCTCGC    12300

CTTTGACCAT CGAATCTCAC CTCTCGGACA ATGAGGAGGA CCCCATCAGG TACTACGTTT    12360

CGGTGTACGA TGAACTGACC GCCTCGGAAA TGGAAGAACC TTCGAACAGC ACCAGCTGGC    12420

AGATTCCCAA ACTAATGAAA GTTGCCATGC AACCCGTCTC GCTCAGAGAT CCCGAGTACG    12480

ACTAGGCTTT TTTTTTTGTC TTTCGGTTCC AACTCTTTCC CCGCCCCATC ACCTCGCCTG    12540

TACTATGTGT ATGATGTCTC ATAATAAAGC TTTCTTTCTC AGTCTGCAAC ATGCAGCTGT    12600

GTCGGGTGTG GCTGTCTGTT TGTCTGTGCG CCGTGGTGCT GGGTCAGTGC AGCGGGAAA    12660

CCGCGGAAAA AAACGATTAT TACCGAGTAC CGCATTACTG GGACGCGTGC TCTCGCGCGC    12720

TGCCCGACCA AACCCGTTAC AAGTATGTGG AACAGCTCGT GGACCTCACG TTGAACTACC    12780

ACTACGATGC GAGCCACGGC TTGGACAACT TTGACGTGCT CAAGAGGTGA GGGTACGCGC    12840

TAAAGGTGCA TGACAACGGG AAGGTAAGGG CGAACGGGTA ACGGCTAAGT AACCGCATGG    12900

GGTATGAAAT GACGTTTGGA ACCTGTGCTT GCAGAATCAA CGTGACCGAG GTGTCGTTGC    12960

TCATCAGCGA CTTTAGACGT CAGAACCGTC GCGGCGGCAC CAACAAAAGG ACCACGTTCA    13020

ACGCCGCCGG TTCGCTGGCG CCACACGCCC GGAGCCTCGA GTTCAGCGTG CGGCTCTTTG    13080

CCAACTAGCC TGCGTCACGG GAAATAATAT GCTGCGGCTT CTGCTTCGTC ACCACTTTCA    13140

CTGCCTGCTT CTGTGCGCGG TTTGGGCAAC GCCCTGTCTG GCGTCTCCGT GGTCGACGCT    13200

AACGGCAAAC CAGAATCCGT CCCCGCCATG GTCTAAACTG ACGTATTCCA AACCGCATGA    13260

CGCGGCGACG TTTTACTGTC CTTTTCTCTA TCCCTCGCCC CCACGGTCCC CCTTGCAATT    13320

CTCGGGGTTC CAGCAGGTAT CAACGGGTCC CGAGTGTCGC AACGAGACCC TGTATCTGCT    13380

GTACAACCGG GAAGGCCAGA CCTTGGTGGA GAGAAGCTCC ACCTGGGTGA AAAAGGTGAT    13440

CTGGTATCTG AGCGGTCGCA ACCAGACCAT CCTCCAACGG ATGCCCCAAA CGGCTTCGAA    13500

ACCGAGCGAC GGAAACGTGC AGATCAGCGT GGAAGACGCC AAGATTTTTG GAGCGCACAT    13560

GGTGCCCAAG CAGACCAAGC TGCTACGCTT CGTCGTCAAC GATGGCACGC GTTATCAGAT    13620

GTGTGTGATG AAGCTGGAGA GCTGGGCCCA CGTCTTCCGG GACTACGCG TGTCTTTTCA    13680

GGTGCGATTG ACGTTCACCG AGGCCAATAA CCAGACTTAC ACCTTCTGTA CCCATCCCAA    13740

TCTCATCATT TGAGCCCGTC GCGCGCGCAG GGAATTTTGA AAACCGCGCG TCATGAGTCC    13800

CAAAGACCTG ACGCCGTTCT TGACGACGTT GTGGCTGCTA TTGGGTCACA GCCGCGTGCC    13860

GCGGGTGCGC GCAGAAGAAT GTTGCGAATT CATAAACGTC AACCACCCGC CGGAACGCTG    13920

TTACGATTTC AAAATGTGCA ATCGCTTCAC CGTCGCGTAC GTATTTTCAT GATTGTCTGC    13980

GTTCTGTGGT GCGTCTGGAT TTGTCTCTCG ACGTTTCTGA TAGCCATGTT CCATCGACGA    14040

TCCTCGGGAA TGCAGAGTA GATTTTCATG AATCCACAGG CTGCGGTGTC CGGACGGCGA    14100

AGTCTGCTAC AGTCCCGAGA AAACGGCTGA GATTCGCGGG ATCGTCACCA CCATGACCCA    14160

TTCATTGACA CGCCAGGTCG TACACAACAA ACTGACGAGC TGCAACTACA ATCCGTAAGT    14220

CTCTTCCTCG AGGGCCTTAC AGCCTATGGG AGAGTAAGAC AGAGAGGGAC AAAACATCAT    14280

TAAAAAAAAA AGTCTAATTT CACGTTTTGT ACCCCCCTTC CCCTCCGTGT TGTAGCCCAT    14340

CGGCCGCGGC GATCTCCTAG TAACACTCGT CCGACACTTC CACCATCTCC AGCTCGGCCG    14400
```

```
GCGGTTCGGC ATCCTCTACC AGCGGCGTCG TCTCATCTTT GCCGCAGCAG CGGACGCACA    14460

CCTTCTCCAG GCAGAACGCC ACCAGCTGCC GCCGAACGTA CCACAGGTAC ACGTGCAGAC    14520

CTGCGAACAG GACTACGGAG GTCATGACCA CCACGACGCA CACGGGAATC CAGGGATCGA    14580

GATTGTTGCT GGAACTCATG GCTATCGCCA CCGACGTGCC CGCGTCTGTC TCACCGCCGC    14640

TCGCCCGATG TCGCGCGGCT TGTTATACGC TAGCCCGTCG CCGCCTCGGG GCACGGTGCC    14700

CTCCTACCCA CGTAACTTCC TCCGTGACTT AAAGTCGCGT GTGGTAGATC TCCTGCTCCG    14760

TGGACGAACC GTCCGGCAGG ATAGCGGTTA AGGATTCGGT GCTAAGGCCG TGTCGCCAAC    14820

GTCGAATGCT ACGTTGCAAC AGCTTCGACG GACGGCCATC CCCTCTCTCA TCGCAATAAT    14880

AAAACACCAG CAGCGCGCAC GACGCGATCA CGGTGACACC CATGATTAGA CCCACGCAGA    14940

TAGCCAGCCC CGCTAGCGTA TCTAGCGCCA TCCCGTTCGC TCCCGTTGTC TCCTGAGCGA    15000

AGCAACTTCT CGGTCCCCGT TTTCAACAGT TTTTGTTTCC TTCTCCGCGA CTAGATGTTA    15060

ACGCCCGCGG TCTTTCCGGC CGTGCTCTAC CTCCTGGCGC TTGTCGTCTG GGTTGAGATG    15120

TTCTGCCTCG TCGCCGTAGC CGTCGTCGAG CGCGAGATCG CCTGGGCGCT GCTGCTGCGG    15180

ATGCTGGTCG TTGGCCTGAT GGTGGAAGTC GGCGCCGCCG CCGCTTGGAC CTTCGTGCGT    15240

TGTCTTGCCT ATCAGCGCTC CTTCCCCGTG CTTACGGCCT TCCCCTGAAA CCCACGTTAA    15300

CCGACCGTCC CAAAAACGCC GGTGTTAACA CAGGAAAAAA AGAAACCACG CAGGAACCGC    15360

GCAGGAACCA CGCGGAACAT GGGACACTAT CTGGAAATCC TGTTCAACGT CATCGTCTTC    15420

ACTCTGCTGC TCGGCGTCAT GGTCAGTATC GTCGCTTGGT ACTTCACGTG AACCACCGTC    15480

GTCCCGGTTT AAAAACCATC ATCGACGGCC GTTATAAAGC CACCCGGACA CGCGCCGCGG    15540

CACTTGCCTA CGGCGCTGCT TCAGGGAAAC TCCTCTTCCT TCTGCTCTTC CTCCTTCACC    15600

GCAGGGATCG TTTCCCTCGA CCAGGGACTC GCCGAAGCAA CCGCCGGAGC AACCTGGAGG    15660

AGTCGCGGCA TGACGGCGCC CAAGTGTGTC ACCACCAGTA CTTATCTGGT CAAGACCAAG    15720

GAACAGCCCT GGTGGCCCGA CAACGCCATC AGGAGATGGT GGATCAGTGT TGCTATCGTC    15780

ATCTTCATCG GAGTCTGTCT GGTGGCCCTG ATGTACTTTA CGCAGCAGCA GGCACGCAGC    15840

GGGAGCAGCA GCGGCTAGAC AAGTCTCTGG CGGCTACAGC TCCAAGCGCC GTAGCCGGGC    15900

CGCCTGCCGA TCGCGACGTC GTGGACCATC GAACAGAGAC TCACGCGTAC GAGACCCCGA    15960

GGTACGCCAC GCGGTGCCTA ACGCGGTATA CCACACCCGT ACGGTCTGCA GTGCGGCGTA    16020

CAACGTGTGG AAAACGCGTT GCGTCGCAGA GTCCGCCACG TTCCTGTCTT GTCGCTCCCC    16080

AATCGTCTCC CGCACACCCC CCGCGACACC CAGAGGGCGG GTGAGCCAAG TATTCTTAAG    16140

GCCGTTCTTT GTTCCATAGC CCATAAATTG TTGATTCCGG AGCTCGTTGG CGCGGAAATA    16200

GCCGGATAAG GGGAGCAACA ACCGTTGGCG AAAGCCGTCC CGCTCATTCA GTCCGGGTTT    16260

CGCGTCCAGT CGGACGTGTG ACCGTTGGGC AACGGAACGG CGTTTCACTG CCAAAATCGT    16320

ATCGGGTAGT GTACGAGACG TCGGCGGTGC AGAATGCGAC TCGCGGCGTA GCTCGCCGTC    16380

GCTATGCGGC TCGTCGCCGT GTGGCGCGGC CTGGCCGGCT GTCTGCGTCC AGATCTGTTG    16440

GCCTTTTGGT TCCTCTGGCT GCTGCTGCGT GTGTGCTTTG GTAGACGCGG TGGCAGTTTG    16500

CGGTCTGCGG TAAGTGAGGA TGTCGCCGAG CAAACGCACT TGCGGCGCGT GGGCGGCACG    16560

CGTGTCATTG TAGGTTCGTT GCCAGATGGC AAGTGCTGTC AACAGCAGGC GTTGTGGGCG    16620

GTCGGTGTAT TTTTGTGGGT TGCGGTGAGA GTCGGCACTC GGTGTTTTGT GAGTCATCTC    16680

AACTATCTGT GTTGCTTTGA GCAGCGTCCA GAACAGCGAC GCGACTTTGG GGATGGCCTC    16740

GTGCTCACCT CCGCGGAGAG CGCCGCCGGA CCTGCTCGTC AGCAGCGAGC TACGCAGACG    16800
```

-continued

```
GAATATCTGG AGGAGAGTTA CGTGTGTCAC AGGAGAGCGC GGGTCTCCGG CGGTAACGAC    16860

GGCGGTGTCG TCGACACGTG TGCGGCCTGT TGTGCTCTGC GGAAAAGTGC CGGTCTCGGA    16920

GACCGTGGAC GAAAAAGAGA ACGCAGCAGC TACCGCTGGC GGCGGCGGCG TTAATGCAGC    16980

CGTTGATGTT CGACGTTGTG AGCACTCGGA ACAGCGGTG AGGCAGAAGG TCGATTCTCC    17040

AGGGAACGAC AGTCGATGCG TGGTAGCCGC AGCAGGTGAG GTTGGGCGG ACAACGTGTT    17100

GCGGATTGTG GCGAGAACGT CGTCCTCCCC TTCTTCACCG CCCCACCCAC CCTCGGTTGG    17160

TGTTTCTTTT TTCTTGTGTC CTGCAGATAG TTCCACGGAC AGCGACGGCA AGTCCATAAT    17220

CAGCGGTGTG CAAGTGGTGG AACACGACGA AGATATCATC GCGCCGCAGA GTTTGTGGTG    17280

CACGGCGTTC AAGGAAGCCC TCTGGGATGT GGCTCTGTTG GAAGTGCCGC GTTGGGCGTG    17340

GCAGGGCTGG AAGAGGTGGC GCAACAGCGA GGCCGGGCGT CGATGGAGTG CTGGGTCTGC    17400

GTCGGCTTCC AGCTTGTCTG ACTTGGCGGG CGAGGCCGTT GGAGAATTGG TGGGATCGGT    17460

CGTCGCGTAC GTGATCCTTG AACGTCTGTG GTTGGCAGCC AGAGGTTGGG TGTGCGAAAC    17520

AGGTGTGGAA GCCGAGGAGG CCATGTCGCG GCGGCGACAG CGCATGCTGT GGCGTATTGT    17580

TCTCTCGTGG AGGCGACGGC GAATGCAGCA GACGGTGTTC GATGGAGATG GCGTGCGGGG    17640

AAGAAAGCGC CGTGTTGTGA GCAGACGACG TAGGATGCGG GACGTCGGAG CACATGGGCC    17700

ATGTGTGGTG GCAGATGGCG GTGTCCGCTG GTGTCTGCTG CGGCAGTGCA TAGACGAAGC    17760

AACATGTCGC TGTGAAGAGA TAGAGTGTGA GCATAGCTGC ATGCAGCGTT GCGTGTATAA    17820

GCGGGGGGGA TTAAGACGTT AATAAAGAAT AGCGGCGGTT CTGATAGGGC GACCGCTGAA    17880

GTGAGCTGCG TGTGCGTGTG GTTTGTGGAG TCCCCGCCGC CCCCGGTCCC GTGTCCGCCG    17940

GCAAAGCCCC CCGGNTCCGC ACACTCCTGG CCGCGCAACC CTCGTCGCTG CAAAAGCCCC    18000

CCGTCCCCGC ACACCCCCGC GACCGCCGGT CCCGCGAGTC CCCGTCCCCG CCGCAAAAGG    18060

CCCCCGTCCT CGCCGCAAAC ACCCCCGTCA CCCCCGTCCC TCAGNCCGGG TCCGCGAGTC    18120

CCCGTTCCCA GCGTAATCCC CGTACCCGCA ACGNCCCGGN CCCACCGTCG TCCCGCACAC    18180

CCCCCGTCCC CCAGCCCGGT GCCCAGCGTG CGAAAAAAGC TCCGTCCCTC ACACCCGCAG    18240

AAAGATCCCT CAGCGCGGTG AAACCCCGTC CCCAGCGCCG TGCCGCTGAC AAAGACCATG    18300

GGACGACACG CACAGGCA                                                  18318
```

(2) INFORMATION FOR SEQ ID NO: 7:

(i) SEQUENCE CHARACTERISTICS:
        (A) LENGTH: 257 amino acids
        (B) TYPE: amino acid
        (D) TOPOLOGY: linear (ii) MOLECULE TYPE: protein (vii) IMMEDIATE SOURCE:
        (B) CLONE: tol.01

(ix) FEATURE:
        (A) NAME/KEY: Protein
        (B) LOCATION: 1..257
        (D) OTHER INFORMATION: /label= UL133

(xi) SEQUENCE DESCRIPTION: SEQ ID NO: 7:

```
Met Gly Cys Asp Val His Asp Pro Ser Trp Gln Cys Gln Trp Gly Val
1               5                   10                  15

Pro Thr Ile Ile Val Ala Trp Ile Thr Cys Ala Ala Leu Gly Ile Trp
            20                  25                  30
```

```
Cys Leu Ala Gly Ser Ser Ala Asp Val Ser Ser Gly Pro Gly Ile Ala
         35                  40                  45

Ala Val Val Gly Cys Ser Val Phe Met Ile Phe Leu Cys Ala Tyr Leu
 50                  55                  60

Ile Arg Tyr Arg Glu Phe Phe Lys Asp Ser Val Ile Asp Leu Leu Thr
 65                  70                  75                  80

Cys Arg Trp Val Arg Tyr Cys Ser Cys Ser Cys Lys Cys Ser Cys Lys
                 85                  90                  95

Cys Ile Ser Gly Pro Cys Ser Arg Cys Cys Ser Ala Cys Tyr Lys Glu
                100                 105                 110

Thr Met Ile Tyr Asp Met Val Gln Tyr Gly His Arg Arg Pro Gly
         115                 120                 125

His Gly Asp Asp Pro Asp Arg Val Ile Cys Glu Ile Val Glu Ser Pro
    130                 135                 140

Pro Val Ser Ala Pro Thr Val Ser Val Pro Pro Ser Glu Glu Ser
145                 150                 155                 160

His Gln Pro Val Ile Pro Pro Gln Pro Ala Pro Thr Ser Glu Pro
                165                 170                 175

Lys Pro Lys Lys Gly Arg Ala Lys Asp Lys Pro Lys Gly Arg Pro Lys
                180                 185                 190

Asp Lys Pro Pro Cys Glu Pro Thr Val Ser Ser Gln Pro Pro Ser Gln
        195                 200                 205

Pro Thr Ala Met Pro Gly Gly Pro Pro Asp Ala Pro Pro Ala Met
    210                 215                 220

Pro Gln Met Pro Pro Gly Val Ala Glu Ala Val Gln Ala Ala Val Gln
225                 230                 235                 240

Ala Ala Val Ala Ala Leu Gln Gln Gln Gln His Gln Thr Gly
                245                 250                 255

Thr
```

(2) INFORMATION FOR SEQ ID NO: 8:

(i) SEQUENCE CHARACTERISTICS:
        (A) LENGTH: 175 amino acids
        (B) TYPE: amino acid
        (D) TOPOLOGY: linear (ii) MOLECULE TYPE: protein (vii) IMMEDIATE SOURCE:
        (B) CLONE: tol.02

(ix) FEATURE:
        (A) NAME/KEY: Protein
        (B) LOCATION: 1..175
        (D) OTHER INFORMATION: /label= UL134

(xi) SEQUENCE DESCRIPTION: SEQ ID NO: 8:

```
Met Ala Arg Thr Arg Glu Ala Ser Pro Val Pro Pro Arg Ser Pro Met
 1               5                  10                  15

Pro Ser His Ile His Thr Met Ile Phe Ser Pro Ala Trp Asn Leu Lys
                20                  25                  30

Leu Arg Val Gly Lys Gly Arg Cys Thr Asp Ile Tyr Ala Leu Asp Phe
         35                  40                  45

Trp Lys Arg His Phe Leu Ala Arg Asn Val Phe Ile Val Gln Thr Leu
 50                  55                  60

Arg Lys Glu Met Cys Ala Lys Ser Glu Asn Ser Leu Ser His Arg Gly
 65                  70                  75                  80
```

-continued

```
Arg Val Thr Phe Arg Ser Asp Ala Ala Val Val Glu Pro Arg
             85                  90                  95

Pro Arg Pro Pro Ala Arg Gln Leu Val Pro Pro Arg Pro Arg Arg Val
            100                 105                 110

Ala Ser Ala Ala Trp Arg Gly Glu Ala Arg Arg Ala Asp Arg Arg Ala
            115                 120                 125

Leu Pro Ser Ala Ala Thr Val Val Val Asn Ser Pro Ser Val Arg Thr
130                 135                 140

Glu Val Cys Leu Ser Val Tyr Pro Ser Val Tyr Leu Ser Pro Tyr Leu
145                 150                 155                 160

Ser Ser Val Trp Val Pro Met Ser Val Leu Ala Ala Val Gly
                165                 170                 175

(2) INFORMATION FOR SEQ ID NO: 9:

(i) SEQUENCE CHARACTERISTICS:
        (A) LENGTH: 328 amino acids
        (B) TYPE: amino acid
        (D) TOPOLOGY: linear (ii) MOLECULE TYPE: protein (vii) IMMEDIATE SOURCE:
        (B) CLONE: tol.03

(ix) FEATURE:
        (A) NAME/KEY: Protein
        (B) LOCATION: 1..328
        (D) OTHER INFORMATION: /label= UL135

(xi) SEQUENCE DESCRIPTION: SEQ ID NO: 9:

Met Ser Val His Arg Pro Phe Pro Thr Arg Ser Leu Arg Phe Gln Ala
1               5                  10                  15

Gly Glu Lys Ile Met Val Trp Ile Trp Leu Gly Ile Gly Leu Leu Gly
            20                  25                  30

Gly Thr Gly Leu Ala Ser Leu Val Leu Ala Ile Ser Leu Phe Thr Gln
            35                  40                  45

Arg Arg Gly Arg Lys Arg Ser Asp Glu Thr Ser Ser Arg Gly Arg Leu
50                  55                  60

Pro Gly Ala Ala Ser Asp Lys Arg Gly Ala Cys Ala Cys Cys Tyr Arg
65                  70                  75                  80

Asn Pro Lys Glu Asp Val Val Glu Pro Leu Asp Leu Glu Leu Gly Leu
            85                  90                  95

Met Arg Val Asp Thr His Pro Pro Thr Pro Gln Val Pro Arg Cys Thr
            100                 105                 110

Ser Leu Tyr Ile Gly Glu Asp Gly Leu Pro Ile Asp Lys Pro Glu Phe
            115                 120                 125

Pro Pro Ala Arg Phe Glu Ile Pro Asp Val Ser Thr Pro Gly Thr Pro
130                 135                 140

Thr Ser Ile Gly Arg Ser Pro Ser His Cys Ser Ser Ser Ser Ser Leu
145                 150                 155                 160

Ser Ser Ser Thr Ser Val Asp Thr Val Leu Tyr Gln Pro Pro Pro Ser
                165                 170                 175

Trp Lys Pro Pro Pro Pro Gly Arg Lys Lys Arg Pro Pro Thr Pro
            180                 185                 190

Pro Val Arg Ala Pro Thr Thr Arg Leu Ser Ser His Arg Pro Pro Thr
            195                 200                 205

Pro Ile Pro Ala Pro Arg Lys Asn Leu Ser Thr Pro Pro Thr Lys Lys
            210                 215                 220
```

```
Thr Pro Pro Pro Thr Lys Pro Lys Pro Val Gly Trp Thr Pro Pro Val
225                 230                 235                 240

Thr Pro Arg Pro Phe Pro Lys Thr Pro Thr Pro Gln Lys Pro Pro Arg
            245                 250                 255

Asn Pro Arg Leu Pro Arg Thr Val Gly Leu Glu Asn Leu Ser Lys Val
            260                 265                 270

Gly Leu Ser Cys Pro Cys Pro Arg Pro Arg Thr Pro Thr Glu Pro Thr
            275                 280                 285

Thr Leu Pro Ile Val Ser Val Ser Glu Leu Ala Pro Pro Pro Arg Trp
            290                 295                 300

Ser Asp Ile Glu Glu Leu Leu Glu Gln Ala Val Gln Ser Val Met Lys
305                 310                 315                 320

Asp Ala Glu Ser Met Gln Met Thr
                325
```

(2) INFORMATION FOR SEQ ID NO: 10:

(i) SEQUENCE CHARACTERISTICS:
      (A) LENGTH: 240 amino acids
      (B) TYPE: amino acid
      (D) TOPOLOGY: linear (ii) MOLECULE TYPE: protein (vii) IMMEDIATE SOURCE:
      (B) CLONE: tol.04

(ix) FEATURE:
      (A) NAME/KEY: Protein
      (B) LOCATION: 1..240
      (D) OTHER INFORMATION: /label= UL136

(xi) SEQUENCE DESCRIPTION: SEQ ID NO: 10:

```
Met Ser Val Lys Gly Val Glu Met Pro Glu Met Thr Trp Asp Leu Asp
1               5                   10                  15

Val Arg Asn Lys Trp Arg Arg Lys Ala Leu Ser Arg Ile His Arg
            20                  25                  30

Phe Trp Glu Cys Arg Leu Arg Val Trp Trp Leu Ser Asp Ala Gly Val
            35                  40                  45

Arg Glu Thr Asp Pro Pro Arg Pro Arg Arg Pro Thr Trp Met Thr
50                  55                  60

Ala Val Phe His Val Ile Cys Ala Val Leu Leu Thr Leu Met Ile Met
65                  70                  75                  80

Ala Ile Gly Ala Leu Ile Ala Tyr Leu Arg Tyr Tyr His Gln Asp Ser
            85                  90                  95

Trp Arg Asp Met Leu His Asp Leu Phe Cys Gly Cys His Tyr Pro Glu
            100                 105                 110

Lys Cys Arg Arg His His Glu Arg Gln Arg Arg Arg Gln Ala Met
            115                 120                 125

Asp Val Pro Asp Pro Glu Leu Gly Asp Pro Ala Arg Arg Pro Leu Asn
130                 135                 140

Gly Ala Met Tyr Tyr Gly Ser Gly Cys Arg Phe Asp Thr Val Glu Met
145                 150                 155                 160

Val Asp Glu Thr Arg Pro Ala Pro Pro Ala Leu Ser Ser Pro Glu Thr
            165                 170                 175

Gly Asp Asp Ser Asn Asp Asp Ala Val Ala Gly Gly Ala Gly Gly
            180                 185                 190

Val Thr Ser Pro Ala Thr Arg Thr Thr Ser Pro Asn Ala Leu Leu Pro
```

```
                    195                 200                 205
Glu Trp Met Asp Ala Val His Val Ala Val Gln Ala Val Gln Ala
    210                 215                 220

Thr Val Gln Val Ser Gly Pro Arg Glu Asn Ala Val Ser Pro Ala Thr
225                 230                 235                 240
```

(2) INFORMATION FOR SEQ ID NO: 11:

(i) SEQUENCE CHARACTERISTICS:
        (A) LENGTH: 96 amino acids
        (B) TYPE: amino acid
        (D) TOPOLOGY: linear (ii) MOLECULE TYPE: protein (vii) IMMEDIATE SOURCE:
        (B) CLONE: tol.05

(ix) FEATURE:
        (A) NAME/KEY: Protein
        (B) LOCATION: 1..96
        (D) OTHER INFORMATION: /label= UL137

(xi) SEQUENCE DESCRIPTION: SEQ ID NO: 11:

```
Met Ala Thr Ile Ser Thr Ser Ile Thr Pro Met Met Gly Asn Pro Thr
1               5                   10                  15

Phe Ser Gly Arg Ser Ser Met Val Thr Val Leu Cys Pro Asp Leu Arg
                20                  25                  30

Pro Ser Leu Ser Leu Leu Tyr Ser Thr Arg Ala Gly Thr Ala Pro Ser
            35                  40                  45

Thr Leu Leu Arg Ser Gly Arg Tyr Gly Val Leu Pro Arg Ala Thr Tyr
        50                  55                  60

Leu His Gly Arg Leu Asn Gly Gly Leu Asp Arg His Met His Arg Ile
65                  70                  75                  80

His Pro Phe Trp Gln Gln Cys Val Arg Arg Arg Thr Ser Arg Gly
                85                  90                  95
```

(2) INFORMATION FOR SEQ ID NO: 12:

(i) SEQUENCE CHARACTERISTICS:
        (A) LENGTH: 169 amino acids
        (B) TYPE: amino acid
        (D) TOPOLOGY: linear (ii) MOLECULE TYPE: protein (vii) IMMEDIATE SOURCE:
        (B) CLONE: tol.06

(ix) FEATURE:
        (A) NAME/KEY: Protein
        (B) LOCATION: 1..169
        (D) OTHER INFORMATION: /label= UL138

(xi) SEQUENCE DESCRIPTION: SEQ ID NO: 12:

```
Met Asp Asp Leu Pro Leu Asn Val Gly Leu Pro Ile Ile Gly Val Met
1               5                   10                  15

Leu Val Leu Ile Val Ala Ile Leu Cys Tyr Leu Ala Tyr His Trp His
                20                  25                  30

Asp Thr Phe Lys Leu Val Arg Met Phe Leu Ser Tyr Arg Trp Leu Ile
            35                  40                  45

Arg Cys Cys Glu Leu Tyr Gly Glu Tyr Glu Arg Phe Ala Asp Leu
        50                  55                  60

Ser Ser Leu Gly Leu Gly Ala Val Arg Arg Glu Ser Asp Arg Arg Tyr
```

```
                65              70              75              80
Arg Phe Ser Glu Arg Pro Asp Glu Ile Leu Val Arg Trp Glu Glu Val
                    85              90              95
Ser Ser Gln Cys Ser Tyr Ala Ser Ser Arg Ile Thr Asp Arg Arg Val
                100             105             110
Gly Ser Ser Ser Ser Ser Val His Val Ala Ser Gln Arg Asn Ser
            115             120             125
Val Pro Pro Asp Met Ala Val Thr Ala Pro Leu Thr Asp Val Asp
    130             135             140
Leu Leu Lys Pro Val Thr Gly Ser Ala Thr Gln Phe Thr Val Ala
145             150             155             160
Met Val His Tyr His Gln Glu Tyr Thr
                165
```

(2) INFORMATION FOR SEQ ID NO: 13:

(i) SEQUENCE CHARACTERISTICS:
        (A) LENGTH: 135 amino acids
        (B) TYPE: amino acid
        (D) TOPOLOGY: linear (ii) MOLECULE TYPE: protein (vii) IMMEDIATE SOURCE:
        (B) CLONE: tol.07

(ix) FEATURE:
        (A) NAME/KEY: Protein
        (B) LOCATION: 1..135
        (D) OTHER INFORMATION: /label= UL139

(xi) SEQUENCE DESCRIPTION: SEQ ID NO: 13:

```
Met Leu Trp Ile Leu Val Leu Phe Ala Leu Ala Ala Ser Ala Ser Glu
1               5               10              15
Thr Thr Thr Gly Thr Ser Ser Asn Ser Ser Gln Ser Thr Ser Ala Thr
            20              25              30
Ala Asn Thr Thr Val Ser Thr Cys Ile Asn Ala Ser Asn Gly Ser Ser
        35              40              45
Trp Thr Val Pro Gln Leu Ala Leu Leu Ala Ala Ser Gly Trp Thr Leu
    50              55              60
Ser Gly Leu Leu Leu Leu Phe Thr Cys Cys Phe Cys Cys Phe Trp Leu
65              70              75              80
Val Arg Lys Ile Cys Ser Cys Cys Gly Asn Ser Ser Glu Ser Glu Ser
                85              90              95
Lys Thr Thr His Ala Tyr Thr Asn Ala Ala Phe Thr Ser Ser Asp Ala
            100             105             110
Thr Leu Pro Met Gly Thr Thr Gly Ser Tyr Thr Pro Pro Gln Asp Gly
        115             120             125
Ser Phe Pro Pro Pro Arg
        130             135
```

(2) INFORMATION FOR SEQ ID NO: 14:

(i) SEQUENCE CHARACTERISTICS:
        (A) LENGTH: 114 amino acids
        (B) TYPE: amino acid
        (D) TOPOLOGY: linear (ii) MOLECULE TYPE: protein (vii) IMMEDIATE SOURCE:
        (B) CLONE: tol.08

```
        (ix) FEATURE:
              (A) NAME/KEY: Protein
              (B) LOCATION: 1..114
              (D) OTHER INFORMATION: /label= UL140

(xi) SEQUENCE DESCRIPTION: SEQ ID NO: 14:

Met Thr Pro Ala Gln Thr Asn Ala Thr Thr Val His Pro His Asp
 1               5                  10                 15

Ala Lys Asn Gly Ser Gly Gly Ser Ala Leu Pro Thr Leu Val Val Phe
                20                  25                  30

Gly Phe Ile Val Thr Leu Leu Phe Leu Phe Met Leu Tyr Phe Trp
            35                  40                  45

Asn Asn Asp Val Phe Arg Lys Leu Leu Arg Ala Leu Gly Ser Ser Ala
 50                      55                  60

Val Ala Thr Ala Ser Thr Arg Gly Lys Thr Arg Ser Ser Thr Val Val
 65                  70                  75                  80

His His Val Val Pro Arg Ala Thr Thr Arg Val Val Leu Thr Ala Cys
                    85                  90                  95

His Arg Thr Phe Phe Tyr His Pro Arg Pro Met Ala Val Leu Thr Thr
                100                 105                 110

Arg His (2) INFORMATION FOR SEQ ID NO: 15:

(i) SEQUENCE CHARACTERISTICS:
              (A) LENGTH: 425 amino acids
              (B) TYPE: amino acid
              (D) TOPOLOGY: linear (ii) MOLECULE TYPE: protein (vii) IMMEDIATE SOURCE:
              (B) CLONE: tol.09

(ix) FEATURE:
              (A) NAME/KEY: Protein
              (B) LOCATION: 1..425
              (D) OTHER INFORMATION: /label= UL141

(xi) SEQUENCE DESCRIPTION: SEQ ID NO: 15:

Met Arg Gln Val Ala Tyr Arg Arg Arg Glu Ser Ser Cys Ala Val
 1               5                  10                 15

Leu Val His His Val Gly Arg Asp Gly Asp Gly Glu Gly Glu Ala Ala
                20                  25                  30

Lys Lys Thr Cys Lys Lys Thr Gly Arg Ser Val Ala Gly Ile Pro Gly
            35                  40                  45

Glu Lys Leu Arg Arg Thr Val Val Thr Thr Thr Pro Ala Arg Arg Leu
 50                  55                  60

Ser Gly Arg His Thr Glu Gln Glu Gln Ala Gly Met Arg Leu Cys Glu
 65                  70                  75                  80

Lys Gly Lys Lys Arg Ile Ile Met Cys Arg Arg Glu Ser Leu Arg Thr
                85                  90                  95

Leu Pro Trp Leu Phe Trp Val Leu Leu Ser Cys Pro Arg Leu Leu Glu
                100                 105                 110

Tyr Ser Ser Ser Ser Phe Pro Phe Ala Thr Ala Asp Ile Ala Glu Lys
            115                 120                 125

Met Trp Ala Glu Asn Tyr Glu Thr Thr Ser Pro Ala Pro Val Leu Val
 130                 135                 140

Ala Glu Gly Glu Gln Val Thr Ile Pro Cys Thr Val Met Thr His Ser
```

-continued

```
145                 150                 155                 160
Trp Pro Met Val Ser Ile Arg Ala Arg Phe Cys Arg Ser His Asp Gly
                165                 170                 175
Ser Asp Glu Leu Ile Leu Asp Ala Val Lys Gly His Arg Leu Met Asn
            180                 185                 190
Gly Leu Gln Tyr Arg Leu Pro Tyr Ala Thr Trp Asn Phe Ser Gln Leu
            195                 200                 205
His Leu Gly Gln Ile Phe Ser Leu Thr Phe Asn Val Ser Met Asp Thr
    210                 215                 220
Ala Gly Met Tyr Glu Cys Val Leu Arg Asn Tyr Ser His Gly Leu Ile
225                 230                 235                 240
Met Gln Arg Phe Val Ile Leu Thr Gln Leu Glu Thr Leu Ser Arg Pro
                245                 250                 255
Asp Glu Pro Cys Cys Thr Pro Ala Leu Gly Arg Tyr Ser Leu Gly Asp
                260                 265                 270
Gln Ile Trp Ser Pro Thr Pro Trp Arg Leu Arg Asn His Asp Cys Gly
            275                 280                 285
Thr Tyr Arg Gly Phe Gln Arg Asn Tyr Phe Tyr Ile Gly Arg Ala Asp
    290                 295                 300
Ala Glu Asp Cys Trp Lys Pro Ala Cys Pro Asp Glu Glu Pro Asp Arg
305                 310                 315                 320
Cys Trp Thr Val Ile Gln Arg Tyr Arg Leu Pro Gly Asp Cys Tyr Arg
                325                 330                 335
Ser Gln Pro His Pro Pro Lys Phe Leu Pro Val Thr Pro Ala Pro Pro
                340                 345                 350
Ala Asp Ile Asp Thr Gly Met Ser Pro Trp Ala Thr Arg Gly Ile Ala
355                 360                 365
Ala Phe Leu Gly Phe Trp Ser Ile Phe Thr Val Cys Phe Leu Cys Tyr
370                 375                 380
Leu Cys Tyr Leu Gln Cys Cys Gly Arg Trp Cys Pro Thr Pro Gly Arg
385                 390                 395                 400
Gly Arg Arg Gly Gly Glu Gly Tyr Arg Arg Leu Pro Thr Tyr Asp Ser
                405                 410                 415
Tyr Pro Gly Val Arg Lys Met Lys Arg
                420                 425

(2) INFORMATION FOR SEQ ID NO: 16:

(i) SEQUENCE CHARACTERISTICS:
        (A) LENGTH: 306 amino acids
        (B) TYPE: amino acid
        (D) TOPOLOGY: linear (ii) MOLECULE TYPE: protein (vii) IMMEDIATE SOURCE:
        (B) CLONE: tol.10

(ix) FEATURE:
        (A) NAME/KEY: Protein
        (B) LOCATION: 1..306
        (D) OTHER INFORMATION: /label= UL142

(xi) SEQUENCE DESCRIPTION: SEQ ID NO: 16:

Met Arg Ile Glu Trp Val Trp Trp Leu Phe Gly Tyr Phe Val Ser Ser
1               5                   10                  15
Val Gly Ser Glu Arg Ser Leu Ser Tyr Arg Tyr His Leu Glu Ser Asn
            20                  25                  30
```

```
Ser Ser Thr Asn Val Val Cys Asn Gly Asn Ile Ser Val Phe Val Asn
        35                  40                  45

Gly Thr Leu Gly Val Arg Tyr Asn Ile Thr Val Gly Ile Ser Ser Ser
    50                  55                  60

Leu Leu Ile Gly His Leu Thr Ile Gln Val Leu Glu Ser Trp Phe Thr
65                  70                  75                  80

Pro Trp Val Gln Asn Lys Ser Tyr Asn Lys Gln Pro Leu Gly Asp Thr
                85                  90                  95

Glu Thr Leu Tyr Asn Ile Asp Ser Glu Asn Ile His Arg Val Ser Gln
            100                 105                 110

Tyr Phe His Thr Arg Trp Ile Lys Ser Leu Gln Glu Asn His Thr Cys
        115                 120                 125

Asp Leu Thr Asn Ser Thr Pro Thr Tyr Thr Tyr Gln Val Asn Val Asn
    130                 135                 140

Asn Thr Asn Tyr Leu Thr Leu Thr Ser Ser Gly Trp Gln Asp Arg Leu
145                 150                 155                 160

Asn Tyr Thr Val Ile Asn Ser Thr His Phe Asn Leu Thr Glu Ser Asn
                165                 170                 175

Ile Thr Ser Ile Gln Lys Tyr Leu Asn Thr Thr Cys Ile Glu Arg Leu
            180                 185                 190

Arg Asn Tyr Thr Leu Glu Ser Val Tyr Thr Thr Thr Val Pro Gln Asn
        195                 200                 205

Ile Thr Thr Ser Gln His Ala Thr Thr Thr Met His Thr Ile Pro Pro
    210                 215                 220

Asn Thr Ile Thr Ile Gln Asn Thr Thr Gln Ser His Thr Val Gln Thr
225                 230                 235                 240

Pro Ser Phe Asn Asp Thr His Asn Val Thr Lys His Thr Leu Asn Ile
                245                 250                 255

Ser Tyr Val Leu Ser Gln Lys Thr Asn Asn Thr Thr Ser Pro Trp Ile
            260                 265                 270

Tyr Ala Ile Pro Met Gly Ala Thr Ala Thr Ile Gly Ala Gly Leu Tyr
        275                 280                 285

Ile Gly Lys His Phe Thr Pro Val Lys Phe Val Tyr Glu Val Trp Arg
    290                 295                 300

Gly Gln
305

(2) INFORMATION FOR SEQ ID NO: 17:

(i) SEQUENCE CHARACTERISTICS:
        (A) LENGTH: 92 amino acids
        (B) TYPE: amino acid
        (D) TOPOLOGY: linear (ii) MOLECULE TYPE: protein (vii) IMMEDIATE SOURCE:
         (B) CLONE: tol.11

(ix) FEATURE:
         (A) NAME/KEY: Protein
         (B) LOCATION: 1..92
         (D) OTHER INFORMATION: /label= UL143

(xi) SEQUENCE DESCRIPTION: SEQ ID NO: 17:

Met Ala Arg Ser Val Lys Thr Ile Arg Ile Gln His Ile Tyr Ser Pro
1               5                   10                  15

Arg Ser Ser Asn Thr Leu Gln His Met Ser Lys Lys Gln Glu Ser Ile
            20                  25                  30
```

```
Ala Thr Ile Thr Phe Gly Arg Ile Thr Cys Cys His Pro Leu Ala Ser
        35                  40                  45

Ile Asn Leu Met Phe Asn Gly Ser Cys Thr Val Thr Val Lys Ile Ser
 50                  55                  60

Met Gly Ile Asn Gly Ser Thr Asn Val His Gln Leu Val Ile Val Leu
 65              70                  75                      80

His Leu Gly Asn Arg Cys Gln Pro Trp Arg Gln Val
                 85                  90
```

(2) INFORMATION FOR SEQ ID NO: 18:

(i) SEQUENCE CHARACTERISTICS:
        (A) LENGTH: 176 amino acids
        (B) TYPE: amino acid
        (D) TOPOLOGY: linear (ii) MOLECULE TYPE: protein (vii) IMMEDIATE SOURCE:
        (B) CLONE: tol.12

(ix) FEATURE:
        (A) NAME/KEY: Protein
        (B) LOCATION: 1..176
        (D) OTHER INFORMATION: /label= UL144

(xi) SEQUENCE DESCRIPTION: SEQ ID NO: 18:

```
Met Lys Pro Leu Ile Met Leu Ile Cys Phe Ala Val Ile Leu Leu Gln
 1               5                  10                  15

Leu Gly Val Thr Lys Val Cys Gln His Asn Glu Val Gln Leu Gly Asn
                 20                  25                  30

Glu Cys Cys Pro Pro Cys Gly Ser Gly Gln Arg Val Thr Lys Val Cys
            35                  40                  45

Thr Asp Tyr Thr Ser Val Thr Cys Thr Pro Cys Pro Asn Gly Thr Tyr
         50                  55                  60

Val Ser Gly Leu Tyr Asn Cys Thr Asp Cys Thr Gln Cys Asn Val Thr
 65                  70                  75                  80

Gln Val Met Ile Arg Asn Cys Thr Ser Thr Asn Asn Thr Val Cys Ala
                 85                  90                  95

Pro Lys Asn His Thr Tyr Phe Ser Thr Pro Gly Val Gln His His Lys
                100                 105                 110

Gln Arg Gln Gln Asn His Thr Ala His Ile Thr Val Lys Gln Gly Lys
             115                 120                 125

Ser Gly Arg His Thr Leu Ala Trp Leu Ser Leu Phe Ile Phe Leu Val
        130                 135                 140

Gly Ile Ile Leu Leu Ile Leu Tyr Leu Ile Ala Ala Tyr Arg Ser Glu
145                 150                 155                 160

Arg Cys Gln Gln Cys Cys Ser Ile Gly Lys Ile Phe Tyr Arg Thr Leu
                165                 170                 175
```

(2) INFORMATION FOR SEQ ID NO: 19:

(i) SEQUENCE CHARACTERISTICS:
        (A) LENGTH: 100 amino acids
        (B) TYPE: amino acid
        (D) TOPOLOGY: linear (ii) MOLECULE TYPE: protein (vii) IMMEDIATE SOURCE:
        (B) CLONE: tol.13

(ix) FEATURE:
        (A) NAME/KEY: Protein
        (B) LOCATION: 1..100
        (D) OTHER INFORMATION: /label= UL145

(xi) SEQUENCE DESCRIPTION: SEQ ID NO: 19:

```
Met Cys Thr Asp Pro Arg Arg Thr Ala Gly Trp Glu Arg Leu Thr His
1               5                   10                  15

His Ala Ser Tyr His Ala Asn Tyr Gly Ala Tyr Ala Val Leu Met Ala
            20                  25                  30

Thr Ser Gln Arg Lys Ser Leu Val Leu His Arg Tyr Ser Ala Val Thr
        35                  40                  45

Ala Val Ala Leu Gln Leu Met Pro Val Glu Ile Val Arg Lys Leu Asp
    50                  55                  60

Gln Ser Asp Trp Val Arg Gly Ala Trp Ile Val Ser Glu Thr Phe Pro
65                  70                  75                  80

Thr Ser Asp Pro Lys Gly Val Trp Ser Asp Asp Ser Ser Met Gly
                85                  90                  95

Gly Ser Asp Asp
            100
```

(2) INFORMATION FOR SEQ ID NO: 20:

(i) SEQUENCE CHARACTERISTICS:
        (A) LENGTH: 117 amino acids
        (B) TYPE: amino acid
        (D) TOPOLOGY: linear (ii) MOLECULE TYPE: protein (vii) IMMEDIATE SOURCE:
        (B) CLONE: tol.14

(ix) FEATURE:
        (A) NAME/KEY: Protein
        (B) LOCATION: 1..117
        (D) OTHER INFORMATION: /label= UL146

(xi) SEQUENCE DESCRIPTION: SEQ ID NO: 20:

```
Met Arg Leu Ile Phe Gly Ala Leu Ile Ile Phe Leu Ala Tyr Val Tyr
1               5                   10                  15

His Tyr Glu Val Asn Gly Thr Glu Leu Arg Cys Arg Cys Leu His Arg
            20                  25                  30

Lys Trp Pro Pro Asn Lys Ile Ile Leu Gly Asn Tyr Trp Leu His Arg
        35                  40                  45

Asp Pro Arg Gly Pro Gly Cys Asp Lys Asn Glu His Leu Leu Tyr Pro
    50                  55                  60

Asp Gly Arg Lys Pro Pro Gly Pro Gly Val Cys Leu Ser Pro Asp His
65                  70                  75                  80

Leu Phe Ser Lys Trp Leu Asp Lys His Asn Asp Asn Arg Trp Tyr Asn
                85                  90                  95

Val Asn Ile Thr Lys Ser Pro Gly Pro Arg Arg Ile Asn Ile Thr Leu
            100                 105                 110

Ile Gly Val Arg Gly
        115
```

(2) INFORMATION FOR SEQ ID NO: 21:

(i) SEQUENCE CHARACTERISTICS:
        (A) LENGTH: 159 amino acids
        (B) TYPE: amino acid
        (D) TOPOLOGY: linear (ii) MOLECULE TYPE: protein (vii) IMMEDIATE SOURCE:
         (B) CLONE: tol.15

(ix) FEATURE:
         (A) NAME/KEY: Protein
         (B) LOCATION: 1..159
         (D) OTHER INFORMATION: /label= UL147

(xi) SEQUENCE DESCRIPTION: SEQ ID NO: 21:

Met Val Leu Thr Trp Leu His His Pro Val Ser Asn Ser His Ile Asn
1               5                   10                  15

Leu Leu Ser Val Arg His Leu Ser Leu Ile Ala Tyr Met Leu Leu Thr
                20                  25                  30

Ile Cys Pro Leu Ala Val His Val Leu Glu Leu Glu Asp Tyr Asp Arg
            35                  40                  45

Arg Cys Arg Cys Asn Asn Gln Ile Leu Leu Asn Thr Leu Pro Val Gly
        50                  55                  60

Thr Glu Leu Leu Lys Pro Ile Ala Ala Ser Glu Ser Cys Asn Arg Gln
65                  70                  75                  80

Glu Val Leu Ala Ile Leu Lys Asp Lys Gly Thr Lys Cys Leu Asn Pro
                85                  90                  95

Asn Ala Gln Ala Val Arg Arg His Ile Asn Arg Leu Phe Phe Arg Leu
            100                 105                 110

Ile Leu Asp Glu Glu Gln Arg Ile Tyr Asp Val Val Ser Thr Asn Ile
        115                 120                 125

Glu Phe Gly Ala Trp Pro Val Pro Thr Ala Tyr Lys Ala Phe Leu Trp
130                 135                 140

Lys Tyr Ala Lys Arg Leu Asn Tyr His His Phe Arg Leu Arg Trp
145                 150                 155

(2) INFORMATION FOR SEQ ID NO: 22:

(i) SEQUENCE CHARACTERISTICS:
         (A) LENGTH: 316 amino acids
         (B) TYPE: amino acid
         (D) TOPOLOGY: linear (ii) MOLECULE TYPE: protein (vii) IMMEDIATE SOURCE:
         (B) CLONE: tol.16

(ix) FEATURE:
         (A) NAME/KEY: Protein
         (B) LOCATION: 1..316
         (D) OTHER INFORMATION: /label= UL148

(xi) SEQUENCE DESCRIPTION: SEQ ID NO: 22:

Met Leu Arg Leu Leu Phe Thr Leu Val Leu Leu Ala Leu His Gly Gln
1               5                   10                  15

Ser Val Gly Ala Ser Arg Asp Tyr Val His Val Arg Leu Leu Ser Tyr
                20                  25                  30

Arg Gly Asp Pro Leu Val Phe Lys His Thr Phe Ser Gly Val Arg Arg
            35                  40                  45

Pro Phe Thr Glu Leu Gly Trp Ala Ala Cys Arg Asp Trp Asp Ser Met
        50                  55                  60

His Cys Thr Pro Phe Trp Ser Thr Asp Leu Glu Gln Met Thr Asp Ser
65                  70                  75                  80

Val Arg Arg Tyr Ser Thr Val Ser Pro Gly Lys Glu Val Thr Leu Gln

```
                    85                  90                  95
Leu His Gly Asn Gln Thr Val Gln Pro Ser Phe Leu Ser Phe Thr Cys
                100                 105                 110

Arg Leu Gln Leu Glu Pro Val Val Glu Asn Val Gly Leu Tyr Val Ala
            115                 120                 125

Tyr Val Val Asn Asp Gly Glu Arg Pro Gln Gln Phe Phe Thr Pro Gln
        130                 135                 140

Val Asp Val Val Arg Phe Ala Leu Tyr Leu Glu Thr Leu Ser Arg Ile
145                 150                 155                 160

Val Glu Pro Leu Glu Ser Gly Arg Leu Ala Val Glu Phe Asp Thr Pro
                165                 170                 175

Asp Leu Ala Leu Ala Pro Asp Leu Val Ser Ser Leu Phe Val Ala Gly
                180                 185                 190

His Gly Glu Thr Asp Phe Tyr Met Asn Trp Thr Leu Arg Arg Ser Gln
            195                 200                 205

Thr His Tyr Leu Glu Glu Met Ala Leu Gln Val Glu Ile Leu Lys Pro
        210                 215                 220

Arg Gly Val Arg His Arg Ala Ile Ile His His Pro Lys Leu Gln Pro
225                 230                 235                 240

Gly Val Gly Leu Trp Ile Asp Phe Cys Val Tyr Arg Tyr Asn Ala Arg
                245                 250                 255

Leu Thr Arg Gly Tyr Val Arg Tyr Thr Leu Ser Pro Lys Ala Arg Leu
            260                 265                 270

Pro Ala Lys Ala Glu Gly Trp Leu Val Ser Leu Asp Arg Phe Ile Val
        275                 280                 285

Gln Tyr Leu Asn Thr Leu Leu Ile Thr Met Met Ala Ala Ile Trp Ala
    290                 295                 300

Arg Val Leu Ile Thr Tyr Leu Val Ser Arg Arg Arg
305                 310                 315

(2) INFORMATION FOR SEQ ID NO: 23:

(i) SEQUENCE CHARACTERISTICS:
        (A) LENGTH: 214 amino acids
        (B) TYPE: amino acid
        (D) TOPOLOGY: linear (ii) MOLECULE TYPE: protein (vii) IMMEDIATE SOURCE:
        (B) CLONE: tol.19

(ix) FEATURE:
        (A) NAME/KEY: Protein
        (B) LOCATION: 1..214
        (D) OTHER INFORMATION: /label= UL130

(xi) SEQUENCE DESCRIPTION: SEQ ID NO: 23:

Met Leu Arg Leu Leu Arg His His Phe His Cys Leu Leu Leu Cys
1               5                   10                  15

Ala Val Trp Ala Thr Pro Cys Leu Ala Ser Pro Trp Ser Thr Leu Thr
                20                  25                  30

Ala Asn Gln Asn Pro Ser Pro Pro Trp Ser Lys Leu Thr Tyr Ser Lys
            35                  40                  45

Pro His Asp Ala Ala Thr Phe Tyr Cys Pro Phe Leu Tyr Pro Ser Pro
        50                  55                  60

Pro Arg Ser Pro Leu Gln Phe Ser Gly Phe Gln Gln Val Ser Thr Gly
65                  70                  75                  80
```

```
Pro Glu Cys Arg Asn Glu Thr Leu Tyr Leu Tyr Asn Arg Glu Gly
                85                  90                  95

Gln Thr Leu Val Glu Arg Ser Ser Thr Trp Val Lys Lys Val Ile Trp
            100                 105                 110

Tyr Leu Ser Gly Arg Asn Gln Thr Ile Leu Gln Arg Met Pro Gln Thr
            115                 120                 125

Ala Ser Lys Pro Ser Asp Gly Asn Val Gln Ile Ser Val Glu Asp Ala
    130                 135                 140

Lys Ile Phe Gly Ala His Met Val Pro Lys Gln Thr Lys Leu Leu Arg
145                 150                 155                 160

Phe Val Val Asn Asp Gly Thr Arg Tyr Gln Met Cys Val Met Lys Leu
                165                 170                 175

Glu Ser Trp Ala His Val Phe Arg Asp Tyr Ser Val Ser Phe Gln Val
            180                 185                 190

Arg Leu Thr Phe Thr Glu Ala Asn Asn Gln Thr Tyr Thr Phe Cys Thr
            195                 200                 205

His Pro Asn Leu Ile Ile
    210

(2) INFORMATION FOR SEQ ID NO: 24:

(i) SEQUENCE CHARACTERISTICS:
        (A) LENGTH: 122 amino acids
        (B) TYPE: amino acid
        (D) TOPOLOGY: linear (ii) MOLECULE TYPE: protein (vii) IMMEDIATE SOURCE:
         (B) CLONE: tol.20

(ix) FEATURE:
         (A) NAME/KEY: Protein
         (B) LOCATION: 1..122
         (D) OTHER INFORMATION: /label= UL149

(xi) SEQUENCE DESCRIPTION: SEQ ID NO: 24:

Met Val Asp Gln Cys Cys Tyr Arg His Leu His Arg Ser Leu Ser Gly
1               5                   10                  15

Gly Pro Asp Val Leu Tyr Ala Ala Ala Gly Thr Gln Arg Glu Gln Gln
            20                  25                  30

Arg Leu Asp Lys Ser Leu Ala Ala Thr Ala Pro Ser Ala Val Ala Gly
            35                  40                  45

Pro Pro Ala Asp Arg Asp Val Val Asp His Arg Thr Glu Thr His Ala
    50                  55                  60

Tyr Glu Thr Pro Arg Tyr Ala Thr Arg Cys Leu Thr Arg Tyr Thr Thr
65                  70                  75                  80

Pro Val Arg Ser Ala Val Arg Arg Thr Thr Cys Gly Lys Arg Val Ala
                85                  90                  95

Ser Gln Ser Pro Pro Arg Ser Cys Leu Val Ala Pro Gln Ser Ser Pro
            100                 105                 110

Ala His Pro Pro Arg His Pro Glu Gly Gly
            115                 120

(2) INFORMATION FOR SEQ ID NO: 25:

(i) SEQUENCE CHARACTERISTICS:
        (A) LENGTH: 642 amino acids
        (B) TYPE: amino acid
        (D) TOPOLOGY: linear
```

```
    (ii) MOLECULE TYPE: protein (vii) IMMEDIATE SOURCE:
         (B) CLONE: tol.21

(ix) FEATURE:
         (A) NAME/KEY: Protein
         (B) LOCATION: 1..642
         (D) OTHER INFORMATION: /label= UL150

(xi) SEQUENCE DESCRIPTION: SEQ ID NO: 25:

Met Gln Leu Cys Ser His Ser Ile Ser Ser Gln Arg His Val Ala Ser
1               5                  10                  15

Ser Met His Cys Arg Ser Arg His Gln Arg Thr Pro Pro Ser Ala Thr
            20                  25                  30

Thr His Gly Pro Cys Ala Pro Thr Ser Arg Ile Leu Arg Arg Leu Leu
         35                  40                  45

Thr Thr Arg Arg Phe Leu Pro Arg Thr Pro Ser Pro Ser Asn Thr Val
50                   55                  60

Cys Cys Ile Arg Arg Arg Leu His Glu Arg Thr Ile Arg His Ser Met
65                   70                  75                  80

Arg Cys Arg Arg Arg Asp Met Ala Ser Ser Ala Ser Thr Pro Val Ser
                85                  90                  95

His Thr Gln Pro Leu Ala Ala Asn His Arg Arg Ser Arg Ile Thr Tyr
                100                 105                 110

Ala Thr Thr Asp Pro Thr Asn Ser Pro Thr Ala Ser Pro Ala Lys Ser
            115                 120                 125

Asp Lys Leu Glu Ala Asp Ala Asp Pro Ala Leu His Arg Arg Pro Ala
        130                 135                 140

Ser Leu Leu Arg His Leu Phe Gln Pro Cys His Ala Gln Arg Gly Thr
145                 150                 155                 160

Ser Asn Arg Ala Thr Ser Gln Arg Ala Ser Leu Asn Ala Val His His
                165                 170                 175

Lys Leu Cys Gly Ala Met Ile Ser Ser Ser Cys Ser Thr Thr Cys Thr
            180                 185                 190

Pro Leu Ile Met Asp Leu Pro Ser Leu Ser Val Glu Leu Ser Ala Gly
        195                 200                 205

His Lys Lys Lys Glu Thr Pro Thr Glu Gly Gly Trp Gly Gly Glu Glu
    210                 215                 220

Gly Glu Asp Asp Val Leu Ala Thr Ile Arg Asn Thr Leu Ser Ala Pro
225                 230                 235                 240

Thr Ser Pro Ala Ala Ala Thr Thr His Arg Leu Ser Phe Pro Gly Glu
                245                 250                 255

Ser Thr Phe Cys Leu Thr Ala Val Ser Glu Cys Ser Gln Arg Arg Thr
            260                 265                 270

Ser Thr Ala Ala Leu Thr Pro Pro Pro Ala Val Ala Ala Phe
        275                 280                 285

Ser Phe Ser Ser Thr Val Ser Glu Thr Gly Thr Phe Pro Gln Ser Thr
    290                 295                 300

Thr Gly Arg Thr Arg Val Asp Asp Thr Ala Val Val Thr Ala Gly Asp
305                 310                 315                 320

Pro Arg Ser Pro Val Thr His Val Thr Leu Leu Gln Ile Phe Arg Leu
                325                 330                 335

Arg Ser Ser Leu Leu Thr Ser Arg Ser Gly Gly Ala Leu Arg Gly Gly
            340                 345                 350

Glu His Glu Ala Ile Pro Lys Val Ala Ser Leu Phe Trp Thr Leu Leu
```

-continued

```
                 355                 360                 365
Lys Ala Thr Gln Ile Val Glu Met Thr His Lys Thr Pro Ser Ala Asp
            370                 375                 380
Ser His Arg Asn Pro Gln Lys Tyr Thr Asp Arg Pro Gln Arg Leu Leu
385                 390                 395                 400
Leu Thr Ala Leu Ala Ile Trp Gln Arg Thr Tyr Asn Asp Thr Arg Ala
                405                 410                 415
Ala His Ala Pro Gln Val Arg Leu Leu Gly Asp Ile Leu Thr Tyr Arg
            420                 425                 430
Arg Pro Gln Thr Ala Thr Ala Ser Thr Lys Ala His Thr Gln Gln Gln
                435                 440                 445
Pro Glu Glu Pro Lys Gly Gln Gln Ile Trp Thr Gln Thr Ala Gly Gln
        450                 455                 460
Ala Ala Pro His Gly Asp Glu Pro His Ser Asp Gly Glu Leu Arg Arg
465                 470                 475                 480
Glu Ser His Ser Ala Pro Pro Thr Ser Arg Thr Leu Pro Asp Thr Ile
                485                 490                 495
Leu Ala Val Lys Arg Arg Ser Val Ala Gln Arg Ser His Val Arg Leu
            500                 505                 510
Asp Ala Lys Pro Gly Leu Asn Glu Arg Asp Gly Phe Arg Gln Arg Leu
            515                 520                 525
Leu Leu Pro Leu Ser Gly Tyr Phe Arg Ala Asn Glu Leu Arg Asn Gln
530                 535                 540
Gln Phe Met Gly Tyr Gly Thr Lys Asn Gly Leu Lys Asn Thr Trp Leu
545                 550                 555                 560
Thr Arg Pro Leu Gly Val Ala Gly Gly Val Arg Glu Thr Ile Gly Glu
                565                 570                 575
Arg Gln Asp Arg Asn Val Ala Asp Ser Ala Thr Gln Arg Val Phe His
            580                 585                 590
Thr Leu Tyr Ala Ala Leu Gln Thr Val Arg Val Trp Tyr Thr Ala Leu
            595                 600                 605
Gly Thr Ala Trp Arg Thr Ser Gly Ser Arg Thr Arg Glu Ser Leu Phe
        610                 615                 620
Asp Gly Pro Arg Arg Asp Arg Gln Ala Ala Arg Leu Arg Arg Leu
625                 630                 635                 640
Glu Leu (2) INFORMATION FOR SEQ ID NO: 26:

(i) SEQUENCE CHARACTERISTICS:
        (A) LENGTH: 336 amino acids
        (B) TYPE: amino acid
        (D) TOPOLOGY: linear (ii) MOLECULE TYPE: protein (vii) IMMEDIATE SOURCE:
         (B) CLONE: tol.22

(ix) FEATURE:
         (A) NAME/KEY: Protein
         (B) LOCATION: 1..336
         (D) OTHER INFORMATION: /label= UL151

(xi) SEQUENCE DESCRIPTION: SEQ ID NO: 26:

Met Val Phe Val Ser Gly Thr Ala Leu Gly Thr Gly Phe His Arg Ala
1               5                   10                  15

Glu Gly Ser Phe Cys Gly Cys Glu Gly Arg Ser Phe Phe Arg Thr Leu
```

```
                    20                  25                  30
Gly Thr Gly Leu Gly Asp Gly Gly Cys Ala Gly Arg Arg Trp Xaa Arg
                35                  40                  45
Xaa Val Ala Gly Thr Gly Ile Thr Leu Gly Thr Gly Thr Arg Gly Pro
 50                  55                  60
Gly Leu Arg Asp Gly Gly Asp Gly Gly Val Cys Gly Glu Asp Gly Gly
 65                  70                  75                  80
Leu Leu Arg Arg Gly Arg Gly Leu Ala Gly Pro Ala Val Ala Gly Val
                85                  90                  95
Cys Gly Asp Gly Gly Leu Leu Gln Arg Arg Gly Leu Arg Gly Gln Glu
                100                 105                 110
Cys Ala Xaa Pro Gly Gly Phe Ala Gly Gly His Gly Thr Gly Gly Gly
                115                 120                 125
Gly Asp Ser Thr Asn His Thr His Thr Gln Leu Thr Ser Ala Val Ala
130                 135                 140
Leu Ser Glu Pro Pro Leu Phe Phe Ile Asn Val Leu Ile Pro Pro Ala
145                 150                 155                 160
Tyr Thr Arg Asn Ala Ala Cys Ser Tyr Ala His Thr Leu Ser Leu His
                165                 170                 175
Ser Asp Met Leu Leu Arg Leu Cys Thr Ala Ala Ala Asp Thr Ser Gly
                180                 185                 190
His Arg His Leu Pro Pro His Met Ala His Val Leu Arg Arg Pro Ala
                195                 200                 205
Ser Tyr Val Val Cys Ser Gln His Gly Ala Phe Phe Pro Ala Arg His
                210                 215                 220
Leu His Arg Thr Pro Ser Ala Ala Phe Ala Val Ala Ser Thr Arg Glu
225                 230                 235                 240
Gln Tyr Ala Thr Ala Cys Ala Val Ala Ala Thr Trp Pro Arg
                245                 250                 255
Leu Pro His Leu Phe Arg Thr Pro Asn Leu Trp Leu Pro Thr Thr Asp
                260                 265                 270
Val Gln Gly Ser Arg Thr Arg Arg Pro Ile Pro Ile Leu Gln Arg
                275                 280                 285
Pro Arg Pro Pro Ser Gln Thr Ser Trp Lys Pro Thr Gln Thr Gln His
290                 295                 300
Ser Ile Asp Ala Arg Pro Arg Cys Cys Ala Thr Ser Ser Ser Pro Ala
305                 310                 315                 320
Thr Pro Asn Ala Ala Leu Pro Thr Glu Pro His Pro Arg Gly Leu Pro
                325                 330                 335
```

(2) INFORMATION FOR SEQ ID NO: 27:

(i) SEQUENCE CHARACTERISTICS:
        (A) LENGTH: 270 amino acids
        (B) TYPE: amino acid
        (D) TOPOLOGY: linear (ii) MOLECULE TYPE: protein (vii) IMMEDIATE SOURCE:
        (B) CLONE: tol.23

(ix) FEATURE:
        (A) NAME/KEY: Protein
        (B) LOCATION: 1..270
        (D) OTHER INFORMATION: /label= UL132

(xi) SEQUENCE DESCRIPTION: SEQ ID NO: 27:

-continued

```
Met Pro Ala Leu Arg Gly Pro Leu Arg Ala Thr Phe Leu Ala Leu Val
1               5                   10                  15

Ala Phe Gly Leu Leu Leu Gln Ile Asp Leu Ser Asp Ala Thr Asn Val
                20                  25                  30

Thr Ser Ser Thr Lys Val Pro Thr Ser Thr Ser Asn Arg Asn Asn Val
        35                  40                  45

Asp Asn Ala Thr Ser Ser Gly Pro Thr Thr Gly Ile Asn Met Thr Thr
    50                  55                  60

Thr His Glu Ser Ser Val His Asn Val Arg Asn Asn Glu Ile Met Lys
65                  70                  75                  80

Val Leu Ala Ile Leu Phe Tyr Ile Val Thr Gly Thr Ser Ile Phe Ser
                85                  90                  95

Phe Ile Ala Val Leu Ile Ala Val Val Tyr Ser Ser Cys Cys Lys His
                100                 105                 110

Pro Gly Arg Phe Arg Phe Ala Asp Glu Glu Ala Val Asn Leu Leu Asp
            115                 120                 125

Asp Thr Asp Asp Ser Gly Gly Ser Ser Pro Phe Gly Ser Gly Ser Arg
    130                 135                 140

Arg Gly Ser Gln Ile Pro Ala Gly Phe Cys Ser Ser Ser Pro Tyr Gln
145                 150                 155                 160

Arg Leu Glu Thr Arg Asp Trp Asp Glu Glu Glu Ala Ser Ala Ala
                165                 170                 175

Arg Glu Arg Met Lys His Asp Pro Glu Asn Val Ile Tyr Phe Arg Lys
                180                 185                 190

Asp Gly Asn Leu Asp Thr Ser Phe Val Asn Pro Asn Tyr Gly Arg Gly
            195                 200                 205

Ser Pro Leu Thr Ile Glu Ser His Leu Ser Asp Asn Glu Glu Asp Pro
        210                 215                 220

Ile Arg Tyr Tyr Val Ser Val Tyr Asp Glu Leu Thr Ala Ser Glu Met
225                 230                 235                 240

Glu Glu Pro Ser Asn Ser Thr Ser Trp Gln Ile Pro Lys Leu Met Lys
            245                 250                 255

Val Ala Met Gln Pro Val Ser Leu Arg Asp Pro Glu Tyr Asp
            260                 265                 270
```

HUMAN CYTOMEGALOVIRUS DNA SEQUENCES

REFERENCE TO RELATED APPLICATIONS

This is a divisional of application Ser. No. 09/253,682, filed Feb. 18, 1999 and issued as U.S. Pat. No. 6,040,170, which is a divisional of application Ser. No. 08/926,922, filed Sep. 10, 1997 and issued as U.S. Pat. No. 5,925,751, which is a divisional of application Ser. No. 08/414,926 filed Mar. 31, 1995 and issued as U.S. Pat. No. 5,721,354.

TECHNICAL FIELD

This invention pertains to the field of virology, specifically to the diagnosis, treatment and prevention of viral infections in humans. More specifically, this invention relates to the diagnosis, treatment and prevention of human cytomegalovirus infections.

BACKGROUND

Human cytomegalovirus (HCMV) is a ubiquitous agent in human populations. Infections are generally asymptomatic, but there can be serious medical sequelae in immunocompromised individuals and in congenitally infected newborns. In immunocompromised individuals, HCMV infection can result in interstitial pneumonia, retinitis progressing to blindness and disseminated infection. Infections in newborns can be severely damaging, with multiple organ involvement including the central nervous system and may also result in auditory damage. The mechanisms of pathogenesis are not understood, although it is believed that host factors, such as cellular and/or humoral immune responses might be involved. See, Alford and Britt, "The Human Herpesviruses", eds Roizman, B., R. J. Whitley and C. Lopez, Raven Press, New York, 1993, pp 227–55. It has also been speculated that genetic variability (either structural or antigenic or both) among different strains of HCMV could be responsible for the variance in clinical manifestations observed. Pritchett, *J. Virol.* 26:152–61 (1980); Lehner, *J. Clin. Microbiol.* 29:2492–2502(1991); Fries, *J. Infect. Dis.* 169:769–74 (1994).

Considerable attention has been focused recently on the analysis of strain variation among HCMV isolates. Some twenty different HCMV strains have been isolated and differentiated by restriction analysis of PCR amplified DNA fragments. Chou, *J. Infect. Dis.* 162:738–42(1990).

One strain, the Towne strain, has been developed into a live, attenuated vaccine and administered with some success in renal transplant patients. See Quinnan, *Annals of Int. Med.* 101:478–83(1985); Plotkin, *Lancet* 1:528–30(1984). However, Towne strain vaccines who were directly challenged by low-passaged Toledo strain wild-type virus in one study were found to resist challenge doses of only 10 plaque-forming units (pfu) or less. Plotkin, *J. Infect. Dis.* 159:860–65(1989). Therefore, it appears the Towne strain may be overly attenuated, i.e., genetically modified so extensively resulting from serial passage in cell culture that it has lost significant immunogenicity presumably due to the loss of genetic information during the cell passage. Advantageously, however, the Towne strain has never been shown to reactivate.

DNA sequence heterogeneity between the Towne strain and another strain of HCMV, AD169, has been found. Pritchett, *J. Virol.* 36:152–61(1980). (A restriction map of the AD169 HCMV genome is disclosed in U.S. Pat. No. 4,762,780.) Variation in the DNA content among other isolated strains of HCMV has also been detected. Huang, *Yale J. Biol. and Med.* 49:29–43(1976). Cleavage patterns of restriction enzyme digests of HCMV DNA of various strains has been analyzed. Kilpatrick, *J. Virol.* 18:1095–1105 (1976); LeFemina, "Structural Organization of the DNA Molecules from Human Cytomegalovirus" in *Animal Virus Genetics*, eds, Field, BN and R. Jaenish, Academic Press, NY (1980); Chandler, *J. Gen. Vitrol.* 67:2179–92(1986); *J. Clin. Microbiol.* 28:2602–07(1990). However, although the gross structural organization of the HCMV genome has been determined and strain-to-strain restriction site polymorphism mapped for many of the strains, strain-to-strain differences in the DNA sequences of the HCMV genome have not been determined. Only partial sequences have been deducted and compared. For example, the DNA and amino acid sequences of the envelope glycoprotein B [gpUL55 (gB)] of both Towne and AD169 strains have been deduced, see Spaete, *Virology.* 167:207–25(1988), and compared with various clinical isolates, see Chou, *J. Infect. Dis.* 163:1229–34(1991), to identify conserved regions and regions of variability. In addition, DNA sequence analysis of certain regions of the gp58/116 gene [gpUL55(gB)], the IMP gene and the IE-1/2 enhancer/promoter has been accomplished, Lehner, *J. Clin. Microbiol.* 29:2494–2502 (1991).

Whereas the complete DNA sequence of the AD169 strain of HCMV has been deduced, (EMBL Accession No. X17403), the complete DNA sequence of the Towne strain has not to our knowledge been deduced. However, it has been speculated that AD169 and another laboratory strain, Davis, are missing two to four kilobase pairs (kb) of DNA sequence compared to the Towne strain at the extreme internal portions of both L repeats. LeFemina, supra, at 52–53.

The public health impact of HCMV infections has not been well controlled by current treatment strategies or available antiviral chemotherapies. Preventative vaccine strategies are likely to prove efficacious because of the observations that seropositive rental allograft recipients are protected from severe HCMV disease and maternal immunity protects the fetus from disease after intrauterine infection. Marshall and Plotkin, "Cytomegalovirus Vaccines" in The Human Herpesviruses, eds Roizman, B., R. J. Whitley and C. Lopez, Raven Press, New York, 1993, pps 381–95. However, an additional obstacle to the development of a vaccine for HCMV is the lack of an animal model system that can be used to test the safety and efficacy of vaccine candidates.

There remains a need in the art for efficacious vaccines for the prophylactic treatment of HCMV in humans.

SUMMARY OF THE INVENTION

In one aspect, the invention provides novel HCMV DNA sequences not heretofore recognized or known in the art. These novel HCMV sequences were isolated from the Toledo and Towne strains of HCMV and comprise DNA that is not shared by reference strain AD169 of HCMV. Accordingly, in this aspect the invention provides novel, isolated, Toledo strain HCMV DNA sequences. As used herein, "isolated" means substantially free from other viral DNA sequences with which the subject DNA is typically found it its native, i.e., endogenous, state. These novel Toledo HCMV DNA sequences are characterized by comprising the same or substantially the same nucelotide sequence as in FIG. 1. (SEQ ID NO:6), or active fragments thereof. The DNA sequences may include 5' and 3' non-coding sequences flanking the coding sequence. The DNA sequences may be in inverted orientation with respect to the orientation shown in FIG. 1. Segments or fragments of the DNA sequence shown in FIG. 1 (SEQ ID NO:6) may be rearranged or inverted internally. The DNA sequences of the invention also comprise nucleotide sequences capable of hybridizing under stringent conditions, or which would be capable of hybridizing under said conditions but for the degeneracy of the genetic code to a sequence corresponding to the sequence of FIG. 1. FIG. 1 (SEQ ID NO:6) illustrates the DNA sequence of the novel Toledo strain HCMV. Twenty one open reading frames (ORFs) were identified in this sequence. The putative amino acid sequences of these novel Toledo strain HCMV ORFs are enumerated in sequence identification numbers 7 through 27, pages 58 through 78, infra. In FIG. 1, the beginning and ending of the 21 ORFs are identified by the arrows and the designations "UL133", "UL134", etc. (see infra.). In rearranged sequences of the invention novel open reading frames may be created or destroyed.

In another aspect, the invention provides additional novel HCMV DNA sequences not heretofore recognized or known in the art. These additional sequences were isolated from the Towne strain of HCMV and comprise DNA that is not shared by the AD169 strain or by the Toledo strain of HCMV. Accordingly, in this aspect the invention provides novel Towne strain HCMV sequences. These novel Towne HCMV DNA sequences are characterized by as comprising the same or substantially the same nucleotide sequence as in FIG. 2 (SEQ ID NO: 1), or active fragments thereof. The DNA sequence may include 5' and 3' non-coding sequences flanking the coding sequence. The DNA sequences of the invention also comprise nucleotide sequences capable of hybridizing under stringent conditions, or which would be capable of hybridizing under said conditions but for the degeneracy of the genetic code to a sequence corresponding to the sequence of FIG. 2 (SEQ ID NO:1). FIG. 2 (SEQ ID NO:1) illustrates the DNA sequence of the novel Towne strain HCMV. Four ORFs were identified in this sequence. The putative amino acid sequences of these novel ORFs are enumerated in sequence identification numbers 2 through 5, pages 42 through 45 infra. In FIG. 2, the beginning and ending of the 4 ORFs are identified by the arrows and the designations UL147, UL152, UL153 and UL154.

It is understood that the DNA sequences of this invention may exclude some or all of the signal and/or flanking sequences. In addition, the DNA sequences of the present invention may also comprise DNA capable of hybridizing under stringent conditions, or which would be capable of hybridizing under such conditions but for the degeneracy of the genetic code, to an isolated DNA sequence of FIG. 1 or FIG. 2 (SEQ ID NOS:6 and 1). As used herein, "stringent conditions" means conditions of high stringency, for example 6 X SSC, 0.2% polyvinylpyrrolidone, 0.2% Ficoll, 0.2% bovine serum albumin, 0.1% sodium dodecyl sulfate, 100 µg/ml salmon sperm DNA and 15% formamide at 68 degrees C. (See materials and Methods, Part C, infra).

Accordingly, the DNA sequences of this invention may contain modifications in the non-coding sequences, signal sequences or coding sequences, based on allelic variation, species or clinical isolate variation or deliberate modification. Using the sequences of FIG. 1 and 2 (SEQ ID NOS:6 and 1), it is within the skill in the art to obtain other modified DNA sequences: the sequences can be truncated at their 3'-termini and/or their 5'-termini, the gene can be manipulated by varying individual nucleotides, while retaining the original amino acid(s), or varying the nucleotides, so as to modify amino acid(s). Nucleotides can be substituted, inserted or deleted by known techniques, including for example, in vitro mutagenesis and primer repair. In addition, short, highly degenerate oligonucleotides derived from regions of imperfect amino acid conversation can be used to identify new members of related viral and cellular families. RNA molecules, transcribed from a DNA of the invention as described above, are an additional aspect of the invention.

In another aspect, the invention provides novel HCMV proteins, which are substantially free from other HCMV proteins with which they are typically found in their native state. These novel HCMV proteins comprise the open reading frames (ORFs) UL133 (SEQ ID NO:7), UL134 (SEQ ID NO:8), UL135 (SEQ ID NO:9), UL136 (SEQ ID NO:10), UL137 (SEQ ID NO:11), UL138 (SEQ ID NO:12), UL139 (SEQ ID NO:13), UL140 (SEQ ID NO:14), UL141 (SEQ ID NO:15), UL142 (SEQ ID NO:16), UL143 (SEQ ID NO:17), UL144 (SEQ ID NO:18), UL145 (SEQ ID NO:19), UL146 (SEQ ID NO:20), UL147 (SEQ ID NO:21), UL148 (SEQ ID NO:22), UL149 (SEQ ID NO:24), UL150 (SEQ ID NO:25), and/or UL151 (SEQ ID NO:26) identified in the novel Toledo strain DNA sequence UL147 (SEQ ID NO:2), UL152 (SEQ ID NO:3), UL153 (SEQ ID NO:4 ) and/or UL154 identified in the novel Towne strain DNA sequence. Two additional HCMV ORFs were identified in the novel Toledo strain DNA sequence, UL130 and UL132 (SEQ ID NO:23 and 27). These two sequences are also present in AD169 (see FIG. 5). The proteins may be produced by recombinant genetic engineering techniques. They may additionally be purified from cellular sources infected with HCMV. They may also be synthesized by chemical techniques. One skilled in the art could apply a combination of the above-identified methodologies to synthesize the protein. Additionally, analogs of the HCMV proteins of the invention are provided and include truncated polypeptides, e.g., mutants in which there are variations in the amino acid sequence that retain biological activity, as defined below, and preferably having a homology of at least 80%, more preferably 90%, and most preferably 95%, with the corresponding regions of the HCMV Towne or Toledo amino acid sequences (SEQ ID NOS:2, 3, 4, 5, 7, 8 ,9, 10, 11, 12 ,13, 14, 15, 16, 17, 18, 19, 20, 21, 22, 23, 24, 25, 26, and 27). Examples include polypeptides with minor amino acid variations from the native amino acid sequences of HCMV Toledo or Towne amino acid sequences (SEQ ID NOS: 2, 3, 4, 5, 7, 8, 9, 10, 11, 12, 13, 14, 15, 16, 17, 18, 19, 20, 21, 22, 23, 24, 25, 26, and 27); in particular, conservative amino acid replacements. Consarative replacements are those that take place within a family of amino acids that are related in their side chains. Genetically encoded amino acids are generally divided into four families: (1) acidic=aspartate, glutamate; (2) basic=lysine, arginine, histidine; (3) non-polar=alanine, valine, leucine, isoleucine, proline, phenylalanine, methionine, trypotphan; and (4) uncharged polar=glycine, asparagine, glutamine, cystine, serine, thereonine, tyrosine. Phenylalanine, trypotphan, and tyrosine are sometimes classified jointly as aromatic amino acids. For example, it is reasonable to expect that an isolated replacement of a leucine with an isoleucine or valine, an aspartate with a glutamate, a thereonine with a serine, or a similar conservative replacement of an amino acid with a structurally related amino acid will not have a major effect on activity or functionality.

Using the Toledo or Towne amino acid sequences (SEQ ID NOS: 2, 3, 4, 5, 7, 8, 9, 10, 11, 12, 13, 14, 15, 16, 17, 18, 19, 20, 21, 22, 23, 24, 25, 26, and 27) it is within the skill in the art to obtain other polypeptides or other DNA sequences encoding the HCMV Toledo or Towne protein from clinical isolates or HCMV. For example, the structural gene can be manipulated by varying individual nucleotides, while retaining the correct amino acid(s), or varying the nucleotides, so as to modify the amino acids, without loss of activity. Nucleotides can be substituted, inserted, or deleted by known techniques, including, for example, in vitro mutagenesis and primer repair. The structural gene can be truncated at its 3'-terminus and/or its 5'-terminus while retaining its activity. It also may be desirable to remove the region encoding the signal sequence, and/or to replace it with a heterologous sequence. It may also be desirable to ligate a portion of the HCMV Toledo or Towne amino acid sequences (SEQ ID NOS:2, 3, 4, 5, 7, 8, 9, 10, 11, 12, 13, 14, 15, 16, 17, 18, 19, 20, 21, 22, 23, 24, 25, 26, and 27), preferably that which includes the amino terminal domain to a heterologous coding sequence, and thus to create a fusion peptide of HCMV Toledo or Towne.

In designing such modifications, it is expected that changes to nonconserved regions of the HCMV Toledo or Towne amino acid sequences (SEQ ID NOS:2, 3, 4, 5, 7, 8, 9, 10, 11, 12, 13, 14, 15, 16, 17, 18, 19, 20, 21, 22, 23, 24, 25, 26, and 27) will have relatively smaller effects on activity, whereas changes in the conserved regions, and particularly in or near the amino terminal domain are expected to produce larger effects. Amino acid residues that are conserved between the HCMV Toledo or Towne amino acid sequences (SEQ ID NOS:2, 3, 4, 5, 7, 8, 9, 10, 11, 12, 14, 15, 17, 18, 19, 21, 22, 23, 24, 25, 26,and 27) and at least two other sequences, for example, from HCMV clinical isolates are not expected to be candidates for substitution. A residue which shows conservative variations among the HCMV sequences and at least two of the other sequences is expected to be capable of similar conservative substitution of the HCMV sequences. Similarly, a residue which varies nonconservatively among the HCMV sequences and at least three of the other sequences is expected to be capable of either conservative or nonconservative substitution. When designing substitutions to the HCMV sequences, replacement by an amino acid which is found in the comparable aligned position of one of the other sequences is especially preferred.

Additionally provided by this invention is a recombinant DNA vector comprising vector DNA and a DNA sequencing encoding an HCMV Toledo polypeptide or HCMV Towne polypeptide. The vector provides the HCMV Toledo or Towne DNA in operative association with a regulatory sequence capable of directing the replication and expression of an HCMV Toledo or Towne protein in a selected host cell. Host cells transformed with such vectors for use in expressing recombinant HCMV Toledo or Towne proteins are also provided by this invention. Also provided is a novel process for producing recombinant HCMV Toledo or Towne proteins or active fragments thereof. In this process, a host cell line transformed with a vector as described above containing a DNA sequence (SEQ ID NOS:1 and 6) encoding expression of an HCMV Toledo or Towne protein in operative association with a suitable regulatory sequence capable of directing replication and controlling expression of an HCMV Toledo or Towne protein is cultured under appropriate conditions permitting expression of the recombinant DNA. The expressed protein is then harvested from the host cell or culture medium using suitable conventional means. This novel process may employ various known cells as host cell lines for expression of the protein. Currently preferred cells are mammalian cell lines, yeast, insect and bacterial cells. Especially preferred are mammalian cell lines.

The practice of the invention will employ, unless otherwise indicated, conventional techniques of molecular biology, microbiology, recombinant DNA manipulation and production, and immunology, which are within the skill of the art. Such techniques are explained fully in the literature. See, e.g., Sambrook, *Molecular Cloning: A Laboratory Manual*, Second Edition (1989); *DNA Cloning*, Volumes I and II (D. N. Glover, Ed. 1985); *Oligonucleotide Synthesis* (M. J. Gait, Ed. 1984); *Nucleic Acid Hybridization* (B. D. Hames and S. J. Higgins, Eds. 1984); *Transcription and Translation* (B. D. Hames and S. J. Higgins, Eds. 1984); *Animal cell Culture* (R. I. Freshney, Ed. 1986); *Immobilized Cells and Enzymes* (IRL Press, 1986); B. Perbal, *A Practical guide to Molecular Cloning* (1984); the series, *Methods in Enzymology* (Academic Press, Inc.); *Gene Transfer Vectors for Mammalian Cells* (J. H. Miller and M. P. Calos, Eds. 1987, Cold Spring Harbor Laboratory), *Methods in Enzymology*, Volumes 154 and 155 (Wu and Grossman, and Wu, Eds., respectively), (Mayer and Walker, Eds.) (1987); *Immunochemical Methods in Cell and Molecular Biology* (Academic Press, London), Scopes, (1987); *Protein Purification: Principles and Practice*, Second Edition (Springer-Verlag, N.Y.); and *Handbook of Experimental Immunology*, Volumes I–IV (D. M. Weir and C. C. Blackwell, Eds 1986). All patents, patent applications and publications mentioned herein, both supra and infra, are hereby incorporated by reference.

Additionally provided by this invention are compositions for detecting HCMV infections in humans. These compositions comprise probes having at least one single-stranded fragment of at least 10 bases in length, more preferably 15 bases in length, of the novel Toledo sequence, and fragments hybridizing to these single-stranded fragments under stringent hybridization conditions and non-cross-hybridizing with human DNA. Additionally, these compositions comprise at least one single-stranded fragment of at least 10 bases in length, more preferably 15 bases in length, of the novel Towne sequence, and fragments hybridizing to these single-stranded fragments under stringent hybridizing with human DNA. Such probe compositions may additionally comprise a label, attached to the fragment, to provide a detectable signal, as is taught in U.S. Pat. No. 4,762,780.

Further provided by this invention are methods for detecting an HCMV infection in a human host. Such methods comprise combining under predetermined stringency conditions a clinical sample suspected of containing HCMV DNA with at least one single-stranded DNA fragment of the novel Toledo or Towne strain of HCMV having at least 10 bases, more preferably 15 bases, and being non-cross hybridizing with human DNA, and detecting duplex formation between the single-stranded Toledo or Towne strain HCMV fragments and the sample DNA. Alternatively, PCR may be used to increase the viral nucleic acid copy number by amplification to facilitate the identification of HCMV in infected individuals. In such case, the single-stranded Toledo or Towne strain DNA sequence fragments of the present invention can be used to construct PCR primers for PCR-based amplification systems for the diagnosis of HCMV. Such systems are well known in the art. See for example, U.S. Pat. No. 5,008,182 (detection of AIDS associated virus by PCR) and Hedrum, PCR Methods and Applications 2:167–71(1992) (detection of Chlamydia trachomatis by PCR and immunomagnetic recovery).

The DNA sequences of this invention may also be used to prepare immunizing compositions. The novel Toledo DNA sequences are recombined into the Towne Strain or AD169 strain of HCMV and these recombinant viruses tested for growth properties in endothelial cells or in human tissues transplanted in SCID mice or tested in the rate eye model. Mocarski, *Proc. Nat. Acad. Sci* 90:104–08(1993). Such recombinants will show increased immunogenicity over that shown by the Towne-125 strain currently in use in humans, without exhibiting the full virulence shown by the Toledo-1 strain. Therefore, a further aspect of the invention is immunizing compositions comprising either the Towne strain or the AD169 reference strain of HCMV to which the novel Toledo DNA sequence, or analogs or fragments thereof, have been added, resulting in increased immunogenicity of the recombinant virus. The invention also includes a method for the prophylactic treatment of HCMV in humans comprising administering to a human patient an immunogenically inducing effective amount of an immunizing composition of the invention is a suitable pharmaceutical carrier. Still another aspect of the invention is a method of stimulating an immune response against CMV by administering to a patient an immunogenically inducing effective amount of an immunizing composition of the invention is a suitable pharmaceutical vehicle.

Other aspects and advantages of this invention are described in the following detailed description.

BRIEF DESCRIPTION OF THE DRAWINGS

FIG. 1 illustrates the novel Toledo DNA sequence of the invention isolated from the Toledo strain of HCMV. The arrows indicate the beginnings and ends of nucelotide sequences encoding the 21 putative amino acid sequences identified.

FIG. 2 illustrates the novel Towne DNA sequence of the invention isolated from the Towne strain of HCMV. The arrows indicate the beginnings and ends of the nucleotide sequences encoding the 4 putative amino acid sequences identified.

FIG. 3 is a schematic representation of a Southern blot of restriction enzyme digested Towne and Toledo HCMV strain DNA as detailed in Example 1. The arrow indicates a 5 kbp (kilobase pair) band of Toledo DNA on the BamHI digest that is lacking in the Towne DNA, signifying the presence of additional Toledo DNA sequence.

FIG. 4 illustrates a composite autoradiograph of the restriction enzyme digested DNA from AD169, Towne, Toledo and five clinical isolates of HCMV as described in Example 3.

FIG. 5 is a schematic presentation of the novel open reading frames identified in the novel Toledo and Towne DNA sequences.

FIG. 6 is a schematic illustration of the relative positions of novel sequences identified in Toledo genomic DNA, Towne genomic DNA in a comparison with AD169 strain genomic DNA.

DETAILED DESCRIPTION

A. Introduction

The invention provides two novel HCMV DNA sequences, termed Toledo sequence and Towne sequence, not heretofore recognized or known in the art. The invention also provides immunization compositions and methods using the novel HCMV DNA sequences of the invention and also provides other diagnostic and therapeutic uses for the sequences and their protein products. The new DNA sequences were originally found in the Toledo and Towne strains of HCMV. Details of the sequences and structural characteristics are provided in the Examples below.

Most desirably, HCMV immunogenic compositions are provided that comprise reference strain AD169 or Towne to which the novel Toledo DNA sequences, or analogs or fragments thereof, have been added in order to increase the immunogenicity of the overly-attenuated strain. Thus, one aspect of this invention includes isolated DNA and corresponding RNA sequences as disclosed in FIGS. 1 and 2 (SEQ ID NOS:6 and 1). As used herein, "isolated" means substantially free from other nucleotides or polypeptide sequences with which the subject nucleotide sequence or polypeptide sequence is typically found in its native, i.e., endogenous, state. In another aspect, the invention comprises isolated HCMV Towne or Toledo protein encoded by the respective HCMV Towne or Toledo DNA sequences (SEQ ID NOS:2, 3, 4, 5, 7, 8, 9, 10, 11, 12, 13, 14, 15, 16, 17, 18, 19, 20, 21, 22, 23, 24, 25, 26, and 27).

Another aspect of this invention includes diagnostic assays for the detection of HCMV strain variants. In brief, such diagnostic assays include the use of DNA sequence fragments of the invention as primers for amplifying HCMV related nucleic acids in a polymerase chain reaction (PCR) or by direct detection by hybridization. The diagnostic assays of the invention may also include the use of specific antibodies against the novel ORFs encoded by the Toledo or Towne DNA sequences disclosed here. Yet another aspect of the invention is the use of the novel DNA sequences modified with a unique restriction site, to act as vaccine markers.

It is anticipated that the invention will enable the production of vaccines that offer advantages over the current HCMV vaccine, which is overly attenuated and therefore not consistently effective in eliciting an immune response. More specifically the introduction or insertion of the novel Toledo strain sequences of the present invention into the Towne strain or into the AD169 strain will result in the introduction of specific DNA sequences in the HCMV Towne genome that are not possible using the cell passage vaccines. Importantly, for vaccine production, this enables precise measurement of the degree of attenuation introduced by different fragments of the DNA sequences of the invention, thereby enabling the controlled modification in the attenuation of the Towne strain that is needed in the art to correct the Towne's strain's overly attenuated characteristic and improve its function as an immunogenic composition.

B. Recombinant AD169 or Towne HCMV

Recombinant AD169 or Towne DNA is derived by co-transfecting a plasmid containing the novel Toledo sequence, or analogs or fragments thereof, and a selectable marker such as gpt or β-galactosidase in primary fibroblast cells, or other cell lines known to be permissive for growth of CMV. Recombinant viruses are selected by growth in media containing mycophenolic acid or identified by blue plaque phenotypes after applying a chromogenic substrate such as X-gal. Recombinant viruses are plaque purified and characterized by restriction enzyme analysis and Southern blotting procedures. The novel HCMV Toledo sequence, or analogs or fragments thereof, may be used unmodified with respect to the endogenous promoter and transcription termination signals. Alternatively, the HCMV Toledo strain DNA coding region can be placed under transcriptional control of a promoter such as the CMV (cytomegalovirus) major immediate early promoter, the SV40 early promoter or some other viral or cellular promoter that generates adequate levels of expression, as discussed herein.

Modified Towne or AD169 strain HCMV is grown in tissue culture cells. For experiments with mammals, not including humans, cells such as human foreskin fibroblasts (HF) or MRC-5 cells are used to propagate the virus. The virus is harvested from cultures of these cells and the isolated recombinant virus is then be further studied for its ability to elicit an immune response and provide protection against HCMV infection.

For use in humans, the recombinant virus is produced from an FDA approved cell line in large scale amounts. Such cells include MCR-5 or WI-38 cells (both are primary human diploid fibroblasts). The recombinant virus is generated in the production cell line by transfection of viral DNA or capsids prepared from recombinant virus isolated from another cell line. The method of transfection should prevent the contamination of FDA approved cells with adventitious agents or contaminants from a non-qualified cell line. A HCMV virus produced from the above cell lines will be used to infect progressively larger flasks of tissue culture cells. Infected cells will be used as subsequent inoculums. Viable infected tissue culture cells are removed from the tissue culture vessels using trypsin and added to a 1 to 100 fold (or more) excess of uninfected cells to accomplish progressively larger inoculations. Once an optimal yield is obtained the virus will be harvested from the tissue culture cells. This process can be repeated until a large scale production is achieved. Infected cells will be removed from the tissue culture vessel and disrupted using for example, sonication, dounce homogenization or some combination of the above. The viruses are then isolated from cellular material using centrifugation techniques known in the art. Once the virus is isolated a stabilizing agent is added, such as a carbohydrate or carbohydrate derivative and the virus is then aliquoted and lyophilized.

C. Immunogenic Compositions

Immunogenic compositions can be administered to subjects to prevent HCMV infections. The immunogenic compositions prevent HCMV infections by stimulating the immune system with an attenuated virus incapable of fully manifesting the disease. A major advantage of the HCMV immunogenic compositions provided herein is that its increased degree of immunogenicity will result in move effective protection of an HCMV infection in the population.

The Towne strain of HCMV will preferably serve as the parent strain due to its proven inability to reactivate. To make HCMV immunogenic compositions, full, truncated and/or modified novel Toledo DNA sequences are introduced into a HCMV AD169 or Town strain virus as discussed herein. The effectiveness of the immunogenic composition in preventing HCMV infections will be measured in humans. Humans will be first inoculated with PFU's ranging from 100–20,000 PFU of mutant virus per inoculation, PFUs are measured as discussed herein. After the first inoculation, a second booster injection of similar or increased dosage usually may be given. Subjects will be exposed to wild-type HCMV after the first or second inoculation and the occurrence of CMV infections observed. Potential side effects of the vaccine will be monitored in volunteer adults previously exposed to CMV, before inoculating subjects that have not ever developed CMV infections. Attenuated virus is used without an adjuvant and with a physiologically suitable carrier.

As is known in the art and discussed herein, the novel DNA is inserted into the Towne or AD169 viral genome using, for example, homologous recombination techniques. The insertion is generally made into a gene which is non-essential in nature. Plasmid shuttle vectors that greatly facilitate the construction of recombinant viruses have been described. See, for example, Spaete and Mocarski, *Proc. Nat. Acad. Sci* 84:7213–17(1987). Expression of the polypeptide encoded by the novel Toledo DNA then occurs in cells or individuals which are immunized with the live recombinant virus.

Alternatively, the purified novel HCMV proteins may be employed in therapeutic and/or subunit immunogenic compositions for preventing and treating HCMV related conditions. Such pharmaceutical compositions comprise an immunogenically-inducing effective amount of one or more of the proteins of the present invention in admixture with a pharmaceutically acceptable carrier, for example and adjuvant/antigen presentation system such as alum. Other adjuvant/antigen presentation systems, for instance, MF59 (Chiron Corp.), QS-21 (Cambridge Biotech Corp.) 3-DMPL (3-Deacyl-Monophosphoryl Lipid A) RibiImmunoChem Research, Inc.), clinical grade incomplete Freund's adjuvant (IFA), fusogenic liposomes, water soluble polymers or Iscoms (Immune stimulating complexes) may also be used. Other exemplary pharmaceutically acceptable carriers or solutions are aluminum hydroxide, saline and phosphate buffered saline. The composition can be systemically administered, preferably subcutaneously or intramuscularly, in the form of an acceptable subcutaneous or intramuscular solution. Also inoculation can be effected by surface scarification or by inoculation of a body cavity. The preparation of such solutions, having due regard to pH, isotonicity, stability and the like is within the skill in the art. The dosage regimen will be determined by the attending physician considering various factors known to modify the action of drugs such as for example, physical condition, body weight, sex, diet, severity of the condition, time of administration and other clinical factors. Exemplary dosage ranges comprise between about 1 $\mu$g to about 1000 $\mu$g of protein.

In practicing the method of treatment of this invention, an immunologicaly-inducing effective amount of protein is administered to a human patient in need of therapeutic or prophylactic treatment. An immunologically-inducing effective amount of a composition of this invention is contemplated to be in the range of about 1 microgram to about 1 milligram per dose administered. The number of doses administered may vary, depending on the above mentioned factors.

D. Diagnostic Assays and Use as a Vaccine Marker

The novel Toledo and Towne DNA sequences of the present invention can be used in diagnostic assays to detect in a sample, to detect Toledo and Towne—like sequences and to detect strain differences in clinical isolates of HCMV using either chemically synthesized or recombinant Toledo or Towne DNA fragments. Additionally, the novel sequences can be used as a vaccine marker to differentiate between an individual or sample infected with or containing wild type HCMV and an individual or sample infected with or containing a HCMV vaccine, i.e., a live attenuated HCMV vaccine currently in use such as the Towne vaccine. In yet another embodiment, fragments of the DNA sequences can also be linked to secondary nucleic acids with sequences that either bind a solid support or other detection probes for use in diagnostic assays. In one aspect of the invention, fragments of the novel Toledo or Towne DNA sequences (SEQ ID NOS:1 and 3) comprising at least between 10 and 20 nucleotides can be used as primers to amplify nucleic acids using polymerase chain reaction (PCR) methods well known in the art and as probes in nucleic acid hybridization assays to detect target genetic material such as HCMV DNA in clinical specimens (with or without PCR). See for example, U.S. Pat. Nos. 4,683,202; 4,638,195; 5,091,310; 5,008,182 and 5,168,039. In an exemplary assay, a conserved region of the novel DNA sequence among virus variants is selected as the sequence to be amplified and detected in the diagnostic assay. Oligonucleotide primers at least substantially complementary to (but preferably identical with) the sequence to be amplified are constructed and a sample suspected of containing a HCMV nucleic acid sequence to be detected is treated with primers for each strand of HCMV nucleic acid sequence to be detected, four different deoxynucleotide triphosphates and a polymerization agent under appropriate hybridization conditions such that an extension product of each primer is synthesized that is complementary to the HCMV nucleic acid sequences suspected in the sample, which extension products synthesized from one primer, when separated from its complement can serve as a template for synthesis of the extension product of the other primer in a polymerase chain reaction. After amplification, the product of the PCR can be detected by the addition of a labeled probe, likewise constructed from the novel DNA sequence, capable of hybridizing with the amplified sequence as is well known in the art. See, e.g. U.S. Pat. No. 5,008,182.

In another embodiment the probes or primers can be used in a vaccine marker assay to detect a vaccine or wild type infection. Alternatively, introduction of a restriction site into the novel DNA sequence will provide a vaccine marker that can be used with PCR fragments to detect such differences in a restriction digest. Such procedures and techniques for detecting sequence variants, such as, point mutations with the expected location or configuration of the mutation, are known in the art and have been applied in the detection of sickle cell anemia, hemoglobin C disease, diabetes and other diseases and conditions as disclosed in U.S. Pat. No. 5,137,806. These methods are readily applied by one skilled in the art to detect and differentiate between wild type and vaccine infections in HCMV.

In another embodiment the novel Toledo or Towne DNA sequences can be used in their entirety or as fragments to detect the presence of DNA sequences, related sequences, or transcription products in cells, tissues, samples and the like using hybridization probe techniques known in the art or in conjunction with one of the methods discussed herein. When used as a hybridization probe, fragments of the novel DNA sequences of the invention are preferably 50–200 nucleotides long, more preferably 100–300 nucleotides long and most preferably greater than 300 nucleotides long.

E. Vectors and Chimeric Virus Production

The novel DNA sequences of the invention can be expressed in different vectors using different techniques known in the art resulting in the generation of chimeric virus. Useful and known techniques include marker transfer or homologous recombination, direct in vitro ligation, defective vector technology and amplicon generation (see, e.g., Frenkel, N. et. al., *Gene Transfer and Cancer*, edited by M. L. Pearson and N. L. Sternberg(1984), Kwong, A. D. and Frenel, *Virology* 142, 421–425(1985); U.S. Pat. (Ser. No. 07/923,015 by Roizman). Vectors used in such techniques include cosmids, plasmids, and infective or defective viruses. Such vectors are known in the art. (A cosmid as used herein is a plasmid containing a lambda bacteriophage cos site. The cos site is the cis signal for packaging lambda DNA. Therefore, a cosmid, unlike a plasmid, can be packaged with high efficiency into a lambda head in vitro. This technique allows cloning of very large (30–45 kpb) fragments of DNA.) The vectors can be either single stranded or double stranded and made of either DNA or RNA.

Generally, the DNA sequence is inserted into the vector alone or linked to other HCMV genomic DNA. In direct in vitro ligation applications, the isolated sequence alone is used. In homologous recombination and marker transfer flanking nucleic acid sequences are required to effect transfer of the sequence into a HCMV viral genome. For use in viral complementation using cosmids and other vectors discussed herein the sequence (or a fragment) thereof) in a vector is preferably operatively linked to at least 1 kb of HCMV genomic nucleic acid and more preferably at least 5 kb of HCMV nucleic acid. The HCMV genomic nucleic acid can be on one side or both sides of the open reading frame. If only a specific region of the open reading frame is to be used to generate a mutant virus, an open reading frame or fragment thereof is inserted into a vector.

F. Novel Toledo and Towne Protein

Another aspect of the invention includes the isolated proteins encoded by the Toledo or Towne DNA sequence as taught herein. The proteins can be used to study and modify the life cycle of HCMV because they may encode surface glycoproteins that may be immunogenic and responsible for tissue tropism or influence the immune response in an infected individual. Such proteins could therefore by used in the production of a subunit vaccine against CMV. The construction of such CMV subunits vaccine candidates is known the art. See, for example, Spaete, *Virology* 167:207–25(1988).

Twenty-one novel Toledo and four novel Towne proteins have been identified by ORF analysis. The novel Toledo proteins include UL130 (SEQ ID NO:23), UL132 (SEQ ID NO:27), UL133 (SEQ ID NO:7), UL134 (SEQ ID NO:8), UL135 (SEQ ID NO:9), UL136 (SEQ ID NO:10), UL137 (SEQ ID NO:11), UL138 (SEQ ID NO:12), UL139 (SEQ ID NO:13), UL140 (SEQ ID NO:14), UL141 (SEQ ID NO:15), UL142 (SEQ ID NO:16), UL143 (SEQ ID NO:17), UL144 (SEQ ID NO:18), UL145 (SEQ ID NO:19), UL146 (SEQ ID NO:20), UL147 (SEQ ID NO:21), UL148 (SEQ ID NO:22), UL149 (SEQ ID NO:24), UL150 (SEQ ID NO:25), and/or UL151 (SEQ ID NO:26). UL130 is encoded by nucleotides 13109 through 13753, as shown in FIG. 1. UL132 is encoded by nucleotides 11673 through 12485, as shown in FIG. 1. UL133 is encoded by nucleotides 51 through 824, as shown in FIG. 1. UL134 is encoded by nucleotides 541 through 1068, as shown in FIG. 1. UL135 is encoded by nucleotides 941 through 1927, as shown in FIG. 1. UL136 is encoded by nucleotides 2018 through 2740 , as shown in FIG. 1. UL137 is encoded by nucleotides 2599 through 2890, as shown in FIG. 1. UL138 is encoded by nucleotides 2823 through 3332, as shown in FIG. 1. UL139 is encoded by nucleotides 3895 through 4302, as shown in FIG. 1. UL140 is encoded by nucleotides 4484 through 4828, as shown in FIG. 1. UL141 is encoded by nucleotides 5098 through 6375, as shown in FIG. 1. UL142 is encoded by nucleotides 6448 through 7368, as shown in FIG. 1. UL143 is encoded by nucleotides 7353 through 7631, as shown in FIG. 1. UL144 is encoded by nucleotides 8008 through 8538, as shown in FIG. 1. UL145 is encoded by nucleotides 8867 through 9169, as shown in FIG. 1. UL146 is encoded by nucleotides 9450 through 9803, as shown in FIG. 1. UL147 is encoded by nucleotides 9868 through 10347, as shown in FIG. 1. UL148 is encoded by nucleotides 10646 through 11596, as shown in FIG. 1. UL149 is encoded by nucleotides 15756 through 16124, as shown in FIG. 1. UL150 is encoded by nucleotides 15874 through 17802, as shown in FIG. 1. UL151 is encoded by nucleotides 17389 through 18299, as shown in FIG. 1.

The novel Towne proteins include UL147, UL152, UL153 and UL154 (SEQ ID NOS:2, 3, 4 and 5, respectively). UL147 is encoded by nucleotides 841 through 1321, as shown in FIG. 2. UL152 is encoded by nucleotides 1365 through 1721, and shown in FIG. 2 UL153 is encoded by nucleotides 2501 through 3337, as shown in FIG. 2. UL154 is encoded by nucleotides 3512 through 4711, as shown in FIG. 2.

"Toledo and/or Towne protein or proteins" as used herein refer to the above sequences, also enumerated in the sequence listing. "Toledo and/or Towne protein or proteins" also refers to an homologous protein from any strain or clinical isolate of HCMV, including HCMV proteins that are at least 90% homologous to the Toledo or Towne amino acid sequences (SEQ ID NOS:2, 3, 4, 5, 7, 8, 9, 10, 11, 12, 13, 14, 15, 16, 17, 18, 19, 20, 21, 22, 23, 24, 25, 26, and 27). The Toledo or Towne protein can be modified to affect HCMV life cycle by deletion, insertion and substitution into the DNA sequence, as discussed herein, or by chemical synthesis of different amino acid sequence or by chemical modification. Truncated proteins can be formed by a deletion of a portion of the DNA sequence or the introduction of termination signal(s) into the DNA sequence. Preferred deletions to the protein correspond to deleted amino acid sequence or sequences that contain at least one amino acid selected from the group consisting of Glu, Asp, Arg, Lys, Cys and Pro. More preferably at the deleted amino acid sequence or sequences contain at least two amino acids selected from the group consisting of Glu, Asp, Arg, Lys, Cys and Pro. More preferably the deleted amino acid sequence or sequences contain at least two prolines.

Other mutations of the protein useful in modifying HCMV life cycle include, but are not limited to, modification of cAMP phosphorylation (Arg/Lys-Arg/Lys-X-X-Asp/Glu) and/or, myristylization sites (Glycine-X1-X2-X3-Ser/Thr-X-X-Asp/Glu; where X1 is not Glu,Asp,Arg, Lys, His Pro, Phe, Tyr, Trp, where X2 is any amino acid and where X3 is not Pro), or modification of the PKC phosphorylation sites (Ser/Thr-X-Arg/Lys) and/or N-linked glycosylation sites (Asn-X-Ser/Thr; where X is not Pro).

The Toledo or Towne DNA sequences, analogs or fragments thereof can be expressed in a mammalian, insect, or microorganism host. The polynucleotide is inserted into a suitable expression vector compatible with the type of host cell employed and is operably linked to the control elements within that vector. Vector construction employs techniques which are known in the art. Site-specific DNA cleavage involved in such construction is performed by treating with suitable restriction enzymes under conditions which generally are specified by the manufacturer of these commercially available enzymes. A suitable expression vector is one that is compatible with the desired function (e.g., transient expression, long term expression, integration, replication, amplification) and in which the control elements are compatible with the host cell.

Mammalian Cell Expression

Vectors Suitable for replication in mammalian cells are known in the art, and can include viral replicons, or sequences that ensure integration of the sequence encoding the Toledo or Towne DNA into the host genome. Exemplary vectors include those derived from SV40, retroviruses, bovine papilloma virus, vaccinia virus, other herpesviruses and adenovirus.

Such suitable mammaliam expression vectors contain a promoter to mediate transcription of foreign DNA sequences and, optionally, an enhancer. Suitable promoters are known in the art and include viral promoters such as those from SV40, cytomegalovirus (CMV), Rous sarcoma virus (RSV), adenovirus (ADV), and bovine papilloma virus (BPV).

The optional presence of an enhancer, combined with the promoter described above, will typically increase expression levels. An enhancer is any regulatory DNA sequence that can stimulate transcription up to 1000-fold when linked to endogenous or heterologous promoters, with synthesis beginning at the normal mRNA start site. Enhancers are also active when placed upstream or downstream from the transcription initiation site, in either normal or flipped orientation, or at a distance of more than 1000 nucleotides from the promoter. See Maniatis, *Science* 236:1237(1987), Alberts, *Molecular Biology of the Cell,* 2nd Ed. (1989). Enhancers derived from viruses may be particularly useful, because they typically have a broader host range. Examples include the SV40 early gene enhancer (see Dijkema, *EMBO J.* 4:761(1985)) and the enhancer/promoters derived from the long terminal repeat (LTR) of the RSV (see Gorman, *Proc. Natl. Acad. Sci.* 79:6777(1982b)) and from human cytomegalovirus (see Boshart, *Cell* 41:521(1985)). Additionally, some enhancers are regulatable and become active only in the presence of an inducer, such as a hormone or metal ion (see Sassone-Corsi and Borelli, *Trends Genet.* 2:215(1986)); Maniatis, *Science* 236:1237(1987)). In addition, the expression vector can and will typically also include a termination sequence and poly(A) addition sequences which are operably linked to the Toledo or Towne coding sequence.

Sequences that cause amplification of the gene may also be desirably included in the expression vector or in another vector that is co-translated with the expression vector containing a Towne or Toledo DNA sequence, as are sequences which encode selectable markers. Selectable markers for mammalian cells are known in the art, and include for example, thymidine kinase, dihydrofolate reductase (together with methotrexate as a DHFR amplifier), aminoglycoside phosphotransferase, hygromycin B phosphotransferase, asparagine synthetase, adenosine deaminase, metallothionien, and antibiotic resistant genes such as neomycin.

The vector that encodes a novel Toledo or Towne protein or polypeptide of this invention can be used for transformation of a suitable mammalian host cell. Transformation can be by any known method for introducing polynucleotide into a host cell, including, for example packaging the polynucleotide in a virus and transducing a host cell with the virus. The transformation procedure used depends upon the host to be transformed. Methods for introduction of heterologous polynucleotide into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines.

Insect Cell Expression

The components of an insect cell expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media. Exemplary transfer vectors for introducing foreign genes into insect cells include pAc373 and pVL985. See Luckow and Summers, *Virology* 17:31(1989).

The plasmid can also contains the polyhedron polyadenylation signal and a procaryotic ampicillin-resistance (amp) gene and origin of replication for selection and propagation in *E. coli*. See Miller, *Ann. Rev. Microbiol.* 42:177(1988).

Baculovirus transfer vectors usually contain a baculovirus promoter, i.e., a DNA sequence capable of binding a baculovirus RNA polymerase and initiating the downstream (5' to 3') transcription of a coding sequence (e.g., structural gene) into mRNA. The promoter will have a transcription initiation region which is usually placed proximal to the 5' end of the coding sequence and typically includes an RNA polymerase binding site and a transcription initiation site. A baculovirus transfer vector can also have an enhancer, which, if present, is usually distal to the structural gene. Expression can be either regulated or constitutive.

Yeast And Bacteria Expression

A yeast expression system can typically include one or more of the following: a promoter sequence, fusion partner sequence, leader sequence, transcription termination sequence. A yeast promoter, capable of binding yeast RNA polymerase and initiating the downstream (3') transcription of a coding sequence (e.g. structural gene) into mRNA, will have a transcription initiation region usually placed proximal to the 5' end of the coding sequence. This transcription initiation region typically includes an RNA polymerase binding site (a "TATA Box") and a transcription initiation site. The yeast promoter can also have an upstream activator sequence, usually distal to the structural gene. The activator sequence permits inducible expression of the desired heterologous DNA sequence. Constitutive expression occurs in the absence of an activator sequence. Regulated expression can be either positive or negative, thereby either enhancing or reducing transcription.

Particularly useful yeast promoters include alcohol dehydrogenase (ADH) (EP Patent Pub. No. 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK)(EP Patent Pub. No. 329 203). The yeast PHO5 gene, encoding acid phosphatase, also provides useful promoter sequences. See Myanohara, *Proc. Natl. Acad. Sci. USA* 80:1(1983).

A Toledo or Towne DNA sequence, analog or an active fragment thereof can be expressed intracellularly in yeast. A promoter sequence can be directly linked with the sequence or fragment, in which case the first amino acid at the N-terminus of the recombinant protein will always be a methionine, which is encoded by the ATG start codon. If desired, methionine at the N-terminus can be cleaved from the protein by in vitro incubation with cyanogen bromide.

Intracellularly expressed fusion proteins provide an alternative to direct expression of a sequence. Typically, a DNA sequence encoding the N-terminal portion of a stable protein, a fusion partner, is fused to the 5' end of heterologous DNA encoding the desired polypeptide. Upon expression, this construct will provide a fusion of the two amino acid sequences. For example, the yeast or human superoxide dismutase (SOD) gene, can be linked at the 5' terminus of a sequence and expressed in yeast. The DNA sequence at the junction of the two amino acid sequences may or may not encode a cleavable site. See, e.g., EP Patent Pub. No. 196 056. Alternatively, the polypeptides can also be secreted from the cell into the growth media by creating a fusion protein comprised of a leader sequence fragment that provides for secretion in yeast or bacteria of the polypeptides. Preferably, there are processing sites encoded between the leader fragment and the sequence that can be cleaved either in vivo or in vitro. The leader sequence fragment typically encodes a signal peptide comprised of hydrophobic amino acids which direct the secretion of the protein from the cell. DNA encoding suitable signal sequences can be derived from genes for secreted yeast proteins, such as the yeast invertase gene (EP Patent Pub. No. 12 873) and the A-factor gene (U.S. Pat. No. 4,588,684). Alternatively, leaders of non-yeast origin, such as an interferon leader, can be used to provide for secretion in yeast (EP Patent Pub. No. 60057). Transcription termination sequences recognized by yeast are regulatory regions located 3' to the translation stop codon. Together with the promoter they flank the desired heterologous coding sequence. These flanking sequences direct the transcription of an mRNA which can be translated into the polypeptide encoded by the DNA.

Typically, the above described components, comprising a promoter, leader (if desired), coding sequence of interest, and transcription termination sequence, are put together in plasmids capable of stable maintenance in a host, such as yeast or bacteria. The plasmid can have two replication systems, so it can be maintained as a shuttle vector, for example, in yeast for expression and in a procaryotic host for cloning and amplification. Examples of such yeast-bacteria shuttle vectors include YEp24 (see Botstein, *Gene* 8:17–24 (1979)), pCl/1 (see Brake, *Proc. Natl. Acad. Sci. USA* 81:4642–4646(1984)), and YRp17 (see Stinchcomb, *J. Mol. Biol.* 158:157(1982)). In addition, the plasmid can be either a high or low copy number plasmid. A high copy number plasmid will generally have a copy number ranging from about 5 to about 200, and typically about 10 to about 150. A host containing a high copy number plasmid will preferably have at least about 10, and more preferably at least about 20. Either a high or low copy number vector may be selected, depending upon the effect on the host of the vector and the polypeptides. See, e.g., Brake, et al., supra.

Alternatively, the expression constructs can be integrated into the yeast genome with an integrating vector. Integrating vectors typically contain at least one sequence homologous to a yeast chromosome that allows the vector to integrate, and preferably contain two homologous sequences flanking the expression construct. See Orr-Weaver, *Methods In Enzymol.* 101:228–245(1983) and Rine, *Proc. Natl. Acad. Sci. USA* 80:6750(1983).

Typically, extrachromosomal and integrating expression vectors can contain selectable markers to allow for the selection of yeast strains that have been transformed. Selectable markers can include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker can also provide yeast with the ability to grow in the presence of toxic compounds, such as metal. For example, the presence of CUP1 allows yeast to grow in the presence of copper ions. See Butt, *Microbiol. Rev.* 51:351(1987).

Alternatively, some of the above described components can be put together into transformation vectors. Transformation vectors are typically comprised of a selectable marker that is either maintained in a replicon or developed into an integrating vector, as described above. Expression and transformation vectors, either extrachromosomal or integrating, have been developed for transformation into many yeasts. Exemplary yeasts cell lines are *Candida albicans* (Kurtz, *Mol. Cell. Biol.* 6:142(1986), *Candida maltosa* (Kunze, *J. Basic Microbiol.* 25:141(1985), *Hansenula polymorpha* (Gleeson, *J. Gen. Microbiol.* 132:3459(1986) and Roggenkamp, *Mol. Gen. Genet.* 202:302(1986), *Kluyvero-*

*myces fragilis* (Das, *J. Bacteriol.* 158:1165(1984), *Kluyveromyces lactis* (De Louvencourt, *J. Bacteriol.* 154:737(1983) and Van den Berg, *Bio/Technology* 8:135(1990), *Pichia guillerimondii* (Kunze, *J. Basic Microbiol.* 25:141(1985), *Pichia pastoris* (Cregg, *Mol. Cell. Biol.* 5:3376(1985), *Saccharomyces cerevisiae* (Hinnen, *Proc. Natl. Acad. Sci. USA* 75:1929(1978) and Ito, *J. Bacteriol.* 153:163(1983), *Schizosaccharomyces pombe* (Beach and Nurse, *Nature* 300:706(1981), and *Yarrowia lipolytica* (Davidow, *Curr. Genet.* 10:380471(1985) and Gaillardin, *Curr. Genet.* 10:49 (1985).

Methods of introducing exogenous DNA into yeast hosts are well-known in the art, and typically include either the transformation of spheroplasts or of intact yeast cells treated with alkali cations. Transformation procedures usually vary with the yeast species to be transformed. See the publications listed in the foregoing paragraph for appropriate transformation techniques.

Additionally, the gene or fragment thereof can be expressed in a bacterial system. In such system, a bacterial promoter is any DNA sequence capable of binding bacterial RNA polymerase and initiating the downstream (3') transcription of a coding sequence (e.g. a desired heterologous gene) into MRNA. A promoter will have a transcription initiation region which is usually placed proximal to the 5' end of the coding sequence. This transcription initiation region typically includes an RNA polymerase binding site and a transcription initiation site. A bacterial promoter can also have a second domain called an operator, that can overlap an adjacent RNA polymerase binding site at which RNA synthesis begins. The operator permits negative regulated (inducible) transcription, as a gene repressor protein can bind the operator and thereby inhibit transcription of a specific gene. Constitutive expression can occur in the absence of negative regulatory elements, such as the operator. In addition, positive regulation can be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*). See Raibaud, *Ann. Rev. Genet.* 18:173(1984). Regulated expression can therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) (see Chang, *Nature* 198:1056(1977), and maltose. Additional examples include promoter sequences derived from biosynthetic enzymes such as tryptophan (trp) (see Goeddel, *Nuc. Acids Res.* 8:4057(1981), Yelverton, *Nuc. Acids Res.* 9:731(1981), U.S. Pat. No. 4,738,921 and EP Patent Pub. Nos. 36 776 and 121 775). The lactomase (bla) promoter system (see Weissmann, *Interferon* 3 (ed. I. Gresser), the bacteriophage lambda PL promoter system (see Shimatake, *Nature* 292:128(128) and the T5 promoter system (U.S. Pat. No. 4,689,406) also provides useful promoter sequences.

In addition, synthetic promoters which do not occur in nature also function as bacterial promoters. For example, transcription activation sequences of one bacterial or bacteriophage promoter can be joined with the operon sequences of another bacterial or bacteriophage promoter, creating a synthetic hybrid promoter such as the tac promoter (see U.S. Pat. No. 4,551,433, Amann, *Gene* 25:167 (1983) and de Boer, *Proc. Natl. Acad. Sci.* 80:21(1983)). A bacterial promoter can include naturally occurring promoters of non-bacterial origin that have the ability to bind bacterial RNA polymerase and initiate transcription. A naturally occurring promoter of non-bacterial origin can be coupled with a compatible RNA polymerase to produce high levels of expression of some genes in prokaryotes. The bacteriophage T7 RNA polymerase/promoter system is exemplary. (see Studier, *J. Mol. Biol.* 189:113(1986) and Tabor, *Proc. Natl. Acad. Sci.* 82:1074(1985)).

In addition to a functioning promoter sequence, an efficient ribosome binding site is also useful for the expression of the DNA sequence or fragment thereof in prokaryotes. In *E. coli,* the ribosome binding site is called the Shine-Dalgarno (SD) sequence and includes an initiation codon (ATG) and a sequence 3–9 nucleotides in length located 3–11 nucleotides upstream of the initiation codon (see Shine, *Nature* 254:34(1975). The SD sequence is thought to promote binding of MRNA to the ribosome by the pairing of bases between the SD sequence and the 3' and of *E. coli* 16S rRNA (see Steitz, *Biological Regulation and Development: Gene Expression* (ed. R. F. Goldberger)(1979)).

The novel Toledo or Towne proteins of the invention can be expressed intracellularly. A promoter sequence can be directly linked with a novel Toledo or Towne DNA sequence, analog or a fragment thereof, in which case the first amino acid at the N-terminus will always be a methionine, which is encoded by the ATG start codon. If desired, methionine at the N-terminus can be cleaved from the protein by in vitro incubation with cyanogen bromide or by either in vivo on in vitro incubation with a bacterial methionine N-terminal peptidase. See EP Patent Pub. No. 219 237.

Fusion proteins provide an alternative to direct expression. Typically, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of an sequence fragment thereof and expressed in bacteria. The resulting fusion protein preferably retains a site for a processing enzyme (factor Xa) to cleave the bacteriophage protein from the sequence or fragment thereof (see Nagai, *Nature* 309:810(1984). Fusion proteins can also be made with sequences from the lacZ gene (Jia, *Gene* 60:197 (1987), the trpE gene (Allen, *J. Biotechnol.* 5:93(1987) and Makoff, *J. Gen. Microbiol.* 135:11(1989), and the Chey gene (EP Patent Pub. No. 324 647) genes. The DNA sequence at the junction of the two amino acid sequences may or may not encode a clearable site. Another example is a ubiquitin fusion protein. Such a fusion protein is made with the ubiquitin region that preferably retains a site for a processing enzyme (e.g., ubiquitin specific processing-protease) to cleave the ubiquitin from the polypeptide. Through this method, mature Towne or Toledo polypeptides can be isolated. See Miller, *Bio/Technology* 7:698(1989).

Alternatively, proteins or polypeptides can also be secreted from the cell by creating chimeric DNA molecules that encode a fusion protein comprised of a signal peptide sequence fragment that provides for secretion of the proteins or polypeptides in bacteria. (See, for example, U.S. Pat. No. 4,336,336). The signal sequence fragment typically encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the protein or polypeptide.

DNA encoding suitable signal sequences can be derived from genes for secreted bacterial proteins, such as the *E. coli* outer membrane protein gene (ompA) (Masui, Experimental Manipulation of Gene Expression (1983) and Ghrayeb, *EMBO J.* 3:2437(1984)) and the *E. coli* alkaline phosphatase signal sequence (phoA) (see Oka, *Proc. Natl. Acad. Sci.* 82:7212(1985). The signal sequence of the alpha-amylase gene from various Bacilus strains can be used to secrete heterologous proteins from *B. subtilis* (see Palva, *Proc. Natl. Acad. Sci.* 79:5582(1982) and EP Patent Pub. No. 244 042).

Transcription termination sequences recognized by bacteria are regulatory regions located 3' to the translation stop codon. Together with the promoter they flank the coding sequence. These sequences direct the transcription of an mRNA which can be translated into the Towne or Toledo protein or polypeptide encoded by the DNA sequence. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Typically, the promoter, signal sequence (if desired), coding sequence of interest, and transcription termination sequence are maintained in an extrachromosomal element (e.g., a plasmid) capable of stable maintenance in the bacterial host. The plasmid will have a replication system, thus allowing it to be maintained in the bacterial host either for expression or for cloning and amplification. In addition, the plasmid can be either a high or low copy number plasmid. A high copy number plasmid will generally have a copy number ranging from about 5 to about 200, and typically about 10 to about 150. A host containing a high copy number plasmid will preferably contain at least about 10, and more preferably at least about 20 plasmids.

Alternatively, the expression constructs can be integrated into the bacterial genome with an integrating vector. Integrating vectors typically contain at least one sequence homologous to the bacterial chromosome that allows the vector to integrate. Integrations appear to result from recombinations between homologous DNA in the vector and the bacterial chromosome. See e.g., EP Patent Pub. No. 127 328.

Typically, extrachromosomal and integrating expression constructs can contain selectable markers to allow for the selection of bacterial strains that have been transformed. Selectable markers can be expressed in the bacterial host and can include genes which render bacteria resistant to drugs such as ampicillin, chloramphenicol, erythromycin, kanamycin (neomycin), and tetracycline (see Davies, *Ann. Rev. Microbiol.* 32:469(1978). Selectable markers can also include biosynthetic genes, such as those in the histidine, tryptophan, and leucine biosynthetic pathways.

Alternatively, some of the above described components can be put together in transformation vectors. Transformation vectors are typically comprised of a selectable marker that is either maintained in an extrachromosal vector or an integrating vector, as described above.

Expression and transformation vectors, either extrachromosomal or integrating, have been developed for transformation into many bacteria. Exemplary are the expression vectors disclosed in Palva, *Proc. Natl. Acad. Sci.* 79:5582 (1982), EP Patent Pub. Nos. 036 259 and 063 953 and PCT Patent Publication WO 84/04541 (for *B. subtilis*); in Shimatake, *Nature* 292:128(1981), Amann, *Gene* 40:183 (1985), Studier, *J. Mol. Biol.* 189:113(1986) and EP Patent Pub. Nos. 036 776, 136 829 and 136 907 (for *E. coli*); in Powell, *Appl. Environ. Microbiol.* 54:655(1988) and U.S. Pat. No. 4,745,056 (for Streptococcus).

Methods of introducing exogenous DNA into bacterial hosts are well-known in the art, and typically include either the transformation of bacteria treated with $CaCl_2$ or other agents, such as divalent cations and DMSO. DNA can also be introduced into bacterial cells by electroporation. Exemplary methodologies can be found in Masson, *FEMS Microbiol. Let.* 60:273(1989), Palva, *Proc. Natl. Acad. Sci.* 79:5582(1982), EP Patent Pub. Nos. 036 259 and 063 953 and PCT Patent Pub. WO 84/04541 for Bacillus transformation. For campylobacter transformation, see e.g., Miller, *Proc. Natl. Acad. Sci.* 85:856(1988) and Wang. *J. Bacteriol.* 172:949(1990). For *E. coli*, see e.g., Cohen, *Proc. Natl. Acad. Sci.* 69:2110(1973), Dower, *Nuc. Acids Res.* 16:6127 (1988), Kushner, *Genetic Engineering: Proceedings of the International Symposium on Genetic Engineering* (eds. H. W. Boyer and S. Nicosia), Mandel, *J. Mol. Biol.* 53:159 (1970) and Taketo, *Biochem. Biophys. Acta* 949:318(1988). For Lactobacillus and Pseudomonas, see e.g., Chassy, *FEMS Microbiol. Let.* 44:173(1987) and Fiedler, *Anal. Biochem.* 170:38(1988), respectively. For Streptococcus, see e.g., Augustin, *FEMS Microbiol. Let.* 66:203(1990), Barany, *J. Bacteriol.* 144:698(1980), Harlander, *Streptococcal Genetics* (ed. J. Ferretti and R. Curtiss III)(1987), Perry, *Infec. Immun.* 32:1295(1981), Powell, *Appl. Environ. Microbiol* 54:655(1988) and Somkuti, *Proc. 4th Evr. Cong. Biotechnology* 1:412(1987).

The present invention is illustrated by the following examples.

MATERIALS AND METHODS

A. Cells and virus

Human CMV strains AD169, Towne and Toledo were obtained from E.S. Mocarski (Stanford University) and were used for all experiments. Two of these strains are also available through the ATCC, Accession Nos. VR-538 (AD169) and VR-977 (Towne). Virus was grown in cultures of human foreskin fibroblast (HF) cells with Dulbecco's modified Eagle's medium (DME) (JRH Biosciences, Lenexa, Kans.) as previously described in Spaete and Mocarski, *J. Virol* 56:135–43(1985), but supplemented with 10% fetal calf serum (FCS) (JRH Biosciences, Lenexa, Kans.), L-glutamine (2 mM), penicillin (100 units/ml), streptomycin (0.1 mg/ml) and pyruvate (1 mM). To prepare AD169, Towne and Toledo strain CMV DNAs by centrifugation to equilibrium on NaI gradients as previously described in Spaete and Mocarski, *J. Virol* 54:817–24(1985), roller bottles were infected with the CMV strains at a multiplicity of infection (MOI) of 0.001 plaque forming units (pfu)/cell to minimize the production of defective virus particles. The infected cells were refed at four days post infection with medium. At eight days post infection when the monolayer was well infected, cells were scraped into a 50 ml conical tube in 10 mls media per roller bottle and pelleted at 1000 revolutions per minute (rpm) for 10 minutes. Pellets were resuspended in 2.0 ml 0.01 M Tris and 0.01 EDTA (TE) (pH 7.4) with 1% NP40, 1% deoxycholate and incubated on ice until all cellular nuclei were lysed when viewed under a microscope. Lysates were transferred to a 2059 tube (Falcon) and spun at 2600 rpm for 5 minutes at 4° C. Supernatants were transferred to another 2059 tube and RNAse (Worthington-DNase free) was added at 50 µg/ml followed immediately by Proteinase K (200 µmg/ml) and 1% sodium dodecyl sulfate (SDS). Supernatants were incubated in a 65° C. water bath for 60 minutes, brought to 16 ml with TE, pH 7.4, added to 24 mls of saturated NaI and 0.15 ml ethidium bromide (5 mg/ml). Samples were centrifuged to equilibrium at 55,000 rpm at 20° C. for 24 hours in a Beckman Ti70 rotor. Fractions containing the viral DNA were extracted with butanol equilibrated with TE with gentle rocking followed by centrifugation at 3,000 rpm for 10 min at 20° C. and further extracted 2 to 3 times with butanol to reduce volume. Samples were extracted with an equal volume of isoamyl alcohol equilibrated with TE, spun and re-extracted. DNA was dialyzed against three changed of TE with 1% phenol and 1 M NaCl. The $OD_{260}$ and $OD_{280}$ were read to determine purity of the AD169, Toledo and Towne DNA.

Clinical isolates were obtained from M. Fiala (Rancho Mirage, Calif.), and S. Chou (Oregon Health Sciences University). Rapid isolation of HCMV infected cell viral DNA was carried out as previously described in Spaete and Frenkel, Cell 30:295–304(1982), except that DNA was not radiolabeled before purification. Briefly infected cell monolayers (25 cm$^2$ flasks) were rinsed twice with phosphate-buffered saline (PBS) and lysed in a 1.0 ml solution of 0.1 M NaCl, TE, pH 8.0, 0.05% SDS and 0.1 mg/ml Proteinase K. Lysates were incubated 2–24 hours at 37° C., extracted twice with 1 volume of phenol, 1 volume of chloroform followed by centrifugation at 2500 rpm for 5 minutes to separate phases. The aqueous phase was extracted twice with 1 volume of ether and the DNA was precipitated with 0.1 volume 3 M NaAC and two volumes of ethanol or isopropanol. DNA was chilled, collected by centrifugation or spooled on a glass rod, dried and resuspended in TE.

B. Plasmid DNA

Plasmids pXbaI E, pXbaI T and pXbaI Q (Thomsen and Stinski, 1981), representing Towne strain map units 0.69 to 0.8, were obtained from M. Stinski (University of Iowa).

Clone 65 was derived by cloning a gel extracted BamHI digested Toledo DNA fragment into the BamHI site of plasmid, pGEM®-3Zf+ (Promega, Madison, Wis.). Briefly, five µg of Toledo DNA was digested with 40 units of BamHI and electrophoresed in a preparative 1% low-melting-point agarose gel for 490 volt hours in 1 X TAE buffer. Toledo DNA migrating at ca. 5 kilobase pairs (kbp) was excised and the agarose was digested with 2 units of β-agarase I (New England BioLabs, Beverly, Mass.). This DNA fragment was precipitated with 2 volumes of isopropanol, chilled to −20° C., spun in an Eppendorf centrifuge for 15 minutes, dried and resuspended in 50 µl TE. The gel extracted fragment was ligated to BamHI digested pGEM®-3Zf+ using T4 DNA ligase (New England BioLabs, Beverly, Mass.), and an aliquot of the ligation mixture was used to transform competent Escherichia coli XL-1 Blues (Stratagene, La Jolla, Calif.) by the calcium shock method (Mandel and Higa, 1970), or by electroporation using methods as written in the Pulse Controller Guide published by BioRad (Richmond, Calif.).

Cosmid 1 is a ca. 53 kbp partially digested HindIII fragment of Toledo DNA spanning 0.69 to 0.87 map units cloned into cosmid pHC79 (Hohn and Collins, 1980) obtained from E. S. Mocarski (Stanford University). Subcloned from cosmid 1 were the following:

Clones 4 and C1300 were derived by cloning BamH1 digested fragments from Cosmid 1 cloned into a Bluescript M13+ plasmid vector. As such, these clones represent Toledo DNA sequence spanning portions of Cosmid 1.

Clone C23K was derived as a complete BamH1 digested fragment of Cosmid 1 DNA and circularized by ligation.

C. Preparation of radioactively labeled probes and hybridization.

Plasmid or viral DNA was radioactively labeled in vitro by nick translation (Rigby et at., 1977) with a kit (Boehringer Mannheim), and using [α$^{32}$P]dCTP (Amersham Corp.). Hybridizations to immobilized CMV DNA were performed essentially as described by Spaete and Mocarski, J. Virol 54:817–24(1985), but at 68° C. in a solution of 6 X SSC (1 X SSC is 0.15 M NaCl plus 0.015 M sodium citrate), 0.2% polyvinylpyrrolidone, 0.2% Ficoll, 0.2% bovine serum albumin, and 0.1% sodium dodecyl sulfate, with the amount of salmon sperm DNA being changed from 25 µg/ml to 100 µg/ml and 30% formamide being reduced to 15%.

DNA was transferred to Hybond-N+ nylon transfer membranes (Amersham Corp.), after restriction enzyme digestion and electrophoresis in 1% agarose gels by standard techniques (Maniatis et al., 1982). DNA was cross-linked to the membrane with 120,000 microjoules/cm$^2$ of UV irradiation using a UV Crosslinker 1000 (Hoefer Scientific Instruments, San Francisco, Calif.). Membranes were prehybridized 1 hour at 68° C. in solution A (6 X SSC, 0.2% polyvinylpyrrolidone, 0.2% Ficoll, 0.2% bovine serum albumin, 0.1% sodium dodecyl sulfate, 100 µg/ml salmon sperm DNA and 15% formamide), then nick-translated [α$^{32}$P]-labeled probe in a solution containing 100 µg/ml salmon sperm DNA was denatured by boiling for five minutes, snap-cooled on ice, added to the membrane and allowed to hybridize overnight at 68° C. After hybridization, unannealed probe was removed by rinsing the membrane 3 X with 2 XSSC followed by reincubation in solution A lacking salmon sperm DNA at 68° C. For 15 minutes. The washing procedure was repeated, the blot was rinsed in a large volume of 2 XSSC at room temperature, the membrane was air dried and autoradiographed using Kodak X-AR film.

D. Nucleotide sequence determination and analysis

All nucleic acid sequences were determined by the dideoxynucleotide chain termination method (Sanger et al., 1977). A variety of templates were prepared for sequencing; they included single-stranded phage DNA, double-stranded plasmid and cosmid DNA, viral genomic DNA, and PCR products. Manual and automated sequencing (with an ABI 373A instrument) were employed. Both one-cycle and multi-cycle sequencing protocols were used. The sequence was determined for both strands. Ambiguous regions were corrected by additional sequencing after proofreading. The primers used for sequencing were synthesized on an ABI 392 instrument (Applied Biosystems). The contig and analysis of the sequence were performed using MacDNASIS (Hitachi). The homology searches were performed using the BLAST program through NCBI services.

EXAMPLE 1

Identification of Novel Sequences in the Genomes of CMV Towne and Toledo Strain Isolates To determine the cross representation of DNA sequences in the Towne and Toledo strains of CMV, viral DNA from each strain was digested to completion with XbaI, ClaI, BamHI, BglII, EcoRI, and HindIII. After electrophoresis through a 1% agarose gel, the CMV DNAs were denatured in 0.2 M NaCl/0.6 M NaOH, neutralized in 0.6 M NaCl/1 M Tris, pH 7.5, in situ, and the gel was soaked in 20 X SSC for 30 minutes. Stereo blots were prepared by placing identically sized Hybond-N+ nylon membranes (Amersham Corp.), on either side of the gel and transferring the DNAs to the membranes in both directions using the capillary action of paper towels. After blotting overnight in 20 X SSC, the membranes were washed in 2 X SSC and the DNA was immobilized on the membrane by UV irradiation as described above.

DNA probes of Towne and Toledo DNA with an average size of 500 bp were prepared by sonicating 10 µg of each DNA in a 2063 tube (Falcon Plastics) using 4 pulses of 10 seconds each at a setting of 3 on a Heat Systems, Inc. sonicator (Farmingdale, N.Y.). Following sonication, the viral DNAs were digested with the restriction enzymes AvaI, BanI and BfaI, to further reduce the size complexity of the probe DNA. These enzymes were chosen because a search of the AD169 DNA database sequences (EMBL accession number X17403), revealed abundant cut sizes (326, 386, and 341, respectively); their restriction enzyme digestion buffers are compatible; and their sites do not overlap. Ethidium bromide stained gels of the sheared viral DNAs prepared in this manner revealed a range of DNA sizes from 1300 bp to less than 100 bp, with the majority of DNA migrating at approximately 300 bp as judged by comigration with a HaeIII digested ØX174 DNA standard marker (New England BioLabs, Beverly, Mass.). The Towne and Toledo sheared probe DNA was then nick translated using $[\alpha^{32}P]dCTP$ (Amersham Corp.) as described above and each probe was applied to stereo blots of immobilized, restriction enzyme digested, Towne and Toledo DNAs. After hybridization and autoradiography, the hybridization patterns were analyzed to determine the fragments on each DNA profile which did not hybridize with the heterologous strain probe but did hybridize with the homologous strain probe. For example, the loss of a signal for a prominent 5 kbp band on the BamHI digest of Toledo DNA when using the Towne probe, which was present when the Toledo DNA was used to probe itself, revealed a region of sequence divergence between the two isolates (see FIG. 3).

This 5 kbp fragment was cloned by gel extraction as described above and designated clone 65. The clone 65 Toledo DNA was sequenced in its entirety and compared to Towne DNA sequence generated from the pXbaI T clone which was shown to be divergent from AD169 DNA sequences (see Example 2 below). The full sequence of clone 65 is shown in FIG. 1. In FIG. 1, Clone 65 begins with nucleotide 4664 and ends with nucleotide 9327. Surprisingly, the DNA from the pXbaI T clone of Towne DNA (1,856 bp) and clone 65 of Toledo DNA (4,668 bp) shared 104 bp of sequence identity. This small stretch of sequence homology allowed mapping of the region of Toledo DNA divergence to the boundary of the Unique Long ($U_L$) component and the inverted repeats (alternatively termed IRL or b' sequences) on the AD169 and Towne DNA maps. These newly isolated Toledo strain nucleotide sequences form clone 65 were not represented in the reference laboratory strain, AD169, which has been sequenced in its entirety by Chee and colleagues (EMBL accession number X17403).

EXAMPLE 2

Identification of Novel Sequences in the Genome of CMV Towne Not Found in Reference Strain AD169

DNA sequence heterogeneity between the Towne strain and the AD169 strain has been found. See, Pritchett, *J. Virology* 36:152–61 (1980). However, although the gross structural organization of the CMV genome has been determined and strain to strain restriction site polymorphisms have been mapped for many strains, strain-to-strain differences on the nucleotide level have not been determined. The laboratory strain AD169 was the first CMV isolate to be sequenced and has served as the reference strain in defining the genetic complexity of the CMV genome.

In order to examine nucleotide sequence differences between Towne and AD169, we focused on the region shown to be divergent in the Toledo strain, i.e. the boundary between the $U_L$ component and the b' sequences, as explained in detail in Example 1. Plasmid pXbaI T was labeled using the NEBlot™ Phototope™ Detection Kit (New England Biolabs, Beverly, Mass.), and used as a probe on blots of immobilized restriction enzyme digested Towne, Toledo and AD169 DNAs. Briefly, pXbaI T was linearized with PvuII, ethanol precipitated and resuspended in 34 µl of nuclease free water. The plasmid was denatured in boiling water for five minutes, snap cooled on ice for five minutes and centrifuged briefly at 4° C. The following reagents were added to the tube in the order listed: 10 µl of 5 X labeling mix, 5 µl of dNTP mix, 1 µl of DNA polymerase I (Klenow fragment). The mix was incubated at 37° C. for 6 hours and the reaction was terminated by adding 5 µl of 0.2 M EDTA, pH 8.0. The probe was precipitated by adding 5 µl of 4 M LiCl and 150 µl of ethanol, to −80° C. For 30 minutes, pelleted in an Eppendorf centrifuge, washed with 70% ethanol and resuspended in 20 µl of Resuspension Buffer as supplied by the kit. The hybridization reaction was essentially as described above except that after hybridization the membrane was washed twice in 2 X SSC, 0.1% SDS at room temperature for 5 minutes each followed by two washes in 0.1 X SSC, 0.1% SDS at 68° C. For 15 minutes. The detection reactions link the biotinylated probes to alkaline phosphatase through a strepavidin bridge and the hybridized probe was visualized by cleavage of the Lumigen-PPD substrate. The blocking steps, strepavidin incubation, alkaline phosphatase incubation and Lumigen-PPD reaction were carried out as described in the kit manual. Exposure of the blots to Kodak XAR film revealed that, as expected, (i) and XbaI digested fragment of sized 1.85 kbp (XbaI T) was hybridized on Towne DNA probed with pXbaI T and (ii) a comigrating XbaI digested fragment was present in Toledo DNA. The AD169 DNA failed to show any hybridization signal on any of the restriction enzyme digestion patterns. Nucleotide sequence of pXbaI T confirmed the total lack of identity of the Towne DNA and AD169 DNA. Nucleotide sequencing of cosmid 1 DNA (see B. Plasmid DNA in Material and Methods, above) from Toledo revealed extensive sequence identity between the newly identified Towne DNA and the Toledo DNA of cosmid 1 in this region. Surprisingly, the orientation of the sequence was reversed in Toledo relative to Towne.

EXAMPLE 3

Identification of Novel Toledo DNA Sequences in the Genomes of Recent Clinical Isolates and Not Found in Reference Strain AD169

To determine the penetrance of sequences represented by clone 65 in recent clinical isolates, five representative clinical isolates (HCMVF, C128, C354, C793 and C980) were digested with restriction enzymes BamHI and XbaI along with the Toledo, Towne and AD169 DNAs prepared as described in the Materials and Methods section above, electrophoresed through agarose, transferred to a Hybond-N+ nylon transfer membrane, and probed with nick-translated $[\alpha^{32}P]$-labeled clone 65 according to the procedures outlined in the Materials and Methods section. As can be seen in FIG. 4, the autoradiographs revealed that homology was detected in all of the clinical isolates. In FIG. 4, a band at ca. 5 kbp is visible in lane 1 (the Toledo DNA), appears in Towne DNA (lane 2), is missing from lane 3 (the AD 169 DNA), and visible in lanes 4 through 8 (the clinical isolates HCMVF, C128, C354, C793 and C980). These results demonstrate that the newly isolated sequence found in the Toledo strain of HCMV is also present in the recent clinical isolates but is not present in the AD169 reference strain. Nucleotide sequence analysis reveals the reason for the weak hybridization signal to the Towne DNA fragment is due to the existence of only 151 nucleotides of sequence identify with Towne DNA. The shared 104 bp sequence identify in Example 1 is responsible for a weak hybridization signal to XbaI "T" sized fragments from both Towne and Toledo DNAs seen in the XbaI digests (lanes 9 and 10). The XbaI digest of the clinical isolates (lanes 12 through 16) also reveals hybridization to multiple high molecular weight bands. Analysis of these and other clinical isolate genomes with other probes in the region has revealed that the shared sequences may be inverted orientation in some isolates relative to the orientation in the Toledo strain.

FIG. 6 is a schematic illustration of the relative positions of novel sequences identified in Toledo genomic DNA, Towne genomic DNA in a comparison with AD169 strain genomic DNA. The dashed lines delimit the region of the genome where homologous and divergent sequences are found. The top line illustrates a Toledo DNA restriction map showing BamHI (indicated by "B") and XbaI (indicated by "X") restriction enzyme sites extending between the homology breakpoints identified by inverted triangles at nucleotides 175068 and 188843 (numbered with reference to the AD169 DNA sequence—EMBL accession number X17403). Subclones 4, 1300, C23K and 65 of the Toledo DNA sequence are shown in boxes above the map. An inverted region of homology with respect to Towne is shown by the inverted triangles between nucleotides 178221 and 175082. Unique sequences are shown by a thin line, and inverted repeat sequences denoted by thick lines, b'a'c'. The end of the c' repeats is shown with an arrow at nucleotide 191412. The middle line illustrates a Towne DNA restriction map showing BamHI (B) and XbaI (X) restriction enzyme sites as described above for Toledo and showing XbaI clones E, T, and Q in boxes below. Shaded area refers to homologous regions shared with Toledo DNA but inverted in orientation. Nucleotide numbers shown are with reference to the AD169 DNA sequence. Undetermined extent of b' repeat sequences in the Towne strain is shown by thin lines at AD169 strain nucleotide reference 180034. The bottom line illustrates the AD169 genome displayed in the prototype orientation. Unique sequences are displayed by a thin line, and inverted repeats of the long ($U_L$) and short ($U_S$) components are denoted by boxes, ab–b'a', and a'c'–ca. The a sequence, is a terminal direct repeat with an inverted copy (a'), at the junction of the long and short components. The length of the AD169 DNA sequence is indicated as 229354 nucleotides and the map position of the internal repeats are shown with the nucleotide reference numbers and arrows.

EXAMPLE 4

Open Reading Frame Analysis of the Novel Toledo and Towne DNA Sequences

The novel Toledo and Towne sequences encoded potential open reading frames (ORFs). Using an arbitrarily chosen parameter of 10 kiloDaltons as the minimum calculated protein molecular weight, a total of 36 ORFs were identified in the novel Toledo sequence and a total of 4 ORFs were identified in the novel Towne sequence. The putative amino acid sequences of these ORFs are set forth in the sequence listing (SEQ ID NOS: 2, 3, 4, 5, 7, 8, 9, 10, 11, 12, 13, 14, 15, 16, 17, 18, 19, 20, 21, 22, 23, 24, 25, 26, and 27). FIG. 5 shows the schematic presentation of these ORFs in the novel Toledo and Towne DNA sequences, together with previously reported AD169 ORFs of the corresponding region. Names were assigned for these ORFs starting from UL133 as the first ORF at the left side of the UL in Toledo sequence. The first ORF in the novel Towne sequence was assigned as UL147, which was determined to be present in the novel Toledo sequence disclosed here. UL130 and UL132 in AD169 were determined to be present in the novel Toledo sequence. Additionally, UL153 and UL154 exhibited regions of homology to IRL14 and IRL12, respectively. All ORFs were searched for homologous sequence in the non-redundant databases of NCBI using the BLASTP program. Among all ORFs searched, only UL132 identified a homologue in the database, which was HCMV mtrIII (GenBank Accession No. X75606), exhibiting 76% identity at the amino acid level. The solid circle identified the ORFs that contained the potential N-linked glycosylation site sequence, N-X(-P)-S/T. These potential glycoproteins may be biologically significant as antigenic or immunogenic molecules.

The present investigation is not to be limited in scope by the specific embodiments described which are intended as single illustrations of individual aspects of the invention, and any constructs, viruses or enzymes which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

What is claimed is:

1. A method of producing a recombinant human cytomegalovirus comprising:

(A) in cells permissive for growth of cytomegalovirus, co-transfecting a plasmid containing a DNA sequence comprising the nucleotide sequence of SEQ ID NO:6 or comprising at least one complete open reading frame thereof and a selectable marker with viral DNA comprising the AD169 strain cytomegalovirus or the Towne strain cytomegalovirus; and (B) identifying the recombinant human cytomegalovirus resulting from said co-transfection.

2. An immunogenic composition comprising a recombinant human cytomegalovirus made by the method of claim 1.

3. A method of prophylactic treatment of an human cytomegalovirus-related disease or condition comprising administering to a patient an immunogenic composition of claim 2 in an amount sufficient to simulate an immune response in said patient.

4. A method of producing a recombinant human cytomegalovirus comprising:

(A) in cells permissive for growth of cytomegalovirus, superinfecting the AD169 strain cytomegalovirus or the Towne strain cytomegalovirus with a plasmid containing a DNA sequence comprising the nucleotide sequence of SEQ ID NO:6 or comprising at least one complete open reading frame thereof and a selectable marker; and (B) identifying the recombinant human cytomegalovirus resulting from said superinfection.

5. An immunogenic composition comprising a recombinant human cytomegalovirus made by the method of claim 4.

6. A method of prophylactic treatment of an human cytomegalovirus-related disease or condition comprising administering to a patient an immunogenic composition of claim 5 in an amount sufficient to stimulate an immune response in said patient.

7. A pharmaceutical composition comprising a protein encoded by a DNA sequence comprising the nucleotide sequence of SEQ ID NO:6 or at least one complete reading frame thereof, in admixture with a pharmaceutically acceptable carrier.

8. A method of prophylactic treatment of an human cytomegalovirus-related disease or condition comprising administering to a patient an immunogenic composition of claim 7 in an amount sufficient to simulate an immune response in said patient.

* * * * *